United States Patent
Beeson et al.

(10) Patent No.: US 9,920,029 B2
(45) Date of Patent: *Mar. 20, 2018

(54) ISATIN COMPOUNDS, COMPOSITIONS AND METHODS FOR TREATMENT OF DEGENERATIVE DISEASES AND DISORDERS

(71) Applicant: MUSC Foundation For Research Development, Charleston, SC (US)

(72) Inventors: Craig C. Beeson, Charleston, SC (US); Christopher C. Lindsey, Wadmalaw Island, SC (US); Yuri K. Peterson, Charleston, SC (US); Baerbel Rohrer, Charleston, SC (US)

(73) Assignee: MUSC FOUNDATION FOR RESEARCH DEVELOPMENT, Charleston, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/685,962

(22) Filed: Apr. 14, 2015

(65) Prior Publication Data

US 2015/0218128 A1    Aug. 6, 2015

Related U.S. Application Data

(63) Continuation of application No. 13/798,383, filed on Mar. 13, 2013, now Pat. No. 9,079,853.

(51) Int. Cl.

| | | |
|---|---|---|
| *C07D 209/36* | (2006.01) | |
| *C07D 209/38* | (2006.01) | |
| *C07D 401/06* | (2006.01) | |
| *C07D 403/06* | (2006.01) | |
| *C07D 401/04* | (2006.01) | |
| *C07D 403/04* | (2006.01) | |
| *C07D 209/34* | (2006.01) | |

(52) U.S. Cl.
CPC ......... *C07D 401/06* (2013.01); *C07D 209/34* (2013.01); *C07D 209/36* (2013.01); *C07D 209/38* (2013.01); *C07D 401/04* (2013.01); *C07D 403/04* (2013.01); *C07D 403/06* (2013.01)

(58) Field of Classification Search
CPC .. C07D 401/06; C07D 209/34; C07D 209/36; C07D 209/38; C07D 401/04; C07D 403/04; C07D 403/06
See application file for complete search history.

(56) References Cited

U.S. PATENT DOCUMENTS

2011/0021974 A1* 1/2011 Shantha ............... A61K 9/0048
604/20

FOREIGN PATENT DOCUMENTS

WO    2011119869    9/2011

OTHER PUBLICATIONS

Hu, "Nickel-Catalyzed Intramolecular Nucleophilic Addition of Aryl or Vinyl Chlorides to a-Ketoamides Through C_Cl Bond Activation", Chem. Eur. J. 2011, 17, pp. 5234-5237.

* cited by examiner

*Primary Examiner* — Sahar Javanmard

(57) ABSTRACT

Provided herein are compounds of the formula (I):

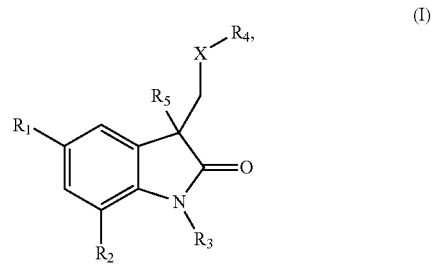

as well as pharmaceutically acceptable salts thereof, wherein the substituents are as those disclosed in the specification. These compounds, and the pharmaceutical compositions containing them, are useful for the treatment of degenerative diseases and disorders.

26 Claims, No Drawings

ISATIN COMPOUNDS, COMPOSITIONS AND METHODS FOR TREATMENT OF DEGENERATIVE DISEASES AND DISORDERS

CROSS REFERENCE TO RELATED APPLICATIONS

This application claims priority to and is a continuation of pending U.S. patent application Ser. No. 13/798,383, filed Mar. 13, 2013, incorporated by references herein.

This application is related to U.S. application Ser. Nos. 13/798,394, filed Mar. 13, 2013; 13/798,421, filed Mar. 13, 2013; and U.S. application Ser. No. 13/636,754, filed Feb. 7, 2013, which claims priority to PCT/US2011/029846, filed Mar. 24, 2011.

FIELD OF THE INVENTION

The invention is directed to compounds of formula (I):

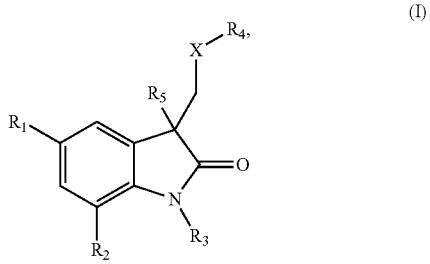

and to pharmaceutical compositions comprising the compounds. The compounds and compositions disclosed herein protect against calcium- and oxidative-stress mediated damage to mitochondrial functions and are useful for the treatment of degenerative diseases and disorders.

All documents cited or relied upon below are expressly incorporated herein by reference.

BACKGROUND OF THE INVENTION

Mitochondria are cellular organelles present in most eukaryotic cells. One of their primary functions is oxidative phosphorylation, a process through which energy derived from metabolism of fuels like glucose or fatty acids is converted to ATP, which is then used to drive various energy-requiring biosynthetic reactions and other metabolic activities. Mitochondria have their own genomes, separate from nuclear DNA, comprising rings of DNA with about 16,000 base pairs in human cells. Each mitochondrion may have multiple copies of its genome, and individual cells may have hundreds of mitochondria. In addition to supplying cellular energy, mitochondria are involved in a range of other processes, such as signaling, cellular differentiation, cell death, as well as the control of the cell cycle and cell growth (McBride et al., Curr. Biol., 2006, 16 (14): R551).

As mitochondria produce ATP, they simultaneously yield reactive oxygen species (ROS), which are harmful free radicals that circulate throughout the cell, the mitochondria, and the body, causing more damage. The circulation of ROS leads to the activation of reactive nitrogen compounds, which in turn induce, or activate, genes in the DNA that are associated with many degenerative diseases. The DNA for each mitochondrion (mtDNA) remains unprotected within the membrane of the mitochondrion itself. In comparison to the DNA in the nucleus of the cell (nDNA), mtDNA is easily damaged by free radicals and the ROS that it produces. Freely floating mtDNA lacks protective measures associated with nDNA, and therefore suffers from multiple mutations. It has been estimated that the lack of protective measures results in mutations to mtDNA occurring 10 to 20 times more frequently than mutations to nDNA.

Mitochondrial damage and/or dysfunction contribute to various disease states. Some diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms can be present, depending on the extent to which different tissues are involved.

A fertilized ovum might contain both normal and genetically defective mitochondria. The segregation of defective mitochondria into different tissues during division of this ovum is a stochastic process, as will be the ratio of defective to normal mitochondria within a given tissue or cell (although there can be positive or negative selection for defective mitochondrial genomes during mitochondrial turnover within cells). Thus, a variety of different pathologic phenotypes can emerge out of a particular point mutation in mitochondrial DNA. Conversely, similar phenotypes can emerge from mutations or deletions affecting different genes within mitochondrial DNA. Clinical symptoms in congenital mitochondrial diseases often manifest in postmitotic tissues with high energy demands like brain, muscle, optic nerve, and myocardium, but other tissues including endocrine glands, liver, gastrointestinal tract, kidney, and hematopoietic tissue are also involved, again depending in part on the segregation of mitochondria during development, and on the dynamics of mitochondrial turnover over time.

In addition to congenital disorders involving inherited defective mitochondria, acquired mitochondrial damage and/or dysfunction contribute to diseases, particularly neurodegenerative disorders associated with aging like Parkinson's, Alzheimer's, Huntington's Diseases. The incidence of somatic mutations in mitochondrial DNA rises exponentially with age; and diminished respiratory chain activity is found universally in aging people. Mitochondrial dysfunction is also implicated in excitotoxic neuronal injury, such as that associated with seizures or ischemia.

Other pathologies with etiology involving mitochondrial damage and/or dysfunction include schizophrenia, bipolar disorder, dementia, epilepsy, stroke, cardiovascular disease, retinal degenerative disease (e.g., age-related macular degeneration, Stargardt's disease, glaucoma, retinitis pigmentosa, and optic nerve degeneration), and diabetes mellitus. A common thread thought to link these seemingly-unrelated conditions is cellular damage causing oxidative stress. Oxidative stress is caused by an imbalance between the production of reactive oxygen and a biological system's ability to readily detoxify the reactive intermediates or easily repair the resulting damage. All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids, and DNA.

Mitochondrial damage and/or dysfunction particularly contribute to degenerative diseases. Degenerative diseases are diseases in which the function or structure of the affected tissues or organs will progressively deteriorate over time. Some examples of degenerative diseases are retinal degenerative disease, e.g., age-related macular degeneration, Stargardt's disease, glaucoma, retinitis pigmentosa, and optic nerve degeneration; amyotrophic lateral sclerosis (ALS), e.g., Lou Gehrig's disease; Alzheimer's disease; Parkinson's Disease; multiple system atrophy; Niemann Pick disease; atherosclerosis; progressive supranuclear palsy; cancer; Tay-Sachs disease; diabetes; heart disease; keratoconus; inflammatory bowel disease (IBD); prostatitis; osteoarthritis; osteoporosis; rheumatoid arthritis; and Huntington's disease.

Treatment of degenerative diseases involving mitochondrial damage and/or dysfunction has heretofore involved administration of vitamins and cofactors used by particular elements of the mitochondrial respiratory chain. Coenzyme Q (ubiquinone), nicotinamide, riboflavin, carnitine, biotin, and lipoic acid are used in patients with occasional benefit, especially in disorders directly stemming from primary deficiencies of one of these cofactors. However, while useful in isolated cases, no such metabolic cofactors or vitamins have been shown to have general utility in clinical practice in treating degenerative diseases involving mitochondrial damage and/or dysfunction.

Therefore, a need exists for new drug therapies for the treatment of subjects suffering from or susceptible to the above disorders or conditions associated with mitochondrial damage and/or dysfunction. In particular, a need exists for new drugs having one or more improved properties (such as safety profile, efficacy or physical properties) relative to those currently available.

SUMMARY OF THE INVENTION

The present invention is directed to compounds of formula I:

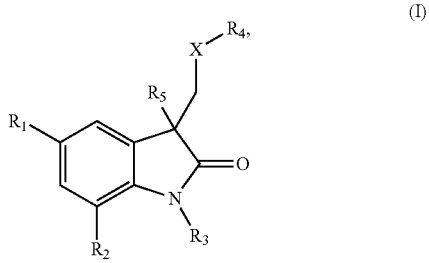

wherein:
X is —C(O)— or a single bond;
$R_1$ and $R_2$ are, independently of each other, hydrogen, lower alkyl or halogen;
$R_3$ is unsubstituted lower alkyl or lower alkyl monosubstituted with —C≡CH, piperidinyl, —N$_3$, morpholinyl or phenyl, wherein $R_3$ is not methyl when X is —C(O)—;
$R_4$ is (i) pyridinyl, unsubstituted or mono- or bi-substituted independently with halogen, hydroxyl, alkoxy or —C≡CH, (ii) phenyl, unsubstituted or mono-, bi- or tri-substituted independently with alkoxy or hydroxy,
(iii) 1H-indol-3-yl, or
(iv) 1-benzoyl-1H-indol-3-yl; and
$R_5$ is hydroxyl or —OBz,
or a pharmaceutically acceptable salt thereof.

The present invention is also directed to pharmaceutical compositions containing the above compounds and to methods of treating degenerative diseases and disorders.

DETAILED DESCRIPTION OF THE INVENTION

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydropyranyl, 1,3-dioxanyl and the like. The heterocycloalkyl groups may be unsubstituted or substituted and attachment may be through their carbon frame or through their heteroatom(s) where appropriate.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl groups.

As used herein, the term "halogen" means a fluorine, chlorine, bromine or iodine radical, preferably a fluorine, chlorine or bromine radical, and more preferably a bromine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In one embodiment of the invention, provided is a compound of formula (I):

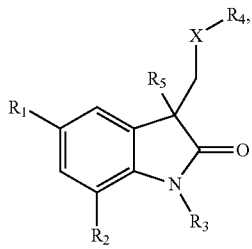

wherein:

X is —C(O)— or a single bond;

$R_1$ and $R_2$ are, independently of each other, hydrogen, lower alkyl or halogen;

$R_3$ is unsubstituted lower alkyl or lower alkyl mono-substituted with —C≡CH, piperidinyl, —$N_3$, morpholinyl or phenyl, wherein $R_3$ is not methyl when X is —C(O)—;

$R_4$ is (i) pyridinyl, unsubstituted or mono- or bi-substituted independently with halogen, hydroxyl, alkoxy or —C≡CH,
   (ii) phenyl, unsubstituted or mono-, bi- or tri-substituted independently with alkoxy or hydroxy,
   (iii) 1H-indol-3-yl, or
   (iv) 1-benzoyl-1H-indol-3-yl; and $R_5$ is hydroxyl or —OBz, or a pharmaceutically acceptable salt thereof.

In another embodiment of the invention, provided is a compound according to formula I wherein X is —C(O)—.

In another embodiment of the invention, provided is a compound according to formula I wherein X is a single bond.

In another embodiment of the invention, provided is a compound according to formula I wherein $R_1$ is hydrogen, lower alkyl or halogen.

In another embodiment of the invention, provided is a compound according to formula I wherein $R_2$ is hydrogen, lower alkyl or halogen.

In another embodiment of the invention, provided is a compound according to formula I wherein both $R_1$ and $R_2$ are hydrogen.

In another embodiment of the invention, provided is a compound according to formula I wherein one of $R_1$ or $R_2$ is hydrogen and the other is methyl.

In another embodiment of the invention, provided is a compound according to formula I wherein one of $R_1$ or $R_2$ is hydrogen and the other is chlorine.

In another embodiment of the invention, provided is a compound according to formula I wherein both $R_1$ and $R_2$ are chlorine.

In another embodiment of the invention, provided is a compound according to formula I wherein $R_3$ is an unbranced, unsubstituted lower alkyl.

In another embodiment of the invention, provided is a compound according to formula I wherein $R_3$ is a branched, unsubstituted lower alkyl.

In another embodiment of the invention, provided is a compound according to formula I wherein $R_3$ is lower alkyl mono-substituted with —C≡CH, piperidinyl, —$N_3$, morpholinyl or phenyl.

In another embodiment of the invention, provided is a compound according to formula I wherein $R_4$ is unsubstituted In another embodiment of the invention, provided is a compound according to formula I wherein $R_4$ is pyridinyl mono- or bi-substituted independently with halogen, hydroxyl, alkoxy or —C≡CH.

In another embodiment of the invention, provided is a compound according to formula I wherein $R_4$ is unsubstituted phenyl.

In another embodiment of the invention, provided is a compound according to formula I wherein $R_4$ is phenyl monosubstituted with alkoxy or hydroxyl.

In another embodiment of the invention, provided is a compound according to formula I wherein $R_4$ phenyl bi-substituted independently with alkoxy or hydroxyl.

In another embodiment of the invention, provided is a compound according to formula I wherein $R_4$ is phenyl tri-substituted independently with alkoxy or halogen.

In another embodiment of the invention, provided is a compound according to formula I wherein $R_4$ is phenyl monosubstituted with methoxy.

In another embodiment of the invention, provided is a compound according to formula I wherein $R_4$ is phenyl bi-substituted with methoxy.

In another embodiment of the invention, provided is a compound according to formula I wherein $R_4$ is phenyl tri-substituted with methoxy.

In another embodiment of the invention, provided is a compound according to formula I wherein $R_4$ is 1H-indol-3-yl, or 1-benzoyl-1H-indol-3-yl.

In another embodiment of the invention, provided is a compound according to formula I wherein $R_5$ is hydroxyl.

In another embodiment of the invention, provided is a compound according to formula I wherein $R_5$ is —OBz.

In another embodiment of the invention, provided is a compound according to formula I wherein X is a single bond and R4 is phenyl, unsubstituted or mono-, bi- or tri-substituted independently with alkoxy or hydroxyl.

In another embodiment of the invention, provided is a compound according to formula I wherein the compound is:

3-((3-bromopyridin-2-yl)methyl)-3-hydroxy-1-isopentyl-5-methylindolin-2-one;

5-chloro-1-ethyl-3-hydroxy-3-((4-hydroxypyridin-2-yl) methyl)indolin-2-one;

5-chloro-3-hydroxy-3-((3-methoxypyridin-2-yl)methyl)-1-phenethylindolin-2-one;

5-chloro-3-hydroxy-1-(2-(piperidin-1-yl)ethyl)-3-(pyridin-2-ylmethyl)indolin-2-one;

5-chloro-3-hydroxy-3-(5-methoxypyridin-2-yl)methyl)-1-propylindolin-2-one;

3-hydroxy-3-(5-methoxypyridin-2-yl)methyl)-5-methyl-1-propylindolin-2-one;

5-chloro-1-ethyl-3-hydroxy-3-((3-methoxypyridin-2-yl) methyl)indolin-2-one;

1-ethyl-3-hydroxy-3-((3-methoxypyridin-2-yl)methyl)-5-methylindolin-2-one;

3-hydroxy-5-methyl-1-phenethyl-3-(pyridin-2-ylmethyl)indolin-2-one;

5-chloro-1-ethyl-3-hydroxy-3-(pyridin-2-ylmethyl)indolin-2-one;

3-hydroxy-3-((5-methoxypyridin-2-yl)methyl)-5-methyl-1-phenethylindolin-2-one;

1-butyl-3-hydroxy-3-(2-oxo-2-(pyridin-2-yl)ethyl)indolin-2-one;

3-(2-(1H-indol-3-yl)-2-oxoethyl)-3-hydroxy-5-methyl-1-(pent-4-yl)-1-yl)indolin-2-one;

5-chloro-3-(2-(6-ethynylpyridin-2-yl)-2-oxoethyl)-3-hydroxy-1-propylindolin-2-one;
3-(2-(1H-indol-3-yl)-2-oxoethyl)-3-hydroxy-1-isopentyl-5-methylindolin-2-one;
3-hydroxy-1-isobutyl-3-(2-oxo-2-(pyridin-2-yl)ethyl)indolin-2-one;
5-chloro-3-hydroxy-1-isobutyl-3-(2-(6-methoxypyridin-2-yl)-2-oxoethyl)indolin-2-one;
5-chloro-3-hydroxy-3-(2-(6-methoxypyridin-2-yl)-2-oxoethyl)-1-(2-(piperidin-1-yl)ethyl)indolin-2-one;
5-chloro-1-ethyl-3-hydroxy-3-(2-oxo-2-(pyridin-2-yl)ethyl)indolin-2-one;
3-(2-(1H-indol-3-yl)-2-oxoethyl)-3-hydroxy-1-isobutylindolin-2-one;
3-(2-(1H-indol-3-yl)-2-oxoethyl)-3-hydroxy-1-isopentylindolin-2-one;
5-chloro-3-(2-(2,6-dimethoxypyridin-3-yl)-2-oxoethyl)-3-hydroxy-1-propylindolin-2-one;
5-chloro-3-hydroxy-3-(2-oxo-2-(pyridin-2-yl)ethyl)-1-propylindolin-2-one;
3-(2-(1H-indol-3-yl)-2-oxoethyl)-3-hydroxy-5-methyl-1-propylindolin-2-one;
3-(2-(2,6-dimethoxypyridin-3-yl)-2-oxoethyl)-3-hydroxy-5-methyl-1-propylindolin-2-one;
3-hydroxy-3-(2-(6-methoxypyridin-2-yl)-2-oxoethyl)-5-methyl-1-propylindolin-2-one;
3-(2-(1H-indol-3-yl)-2-oxoethyl)-1-(3-azidopropyl)-3-hydroxy-5-methylindolin-2-one;
1-(3-azidopropyl)-3-hydroxy-3-(2-(6-methoxypyridin-2-yl)-2-oxoethyl)-5-methylindolin-2-one;
3-hydroxy-1-isobutyl-3-(2-(6-methoxypyridin-2-yl)-2-oxoethyl)-5-methylindolin-2-one;
5,7-dichloro-3-hydroxy-3-(2-(6-methoxypyridin-2-yl)-2-oxoethyl)-1-propylindolin-2-one;
3-(2-(1H-indol-3-yl)-2-oxoethyl)-5-chloro-3-hydroxy-1-propylindolin-2-one;
5-chloro-3-hydroxy-1-isobutyl-3-(2-oxo-2-(pyridin-2-yl)ethyl)indolin-2-one;
1-ethyl-5-methyl-2-oxo-3-(3,4,5-trimethoxybenzyl)indolin-3-yl benzoate;
1-ethyl-3-hydroxy-5-methyl-3-(3,4,5-trimethoxybenzyl)indolin-2-one;
5-chloro-1-isobutyl-2-oxo-3-(3,4,5-trimethoxybenzyl)indolin-3-yl benzoate;
1-isobutyl-5-methyl-2-oxo-3-(3,4,5-trimethoxybenzyl)indolin-3-yl benzoate;
3-hydroxy-1-isobutyl-5-methyl-3-(3,4,5-trimethoxybenzyl)indolin-2-one;
3-(3,5-dimethoxybenzyl)-1-ethyl-5-methyl-2-oxoindolin-3-yl benzoate;
3-(3,5-dimethoxybenzyl)-5-methyl-2-oxo-1-phenethylindolin-3-yl benzoate;
5-chloro-1-ethyl-3-(3-methoxybenzyl)-2-oxoindolin-3-yl benzoate;
1-butyl-5-chloro-3-(3,5-dimethoxybenzyl)-3-hydroxyindolin-2-one;
1-butyl-5-chloro-3-hydroxy-3-(3-methoxybenzyl)indolin-2-one;
3-hydroxy-3-(3-methoxybenzyl)-5-methyl-1-propylindolin-2-one;
3-(3,4-dimethoxybenzyl)-5-methyl-2-oxo-1-phenethylindolin-3-yl benzoate;
3-(3,4-dimethoxybenzyl)-1-isopentyl-2-oxoindolin-3-yl benzoate;
3-(3,4-dimethoxybenzyl)-1-isopentyl-5-methyl-2-oxoindolin-3-yl benzoate;
3-(3,4-dimethoxybenzyl)-5-methyl-2-oxo-1-propylindolin-3-yl benzoate;
3-hydroxy-1-isobutyl-3-(3,4,5-trimethoxybenzyl)indolin-2-one;
1-isobutyl-2-oxo-3-(3,4,5-trimethoxybenzyl)indolin-3-yl benzoate;
5-chloro-2-oxo-1-phenethyl-3-(3,4,5-trimethoxybenzyl)indolin-3-yl benzoate;
1-ethyl-3-hydroxy-3-(4-methoxybenzyl)-5-methylindolin-2-one;
3-(2-hydroxy-4-methoxybenzyl)-2-oxo-1-propylindolin-3-yl benzoate;
3-(2-hydroxy-4-methoxybenzyl)-5-methyl-1-(4-methylpentyl)-2-oxoindolin-3-yl benzoate;
3-(2-hydroxy-5-methoxybenzyl)-1-isobutyl-2-oxoindolin-3-yl benzoate;
5-chloro-3-(2-hydroxy-3-methoxybenzyl)-1-isopentyl-2-oxoindolin-3-yl benzoate;
5-chloro-3-(2-hydroxy-4-methoxybenzyl)-1-(3-morpholinopropyl)-2-oxoindolin-3-yl benzoate;
1-ethyl-3-(2-hydroxy-4-methoxybenzyl)-2-oxoindolin-3-yl benzoate;
3-(2-hydroxy-5-methoxybenzyl)-5-methyl-1-(4-methylpentyl)-2-oxoindolin-3-yl benzoate;
5-chloro-1-ethyl-3-(2-hydroxy-3-methoxybenzyl)-2-oxoindolin-3-yl benzoate;
1-ethyl-3-(2-hydroxy-5-methoxybenzyl)-5-methyl-2-oxoindolin-3-yl benzoate;
5-chloro-3-(2-hydroxy-5-methoxybenzyl)-2-oxo-1-phenethylindolin-3-yl benzoate;
5-chloro-1-ethyl-3-(2-hydroxy-5-methoxybenzyl)-2-oxoindolin-3-yl benzoate;
3-((1H-indol-3-yl)methyl)-5-chloro-2-oxo-1-propylindolin-3-yl benzoate;
3-((1-benzoyl-1H-indol-3-yl)methyl)-3-hydroxy-5-methyl-1-propylindolin-2-one; or
3-(1H-indol-3-yl)methyl)-1-butyl-2-oxoindolin-3-yl benzoate.

In a further embodiment of the invention, provided is a pharmaceutical composition, comprising a therapeutically effective amount of a compound according to formula (I) or a pharmaceutically acceptable salt thereof and a pharmaceutically acceptable carrier.

In a still further embodiment of the invention, provided is a method for treating a degenerative disease or disorder, comprising the step of administering a therapeutically effective amount of a compound according to claim 1 or a pharmaceutically acceptable salt thereof and a pharmaceutically acceptable carrier to a patient in need thereof.

In a yet still another embodiment of the invention, provided is a method for treating a degenerative disease or disorder, comprising the step of administering a therapeutically effective amount of a compound according to claim 1 or a pharmaceutically acceptable salt thereof and a pharmaceutically acceptable carrier to a patient in need thereof. In one embodiment, the degenerative disease or disorder is retinitis pigmentosa.

In a yet still further embodiment of the invention, provided is a method of treating a retinal degenerative disease, comprising the step of administering a therapeutically effective amount of a compound according to formula (I) or a pharmaceutically acceptable salt thereof and a pharmaceutically acceptable carrier to a patient in need thereof.

In another embodiment of the invention, provided is a method for preventing calcium-induced or oxidant-induced mitochondrial damage preventing or loss of mitochondrial respiratory capacity in a cell susceptible thereof wherein the calcium-induced or oxidant-induced mitochondrial damage or loss of mitochondrial respiratory capacity comprises excess of cGMP that increases the number of cGMP-gated cation channels in an open configuration, allowing an influx of Ca2+ into the cell, said method comprising contacting the cell with an effective amount of a compound or a pharmaceutically acceptable salt thereof according to formula (I).

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount".

For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

The compounds of formula I can be prepared according to the following schemes:

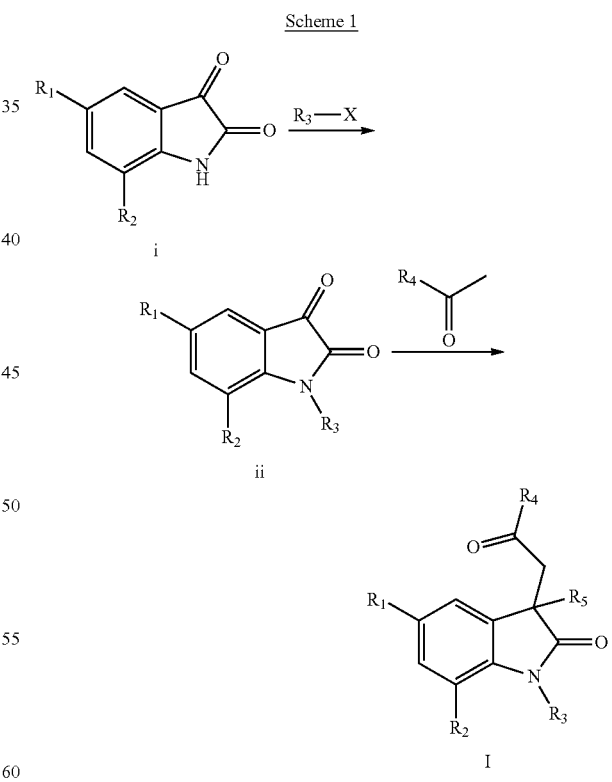

As shown in Scheme 1, compounds of formula (I) can be made by reacting the starting isatin (i), having the substitution pattern of $R_1$ and $R_2$, where $R_1$ and $R_2$ can be, for example, hydrogen, alkyl, methyl, ethyl, chloro-, bromo-, iodo, or any alkyl or halide and may be purchased from common commercial vendors (such as Fisher Scientific, VWR, Aldrich, Ryan Scientific), with R$_3$—X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. R$_3$ may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), (piperidin-1-yl)ethyl, phenethyl, or any other common make up of a hydrocarbon chain. This reaction may be carried out in anhydrous acetonitrile or anhydrous N,N-dimethyl formamide (purchased from commercial sources). In the case of intermediate ii where R$_3$ is pent-4-yn-1-yl, a separate reaction can be performed to prepare the necessary leaving group X. This may be done by converting the commercially available pent-4-yn-1-ol into pent-4-yn-1-yl 4-methylbenzenesulfonate using commercially available tosyl chloride under basic conditions (e.g., triethyl amine) in a solvent such as dichloromethane. Compounds of formula I may be made by reacting intermediate ii with any ketone in the presence of an amine base such as diethyl amine, dimethyl amine, di-isopropyl amine, proline, or any substitution therein. R$_4$ may be, for example, hydrogen, aryl, phenyl, indolin, 2-pyridinyl, 2-pyridyl, 6-methoxypyridin-2-yl, 2,6-dimethoxypyridin-3-yl, 6-ethynylpyridin-2-yl, or any other aromatic derivative therein. R$_5$ may be, for example, hydroxyl, amine, hydrogen, benzoate, methyl carbonate or tert-butyl carbonate. This is made in a similar way to a protocols outlined in Allu, Suresh et al., Tetrahedron Letters (2011), 52(32), 4080-4083; Pandeya, S. et al., Acta Ciencia Indica, Chemistry (2007), 33(4), 549-561; Macaev, F. Z. et al., Chemistry of Heterocyclic Compounds (New York, N.Y., United States) (2007), 43(3), 298-305; and Lopez-Alvarado, Pilar and Avendano, Carmen Synthesis (2002), (1), 104-110.

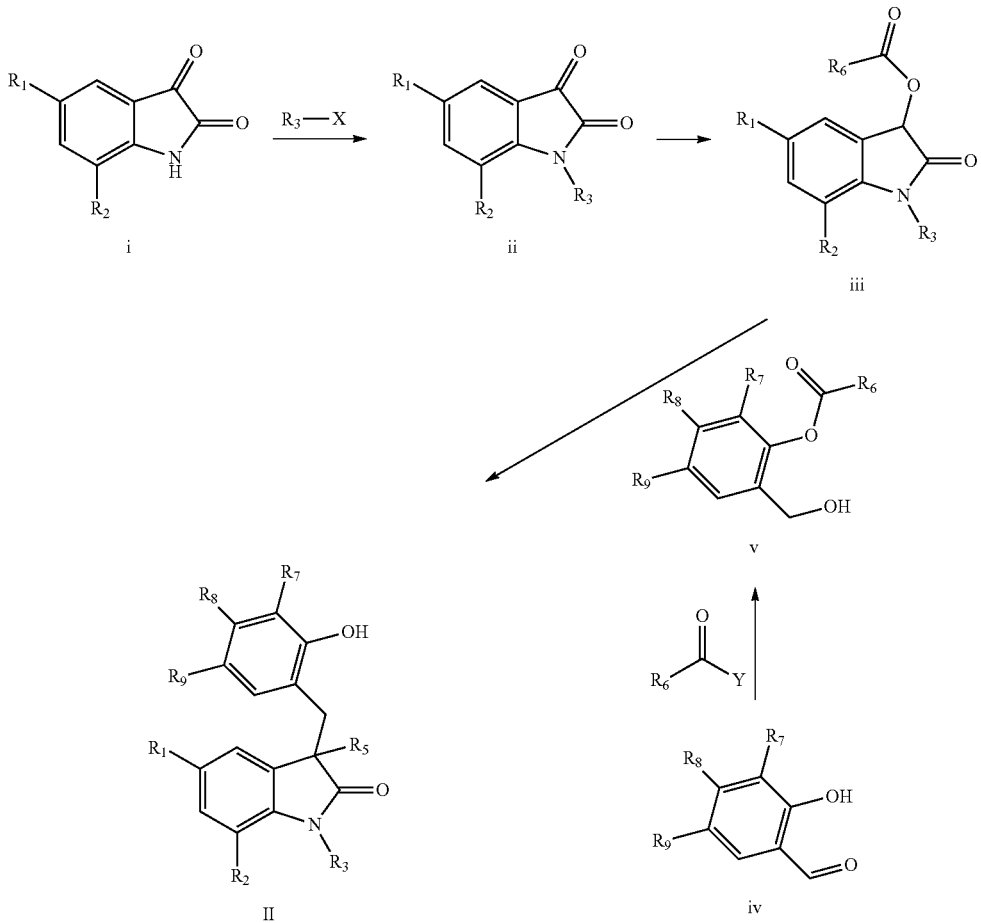

Scheme 2

As shown in Scheme 2, compounds of formula II may be made by reacting the starting isatin (i), having the substitution pattern of R$_1$ and R$_2$ that may be, for example, hydrogen, alkyl, methyl, ethyl, chloro-, bromo-, iodo, or any other alkyl or halide and may be purchased from common commercial vendors, with R$_3$—X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. R$_3$ may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1

20091119), (piperidin-1-yl)ethyl, phenethyl, or any other common make up of a hydrocarbon chain. In the case of, pent-4-yn-1-yl for intermediate ii, a separate reaction can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., NaBH$_4$, BH$_3$, DIBAL) and its subsequent protection where R$_6$ may, for example, methyl, isobutyl, tert-butyl, phenyl, methyl ether, ethyl ether, dimethyl amine, or any other ether, poly substituted amine, alkyl or aryl group. This protection may be done under basic condition (e.g., NEt$_3$, DIPEA, DMAP) in solvents like anhydrous dichloromethane (purchased from Fisher Scientific stored under 4 angstrom molecular sieves) or anhydrous THF (purchased from common vendors). Compound of formula II may be made by reacting intermediate iii with intermediate v. Intermediate v can be made from intermediate iv. Intermediate iv can be commercially available variants on the benzaldehyde backbone where R$_7$, R$_8$, and R$_9$ may be, for example, hydrogen, methyl ether, alkyl ether, or derivative therein. Protection of the phenolic motif of intermediate iv may be done under basic conditions (e.g., NaH, NEt$_3$, DMAP, DIPEA) that can result in a formate where R$_6$ may be, for example, alkyl, methyl, isopropyl, phenyl, t-butyl, oxy-methyl, or oxy-tertbutyl that are derived from commercial sources. Y may be, for example, chloride, bromide, or tertbutyl carbonate. Reduction of the aldehyde to afford intermediate iv may be done using common reducing regents such as NaBH$_4$, DIBAL, BH$_3$ or any other common reducing agent. The reaction may occur in THF/water mixtures to afford intermediate v. Compounds of formula II may be made by reacting the intermediate iii with a strong base (e.g., LiHMDS, KHMDS, LDA) followed by exposure to intermediate v. This reaction may take place in solvents like THF, toluene, and DMF.

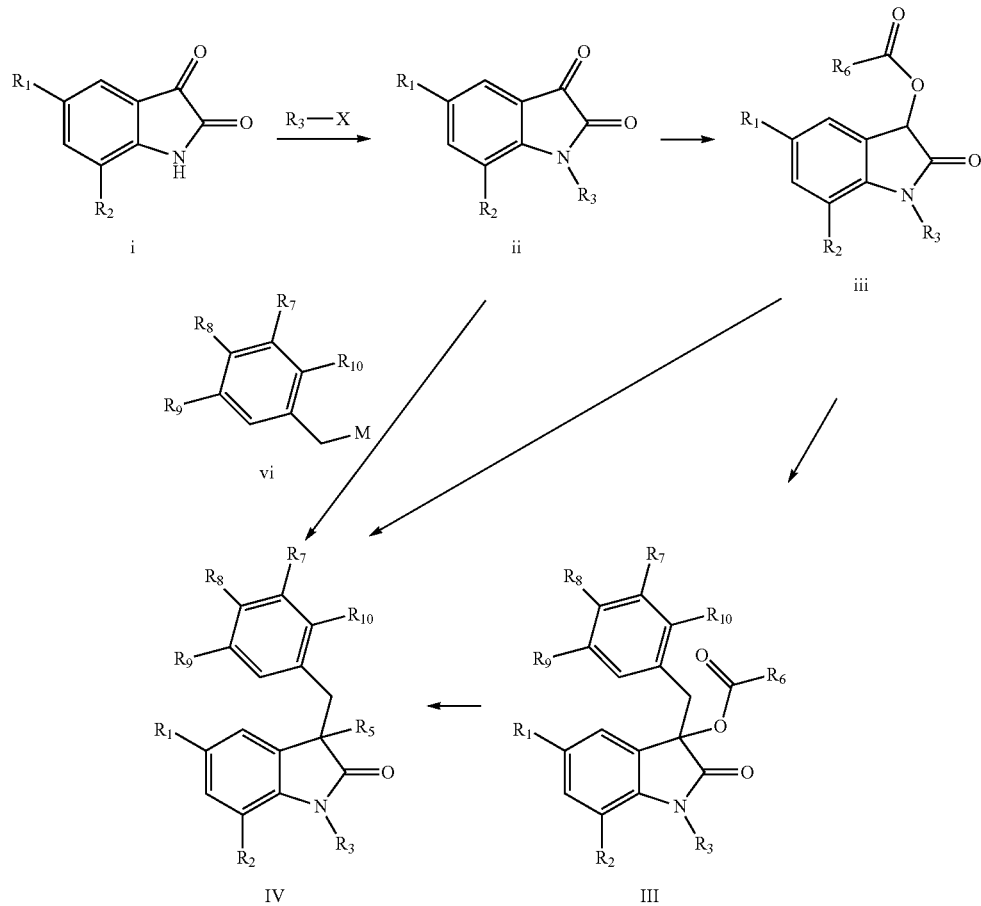

Scheme 3

According to Scheme 3, compounds of formula III may be made in the following manner: reacting the starting isatin (i), having the substitution pattern of R$_1$ and R$_2$ that may be, for example, hydrogen, alkyl, methyl, ethyl, chloro-, bromo-, iodo, or any other alkyl or halide and may be purchased from common commercial vendors, with R$_3$—X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. R$_3$ may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), piperidin-1-yl)ethyl, phenethyl, or any other common make up of a hydrocarbon chain. In the case of pent-4-yn-1-yl for intermediate ii, a separate reaction can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., $NaBH_4$, $BH_3$, DIBAL) and its subsequent protection where $R_6$ may be, for example, methyl, isobutyl, tert-butyl, phenyl, methyl ether, ethyl ether, dimethyl amine, or any other ether, poly substituted amine, alkyl or aryl group. This reaction may be done under basic condition (e.g., $NEt_3$ DIPEA, DMAP) in solvents like anhydrous dichloromethane (purchased from Fisher Scientific stored under 4 angstrom molecular sieves). Intermediate iii can then be reacted with a base, like LiHMDS, and combined with commercially available (from, for example, Fisher Scientific or Aldrich) benzylic halides (e.g., 2-methoxyl benzyl chloride, 3-methoxy benzyl chloride, 4-methoxy benzyl chloride, 3,4,5-trimethoxy benzyl chloride, 3,5 dimethoxy benzyl bromide) to form final compound III. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using $PBr_3$ in a solvent like anhydrous dichloromethane.

Compound of formula IV may be made by reacting intermediate iii with any commercial benzylic halide. Intermediate iii may be made by reducing intermediate ii using common reducing agents (e.g., $NaBH_4$, $BH_3$, DIBAL) and its subsequent protection where $R_6$ may be, for example, methyl, isobutyl, tert-butyl, phenyl, methyl ether, ethyl ether, dimethyl amine, or any other ether, poly substituted amine, alkyl or aryl group. This reaction may be done under basic condition (e.g., $NEt_3$ DIPEA, DMAP) in solvents like anhydrous dichloromethane (purchased from Fisher Scientific stored under 4 angstrom molecular sieves). Intermediate iii can then be reacted with a base, like LiHMDS, and combined with commercially available (from either Fisher Scientific or Aldrich) benzylic halides (e.g., 2-methoxyl benzyl chloride, 3-methoxy benzyl chloride, 4-methoxy benzyl chloride, 3,4,5-trimethoxy benzyl chloride, 3,5 dimethoxy benzyl bromide) to form final compound III where $R_7$, $R_8$, $R_9$, and $R_{10}$ may be, for example, hydrogen, methyl ether, halide, or any multiple or derivative therein. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using $PBr_3$. This type of transformation may also be accomplished using triphenylphosphine any carbontetrahalide in a solvent such as anhydrous dichloromethane (commercially available from common sources).

Compounds of formula IV can also be made by the reaction of compounds of formula III under basic conditions (e.g., using potassium hydroxide, sodium hydroxide, potassium carbonate, sodium carbonate) in a solvent like methanol, methanol with water, ethanol, ethanol with water, or water. This reaction may be accelerated by the use of a microwave or other conventional heating or refluxing. This may form compounds of formula IV with an $R_5$ substitution.

Compounds of formula IV may also be made by the exposure of compound III to a common reducing agent (e.g., $NaBH_4$), or organometallic (alkyl Grignard or alkyl lithium) using a common anhydrous solvent like THF.

Compounds of formula IV may also be made by forming the Grignard or any other organometallic reagent from using intermediate vi. Intermediate vi may be made from commercially available benzylic halides (e.g., 2-methoxy benzyl chloride, 3-methoxy benzyl chloride, 4-methoxy benzyl chloride, 3,4,5-trimethoxy benzyl chloride, 3,5 dimethoxy benzyl bromide). M may be lithium, magnesium chloride, magnesium bromide, magnesium iodide, sodium or any other metallic reagent to form final compound III where $R_7$, $R_8$, $R_9$, and $R_{10}$ may be, for example, hydrogen, methyl ether, halide, or any multiple or derivative therein. In some cases, 3,4 dimethoxy benzyl bromide may be used. For these instances, conversion of the commercially available 3,4 dimethoxy benzyl alcohol purchased from Fisher Scientific, to the corresponding benzyl bromide may be done using PBr3.

Scheme 4

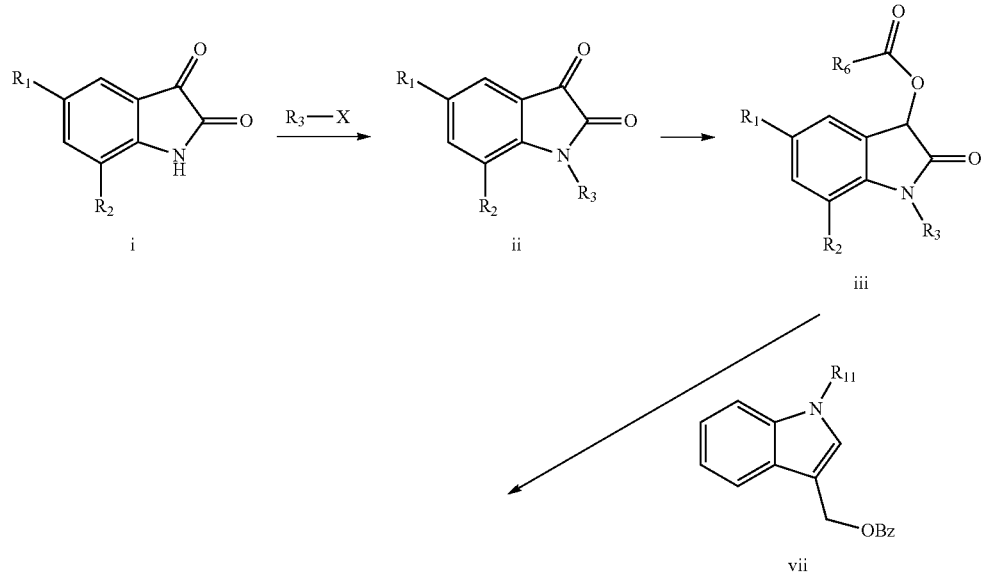

-continued

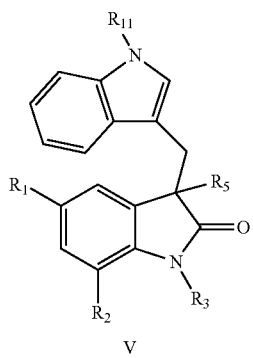

V

As seen in Scheme 4, compounds of formula V may be made by reacting the starting isatin (i), having the substitution pattern of $R_1$ and $R_2$ that may be, for example, hydrogen, alkyl, methyl, ethyl, chloro-, bromo-, iodo, or any other alkyl or halide and may be purchased from common commercial vendors, with $R_3$—X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. $R_3$ may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), (piperidin-1-yl)ethyl, phenethyl, or any other common make up of a hydrocarbon chain. In the case of pent-4-yn-1-yl for intermediate ii, a separate reaction can be performed to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate iii may be made by reducing intermediate ii using common reducing agents (e.g., $NaBH_4$, $BH_3$, DIBAL) and its subsequent protection where $R_6$ may be, for example, methyl, isobutyl, tert-butyl, phenyl, methyl ether, ethyl ether, dimethyl amine, or any other ether, poly substituted amine, alkyl or aryl group. This reaction may be done under basic condition (e.g., $NEt_3$, DIPEA, DMAP) in solvents like anhydrous dichloromethane (purchased from Fisher Scientific stored under 4 angstrom molecular sieves). Intermediate vii may be made by reacting commercially available (1H-indol-3-yl)methanol with benzoyl chloride in the presence of triethyl amine and N,N-dimethyl aminepyridine to afford a product where $R_{11}$ may be, for example, hydrogen or the corresponding benzamide (PhCO). This reaction may take place in a solvent such as anhydrous dichloromethane. Intermediate iii can then be reacted with a base, like LiHMDS or KHMDS with intermediate vii to form compounds of formula V. This reaction may occur in solvents like toluene and DMF.

Scheme 5

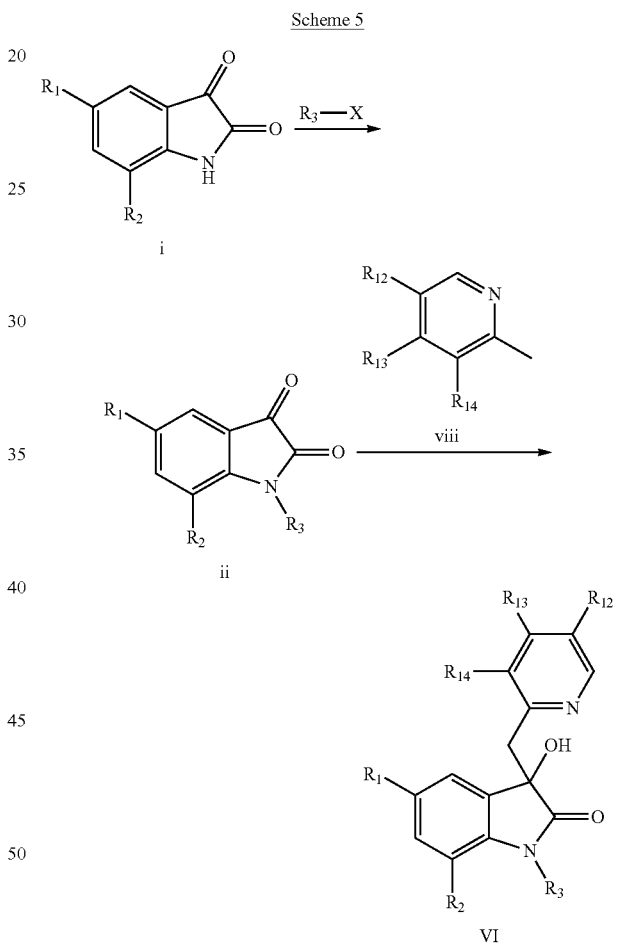

As shown in Scheme 5, compounds of formula VI may be made by reacting the starting isatin (i), having the substitution pattern of $R_1$ and $R_2$ that may be, for example, hydrogen, alkyl, methyl, ethyl, chloro-, bromo-, iodo, or any other alkyl or halide and may be purchased from common commercial vendors, with $R_3$—X under basic conditions such as potassium carbonate, sodium carbonate, sodium hydride, potassium hydroxide, sodium hydroxide in the presence of a catalytic quantity of sodium iodide, potassium iodide, or any inorganic salt that may facilitate this transformation. This reaction may be carried out in anhydrous acetonitrile or anhydrous N,N-dimethyl formamide. $R_3$ may be, for example, alkyl, ethyl, propyl, isopropyl, n-butyl, isobutyl, n-pentyl, isopentyl, isohexyl, 3-azidopropyl, pent-4-yn-1-yl, 3-morpholinopropyl (see Sun, Connie L.; Li, Xiaoyuan; Zhu, Yan From PCT Int. Appl. (2009), WO 2009139834 A1 20091119), (piperidin-1-yl)ethyl, phenethyl, or any other common make up of a hydrocarbon chain. In the case of pent-4-yn-1-yl for intermediate ii, a separate reaction must occur to prepare the necessary leaving group X. This may be done by converting the commonly commercially available pent-4-yn-1-ol into pent-4-yn-1-yl 4-methylbenzenesulfonate using commercially available tosyl chloride under basic conditions (e.g., triethyl amine) in a solvent such as dichloromethane. Intermediate of formulation viii may be purchased from most common commercial sources where $R_{12}$, $R_{13}$, and $R_{14}$ can be, for example, hydrogen, hydroxyl, methyl ether, or any alkyl ether. In the instances where the desired substitution of $R_{12}$, $R_{13}$, or $R_{14}$ are not commercially available, a suitable alkylation can be done using a base like potassium tert-butoxide in a solvent like THF at the appropriate temperature as shown in Tung, Yen-Shih, et al. Journal of Medicinal Chemistry (2011), 54(8), 3076-3080. Compounds of formula VI may then be made by first deprotonating the intermediate viii using a base like LDA, KHMDS, or LiHMDS and combining it with intermediate ii. This reaction may be run in solvents like toluene, DMF, or THF. An alternate method to form VI can be done using intermediates ii and viii with the protocol outlined in Rui Niu, Jian Xiao, Tao Liang, and Xingwei Li *Org. Lett.*, 2012, 14 (3), 676-679.

The invention will now be further described in the Examples below, which are intended as an illustration only and do not limit the scope of the invention.

EXAMPLES

I. Preparation of Certain Intermediates of the Invention 1-propylindoline-2,3-dione

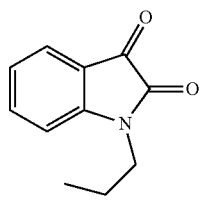

To an oven dried flask equipped with a stir bar cooled under argon was added isatin (2.0 grams, 13.6 mmol, 1.0 equiv., purchased from Fisher Scientific), potassium carbonate (9.67 grams, 5.0 equiv.), and sodium iodide (0.209 grams, 1.4 mmol, 0.1 equiv.). The mixture was taken up in acetonitrile (60.0 μL, stored over 4 angstrom molecular sieves). While stirring at room temperature the appropriate propyl bromide (1.4 mL, 15 mmol, 1.1 equiv.) was added. After five days of stirring at room temperature, the solution was filtered, concentrated, and taken up in dichloromethane. The solution was next filtered again, and concentrated. Purification was done on a silica gel column using hexanes/ethyl acetate, to afford a red solid, 1.5 grams (60% yield). 1H-NMR δ 7.59 (m, 2H), 7.12 (dd, 1H), 6.90 (d, 1H), 3.70 (t, 2H), 1.75 (m, 2H), 1.00 (t, 3H).

Alternative N-alkylation procedure: To an oven dried flask equipped with a stir bar cooled under argon was added the isatin (1.0 equiv.), potassium carbonate (1.5 equiv.), and potassium iodide (0.1 equiv.). The mixture was taken up in DMF (0.2 M based on the isatin). While stirring at room temperature the appropriate alkyl halide or alkyl tosylate (1.3 equiv.) was added. The mixture was then heated to 60° C. and stirred at this temperature overnight. The next day the solution was filtered, concentrated, and taken up in dichloromethane. The solution was next filtered again, and concentrated. Purification was done on a silica gel column using either hexanes/ethyl acetate or dichloromethane/methanol.

Second Alternative N-alkylation: To an oven dried Biotage microwave vial equipped with a stir bar that was cooled under argon was added the isatin (1.0 equiv.), potassium carbonate (1.3 equiv.), and potassium iodide (0.1 equiv.). The mixture was taken up in DMF (0.1 M based on isatin). The mixture was then heated to 100° C. in a Biotage initiator microwave set to a high absorbance level, for one hour. It was then cooled to room temperature, filtered, concentrated, and taken up in dichloromethane. The solution was next filtered again, and concentrated. Purification was done on a silica gel column using either hexanes/ethyl acetate or dichloromethane/methanol.

1-isopentyl-5-methylindoline-2,3-dione

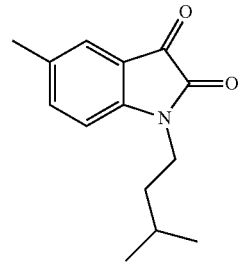 [SMILES: Cc1ccc2c(c1)C(=O)C(=O)N2CCC(C)C]

Made in an analogous fashion to 1-propylindoline-2,3-dione using commercially available 5-methyl isatin (purchased from Fisher Scientific) and 1-bromo-3-methylbutane (purchased from Fisher Scientific). 1H NMR δ 7.41 (m, 2H), 6.78 (d, 1H), 3.71 (t, 2H), 2.33 (s, 3H), 1.57 (m, 3H), 0.99 (d, 6H).

5-methoxy-2-methylpyridine

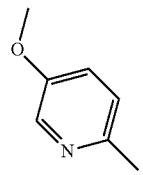

Was synthesized according to the procedures in Tung, Yen-Shih, et al. Journal of Medicinal Chemistry (2011), 54(8), 3076-3080.

3-methoxy-2-methylpyridine

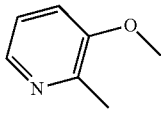

Was prepared in a similar manner to 5-methoxy-2-methylpyridine using 3-hydroxy-2-methylpyridine (purchased from Fisher Scientific) and methyl iodide (purchased from Fisher Scientific).

5-chloro-1-ethylindoline-2,3-dione

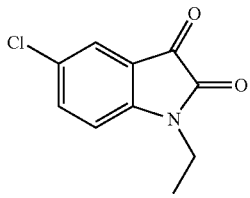

Was made in an analogous fashion to 1-propylindoline-2,3-dione using commercially available 5-chloro isatin and ethyl bromide, both purchased from Fisher Scientific. 1H NMR δ 7.58 (m, 2H), 6.88 (d, 1H), 3.80 (q, 2H), 1.31 (t, 3H).

5-chloro-1-phenethylindoline-2,3-dione

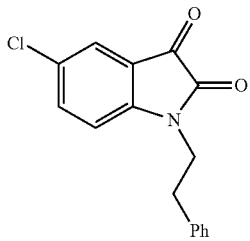 [SMILES: O=C1C(=O)N(CCc2ccccc2)c2ccc(Cl)cc21]

Was prepared in an analogous manner to 1-propylindoline-2,3-dione using the commercially available 5-chloroisatin (purchased from Fisher Scientific) and 2-phenethyl bromide (purchased from Fisher scientific). 1H NMR δ 7.54 (s, 1H), 7.44 (d, 1H), 7.27 (m, 5H), 6.64 (d, 1H), 3.95 (t, 2H), 2.99 (t, 2H).

1-isopentylindoline-2,3-dione

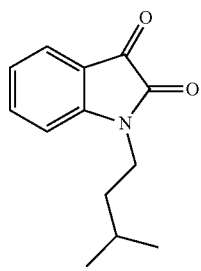 [SMILES: CC(C)CCN1C(=O)C(=O)c2ccccc21]

Was prepared in an analogous manner to 1-propylindoline-2,3-dione using commercially available isatin (purchased from Fisher Scientific) and 1-bromo-3-methyl butane (purchased from Fisher Scientific). 1H NMR δ 7.58 (m, 2H), 7.10 (t, 1H), 6.89 (d, 1H), 3.73 (t, 2H), 1.58 (m, 3H), 1.00 (d, 6H).

5-chloro-1-(2-(piperidin-1-yl)ethyl)indoline-2,3-dione

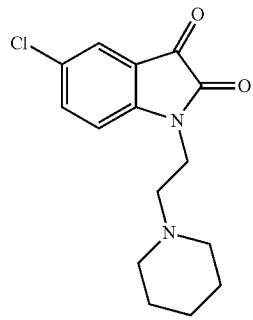 [SMILES: O=C1C(=O)N(CCN2CCCCC2)c2ccc(Cl)cc21]

Was prepared in an analogous manner to 1-propylindoline-2,3-dione using commercially available 5-chloroisatin (purchased from Fisher Scientific) and 1-(2-bromoethyl)piperidine (purchased from Fisher Scientific). 1H-NMR δ 7.55 (m, 2H), 6.95 (d, 1H), 3.84 (t, 2H), 2.58 (t, 2H), 2.46 (bs, 4H), 1.54 (m, 4H), 1.43 (m, 2H).

5-chloro-1-propylindoline-2,3-dione

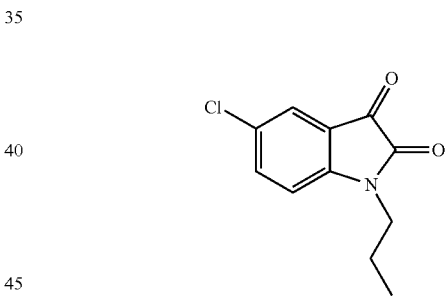

Was prepared in an analogous manner to 1-propylindoline-2,3-dione using commercially available 5-chloroisatin (purchased from Fisher Scientific) and 1-bromo-propane (purchased from Fisher Scientific). 1H NMR δ 7.57 (m, 2H), 6.88 (d, 1H), 3.69 (t, 2H), 1.74 (m, 2H), 1.00 (t, 3H)

5-methyl-1-propylindoline-2,3-dione

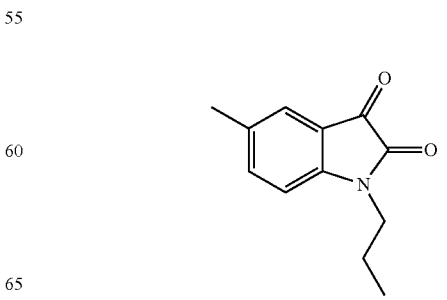

Was prepared in an analogous manner to 1-propylindoline-2,3-dione using 5-methyl isatin (purchased from Fisher Scientific) and 1-bromo-propane (purchase from Fisher Scientific). 1H NMR δ 7.41 (m, 2H), 6.80 (d, 1H), 3.67 (t, 2H), 2.33 (s, 3H), 1.72 (m, 2H), 0.99 (t, 3H).

1-ethyl-5-methylindoline-2,3-dione

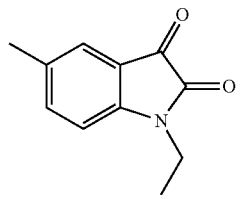

Was prepared in an analogous manner to 1-propylindoline-2,3-dione using commercially available 5-methyl isatin (purchased from Fisher Scientific) and ethyl bromide (purchased from Fisher Scientific). 1H-NMR δ 7.42-7.38 (m, 2H), 6.80 (d, 1H), 3.77 (q, 2H), 2.34 (s, 3H), 1.31 (t, 3H).

5-methyl-1-phenethylindoline-2,3-dione

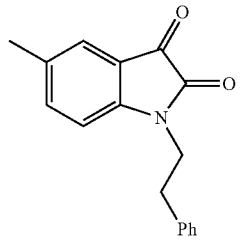 [SMILES: Cc1ccc2c(c1)C(=O)C(=O)N2CCc1ccccc1]

Was prepared in an analogous manner to 1-propylindoline-2,3-dione using 5-methyl isatin (purchased from Fisher Scientific) and 2-phenethyl bromide (purchased from Fisher Scientific). 1H NMR δ 7.40 (s, 1H), 7.29 (m, 6H), 6.66 (d, 1H), 3.93 (t, 2H), 2.99 (t, 2H), 2.32 (s, 3H).

1-isobutylindoline-2,3-dione

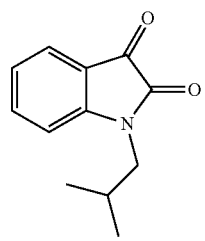

Was prepared in an analogous manner to 1-propylindoline-2,3-dione using isatin (purchased from Fisher Scientific) and 1-bromo-2-methyl propane (purchased from Fisher Scientific). 1H NMR δ (dd, 2H), 7.13 (t, 1H), 6.90 (d, 1H), 3.55 (d, 2H), 2.16 (m, 1H), 1.00 (d, 6H).

1-butylindoline-2,3-dione

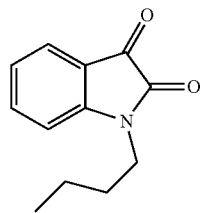

Was made in an analogous fashion to 1-propylindoline-2,3-dione by reacting commercially available isatin (purchased from Fisher Scientific) with 1-bromo-butane (purchased from Fisher Scientific). 1H-NMR δ 7.68 (m, 2H), 7.11 (dd, 1H), 6.90 (d, 1H), 3.72 (t, 2H), 1.65 (q, 2H), 1.41 (m, 2H), 0.97 (t, 3H).

5-methyl-1-(pent-4-yn-1-yl)indoline-2,3-dione

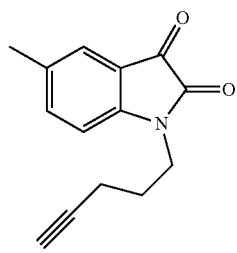 [SMILES: C#CCCCN1C(=O)C(=O)c2cc(C)ccc21]

To a flame dried flask cooled under argon was added pent-4-yn-1-yl 4-methylbenzenesulfonate (0.325 grams, 1.37 mmol) 5-methylindoline-2,3-dione (0.2 grams, 1.24 mmol) potassium carbonate (0.514 grams, 3.72 mmol) sodium iodide (0.187 grams, 1.24 mmol) and taken up in 12 mL of DMF. The reaction was stirred at room temperature overnight. The next day it was filtered and concentrated. The residue was taken up in dichloromethane, filtered again, and concentrated. Purification was done using a on silica support using a hexanes/ethyl acetate (8:2). Yield, 70% 1H-NMR δ 7.41 (m, 2H), 6.90 (d, 1H), 3.84 (t, 2H), 2.35 (s, 3H), 2.32 (td, 2H), 2.05 (t, 1H), 1.94 (m, 2H).

5-chloro-1-isobutylindoline-2,3-dione

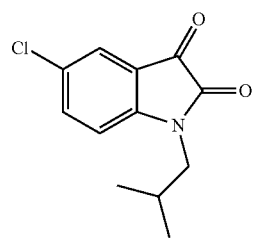 [SMILES: CC(C)CN1C(=O)C(=O)c2cc(Cl)ccc21]

Was made in an analogous fashion to 1-propylindoline-2,3-dione from commercially available 5-chloroisatin (purchased from Fisher Scientific) and 1-bromo-2methylpropane (purchased from Fisher Scientific). 1H NMR δ 7.57 (m, 2H), 6.87 (d, 1H), 3.54 (d, 2H), 2.12 (m, 1H), 1.00 (d, 6H).

1-isobutyl-5-methylindoline-2,3-dione

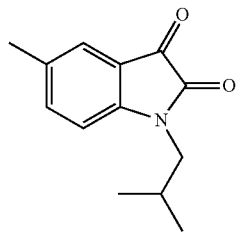 [SMILES: Cc1ccc2c(c1)C(=O)C(=O)N2CC(C)C]

Was made in an analogous fashion to 1-propylindoline-2,3-dione using 5-methyl isatin (purchased from Fisher Scientific) and 1-bromo-2-methyl propane (purchased from Fisher Scientific). 1H NMR δ 7.42 (m, 2H), 6.79 (d, 1H), 3.52 (d, 2H), 2.33 (s, 3H), 2.08 (m, 1H), 0.99 (d, 6H).

5,7-dichloro-1-propylindoline-2,3-dione

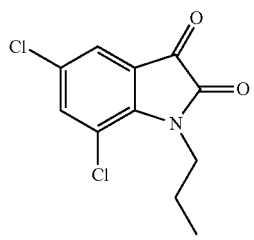 [SMILES: CCCN1C(=O)C(=O)c2cc(Cl)cc(Cl)c21]

Was made in an analogous fashion to 1-propylindoline-2,3-dione using 5,7-dichloroisatin (purchased from Fisher Scientific) and 1-bromopropane (purchased from Fisher Scientific). 1H NMR δ 7.53 (d, 1H), 7.51 (d, 1H), 4.05 (t, 2H), 1.78 (m, 2H), 0.99 (t, 3H).

1-ethyl-5-methyl-2-oxoindolin-3-yl benzoate

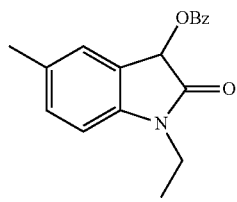

To a dry clean round bottom equipped with a stir bar was added N-ethyl-5-methyl-isatin (0.7 gram, 3.7 mmol) followed by 12 mL of methanol. Once all of the material had dissolved, while stirring at room temperature solid sodium borohydride (0.154 grams, 4.07 mmol, purchased from Fisher Scientific) was added. After all the color had disappeared (approximately one to two minutes), the reaction was quenched with NH4Cl (saturated). The solution was concentrated, via a Buchi rotovap, to approximately half the volume, then the organic material was extracted with ethyl acetate. The aqueous layer was salted out using sodium chloride and washed two more times with ethyl acetate. The combined organic solution was dried with sodium sulfate, filtered and concentrated. It was then used in the subsequent step without further purification.

To a flame dried flask cooled under argon was added the crude alcohol (3.7 mmol) and 4-N,N dimethylaminopyridine (DMAP) (0.047 grams, 0.39 mmol). This was taken up in 20.0 mL of dichloromethane (dried over 4 angstrom molecular sieves). While stirring at room temperature triethylamine (0.82 mL, 5.99 mmol, purchased from Aldrich) was added followed by benzoyl chloride (0.51 mL, 4.39 mmol, purchased from Aldrich). The reaction stirred at room temperature until all of the starting material had been consumed. Once complete, the reaction was diluted with water, and the two layers separated. The aqueous layer was washed with dichloromethane twice. The combined organic solution was dried with sodium sulfate, filtered, and concentrated. Chromatography using a Teledyne ISCO on a silica support (Hexanes/Ethyl acetate gradient) afforded the desired compound. Yield, 65% for the two steps. 1H-NMR δ 8.13 (d, 2H), 7.62 (t, 1H), 7.46 m (t, 2H), 7.27 (s, 1H), 7.17 (dd, 1H), 6.82 (d, 1H), 6.18 (s, 1H), 3.83 (m, 2H), 2.33 (s, 3H), 1.35 (t, 3H).

4-(bromomethyl)-1,2-dimethoxybenzene

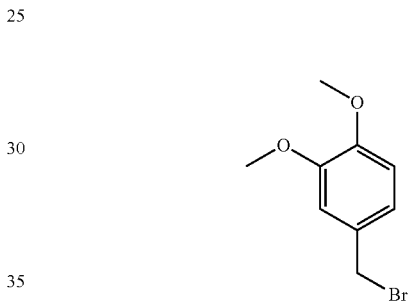

To a flame dried flask cooled under argon was added (3,4-dimethoxyphenyl)methanol (0.169 grams, 1.0 mmol, 1.0M in dichloromethane, stored over 4 angstrom molecular sieves, purchased from Fisher Scientific). While stirring at room temperature a solution of phosphorous tribromide (1.4 mL, 1.0M in dichloromethane, purchased from Fisher Scientific) was added slowly. Once complete, the reaction was diluted with water and the organic layer removed. The aqueous layer was washed twice more with dichloromethane, and the organic material combined. The organic material was next washed with aqueous sodium bicarbonate (saturated), dried with sodium sulfate, filtered and concentrated. Purification was done using a Teledyne ISCO on a silica support using a hexanes ethyl acetate gradient. Yield 65%. 1H NMR δ 6.96 (dd, 1H), 6.92 (d, 1H), 6.82 (d, 1H), 4.52 (s, 2H), 3.91 (s, 3H), 3.89 (s, 3H).

Alternative route for making polymethoxy variants: To a flame dried flask cooled under argon equipped with a stir bar and reflux condenser is added the 3,4,5 trimethoxybenzyl chloride (from Aldrich), or 3,5 dimethoxy benzyl bromide (from Fisher Scientific), or 3-methoxybenzyl chloride (from Fisher Scientific), or 4-methoxy benzyl chloride (from Fisher Scientific), or 4-(bromomethyl)-1,2-dimethoxybenzene, or any benzyl chloride derived therein (1.0 equiv.) and magnesium turnings (1.1 equiv.). This is taken up in a small amount of dry THF (purchased from Aldrich). 1,2 dibromo ethane (0.1 equiv.) is added and the solution stirred vigorously until heat is given off. Once the solution has cooled to room temperature it is diluted to afford a 1.0 M solution of the newly formed Grignard reagent.

To an oven dried flask equipped with a stir bar is added the appropriate N-alkylated isatin (1.0 equiv., 0.2 M in THF). While stirring at room temperature a solution of the afore mentioned Gringard reagent (1.75 equiv.) is added. Once the reaction is complete, it is quenched with 0.1M HCl, diluted with ethyl acetate, and the organic layer extracted. The aqueous layer is salted out using sodium chloride and two ethyl acetate washes are done. The combined organic material is dried with sodium sulfate, filtered and concentrated.

5-chloro-1-isobutyl-2-oxoindolin-3-yl benzoate

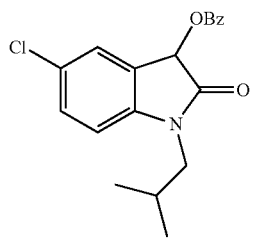

Was made in an analogous fashion to 1-ethyl-5-methyl-2-oxoindolin-3-yl benzoate using 5-chloro-1-isobutylindoline-2,3-dione. 1H NMR δ 8.11 (d, 2H), 7.60 (dd, 1H), 7.52-7.32 (m, 4H), 6.80 (d, 1H), 6.10 (s, 1H), 3.75 (m, 2H), 1.72-1.57 (m, 1H), 1.01 (dd, 6H).

1-isobutyl-5-methyl-2-oxoindolin-3-yl benzoate

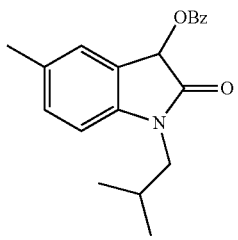

Was made in an analogous fashion to 1-ethyl-5-methyl-2-oxoindolin-3-yl benzoate using 1-isobutyl-5-methylindoline-2,3-dione. 1H-NMR δ 8.12 (d, 2H), 7.59 (t, 1H), 7.47 (t, 2H), 7.27 (s, 1H), 7.14 (d, 1H), 6.87 (d, 1H), 6.18 (s, 1H), 3.55 (m, 2H), 2.30 (s, 3H), 2.19 (m, 1H), 1.01 (dd, 6H).

5-methyl-2-oxo-1-phenethylindolin-3-yl benzoate

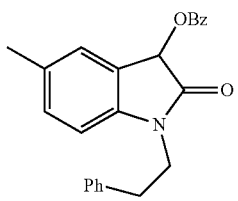

Was made in an analogous fashion to 1-ethyl-5-methyl-2-oxoindolin-3-yl benzoate using 5-methyl-1-phenethylindoline-2,3-dione. 1H NMR δ 8.11 (dd, 2H), 7.58 (dt, 1H), 7.46 (dd, 2H), 7.34-7.26 (m, 6H), 7.13 (d, 1H), 6.73 (d, 1H), 6.14 (s, 1H), 3.96 (dd, 2H), 3.03 (t, 2H), 2.31 (s, 3H).

5-chloro-1-ethyl-2-oxoindolin-3-yl benzoate

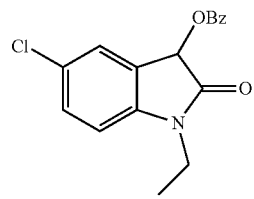

Was made in an analogous fashion to 1-ethyl-5-methyl-2-oxoindolin-3-yl benzoate using 5-chloro-1-ethylindoline-2,3-dione. 1H-NMR δ 8.11 (dd, 2H), 7.60 (dt, 1H), 7.47 (m, 2H) 7.45 (m, 1H), 7.33 (dd, 1H), 6.80 (d, 1H), 6.10 (d, 1H), 3.85 (m, 2H), 1.33 (t, 3H).

1-butyl-5-chloroindoline-2,3-dione

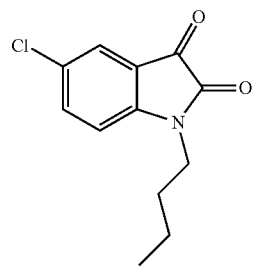 [SMILES: CCCCN1C(=O)C(=O)c2cc(Cl)ccc21]

Was made in an analogous fashion to 1-propylindoline-2,3-dione from commercially available 5-chloro isatin (purchased from Fisher Scientific) and commercially available 1-bromo butane (purchased from Fisher Scientific). 1H NMR δ 7.57 (m, 2H), 6.87 (d, 1H), 3.72 (t, 2H), 1.69 (m, 2H), 1.43 (m, 2H), 0.99 (t, 3H).

1-butyl-5-chloro-2-oxoindolin-3-yl benzoate

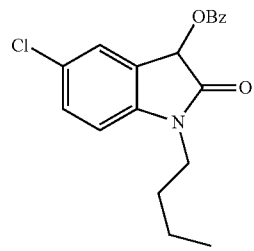

Was made in an analogous fashion to 1-ethyl-5-methyl-2-oxoindolin-3-yl benzoate using 1-butyl-5-chloroindoline-2,3-dione. 1H NMR δ 8.11 (t, 2H), 7.60 (t, 1H), 7.44 (m, 3H), 7.33 (d, 1H), 6.82 (d, 1H), 6.10 (s, 1H), 3.73 (m, 2H), 1.72 (m, 2H), 1.44 (m, 2H), 0.99 (t, 3H).

5-methyl-2-oxo-1-propylindolin-3-yl benzoate

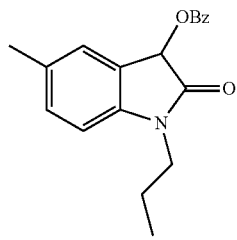

Was made in an analogous fashion to 1-ethyl-5-methyl-2-oxoindolin-3-yl benzoate using 5-methyl-1-propylindoline-2,3-dione. 1H NMR δ 8.13 (dd, 2H), 7.60 (t, 1H), 7.46 (dd, 2H), 7.27 (s, 1H), 7.17 (dd, 1H), 6.80 (d, 1H), 6.19 (s, 1H), 3.74 (m, 2H), 2.33 (s, 3H), 1.80 (m, 2H), 1.04 (t, 3H).

1-isopentyl-2-oxoindolin-3-yl benzoate

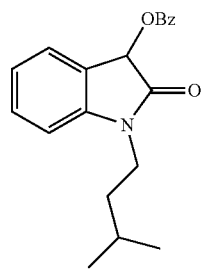

Was made in an analogous fashion to 1-ethyl-5-methyl-2-oxoindolin-3-yl benzoate using 1-isopentylindoline-2,3-dione. 1H-NMR δ 8.10 (d, 2H), 7.59 (t, 1H), 7.46 (dd, 2H), 7.61-7.34 (m, 2H), 7.06 (t, 1H), 6.88 (d, 1H), 6.18 (s, 1H), 3.78 (m, 2H), 1.77-1.60 (m, 3H), 1.02 (dd, 6H).

1-isopentyl-5-methyl-2-oxoindolin-3-yl benzoate

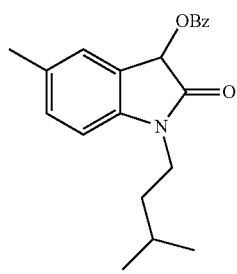

Was made in an analogous fashion to 1-ethyl-5-methyl-2-oxoindolin-3-yl benzoate using 1-isopentyl-5-methylindoline-2,3-dione. 1H NMR δ 8.12 (d, 2H), 7.58 (t, 1H), 7.45 (t, 2H), 7.25 (s, 1H), 7.16 (d, 1H), 6.77 (d, 1H), 6.15 (s, 1H), 3.75 (m, 2H), 2.30 (s, 3H), 1.70 (m, 1H), 1.59 (m, 2H), 1.00 (d, 6H).

1-isobutyl-2-oxoindolin-3-yl benzoate

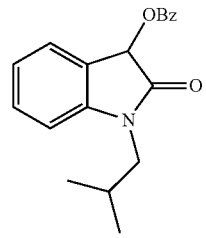

Was made in an analogous fashion to 1-ethyl-5-methyl-2-oxoindolin-3-yl benzoate from 1-isobutylindoline-2,3-dione. 1H-NMR δ 8.10 (d, 2H), 7.59 (t, 1H), 7.46 (m, 3H), 7.34 (m, 1H), 7.05 (t, 1H), 6.89 (d, 1H), 6.18 (s, 1H), 3.52 (m, 2H), 2.18 (m, 1H), 1.01 (dd, 6H).

5-chloro-2-oxo-1-phenethylindolin-3-yl benzoate

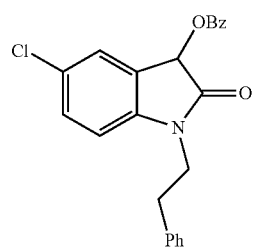

Was made in an analogous fashion to 1-ethyl-5-methyl-2-oxoindolin-3-yl benzoate using 5-chloro-1-phenethylindoline-2,3-dione. 1H-NMR δ 8.11 (dd, 2H), 7.60 (dt, 1H), 7.47 (m, 2H), 7.41 (dd, 1H), 7.34-7.24 (m, 6H), 6.68 (d, 1H), 6.07 (s, 1H), 3.97 (dd, 2H), 3.02 (t, 2H).

2-oxo-1-propylindolin-3-yl benzoate

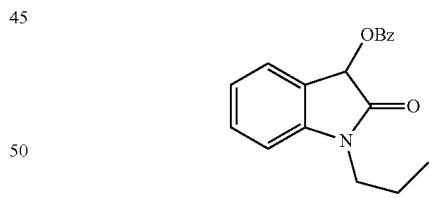

To a dry clean round bottom equipped with a stir bar was added 1-propylindoline-2,3-dione (1 gram, 5.3 mmol) 12 mL of THF and 6 mL of water. While stirring at 0° C. solid sodium borohydride (0.300 grams, 7.93 mmol) was added. The stirring solution was slowly warmed up to room temperature. After all the color had disappeared the reaction was quenched with 1.0 M HCl and diluted with dichloromethane. The organic layer was removed. The aqueous layer was washed two more time with dichloromethane. The combined organic solution was dried with sodium sulfate, filtered and concentrated. It was then used in the subsequent step without further purification.

To a flame dried flask cooled under argon was added the crude 3-hydroxy-1-propylindolin-2-one (0.1 grams, 0.52 mmol) and DMAP (0.007 grams, 0.057 mmol). This was taken up in 5.0 mL of dichloromethane. While stirring at room temperature triethyl amine (78 µL, 0.57 mmol) was added followed by benzoyl chloride (67 µL, 0.57 mmol). The reaction stirred at room temperature until all of the starting material had been consumed. Once complete, the reaction was diluted with water, and the two layers separated. The aqueous layer was washed with dichloromethane twice. The combined organic solution was dried with sodium sulfate, filtered, and concentrated. Chromatography on silica gel using Hexanes/Ethyl acetate (8:2) afforded the desired compound. Yield, 67% for the two steps. 1H-NMR δ 8.11 (d, 2H), 7.58 (dd, 1H), 7.44 (m, 3H), 7.36 (t, 1H), 7.05 (t, 1H), 6.89 (d, 1H), 6.19 (s, 1H), 3.72 (m, 2H), 1.77 (m, 2H), 1.03 (t, 3H).

5-methyl-1-(4-methylpentyl)indoline-2,3-dione

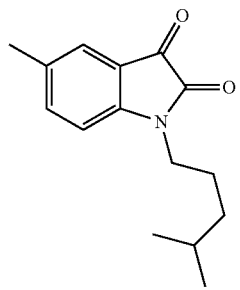 [SMILES: Cc1ccc2c(c1)C(=O)C(=O)N2CCCC(C)C]

This compound was prepared in a similar method as 1-propylindoline-2,3-dione by reacting commercially available 5-methyl isatin (purchase from Fisher Scientific) with commercially available 1-bromo-5-methylpentane (purchase from Fisher Scientific). 1H NMR δ 7.42 (s, 1H), 7.38 (ddd, 1H), 6.79 (d, 1H), 3.68 (t, 2H), 3.34 (s, 3H), 1.69 (m, 2H), 1.60 (m, 1H), 1.27 (m, 2H), 0.88 (d, 6H).

5-methyl-1-(4-methylpentyl)-2-oxoindolin-3-yl benzoate

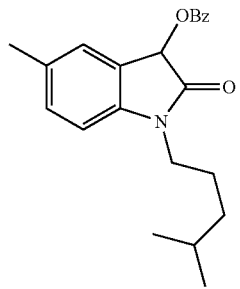

Was made in a similar way to 2-oxo-1-propylindolin-3-yl benzoate starting from 5-methyl-1-(4-methylpentyl)indoline-2,3-dione. 1H-NMR δ 8.11 (d, 2H), 7.58 (dt, 1H), 7.45 (m, 2H), 7.25 (s, 1H), 7.15 (dd, 1H), 6.77 (d, 1H), 6.17 (s, 1H), 3.70 (m, 2H), 2.31 (s, 3H), 1.73 (m, 2H), 1.61 (m, 1H), 1.29 (m, 2H), 0.90 (d, 6H).

tert-butyl (2-formyl-5-methoxyphenyl) carbonate

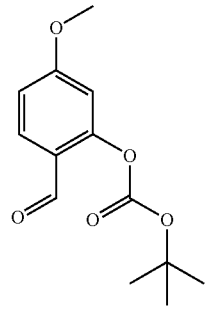 [SMILES: COc1ccc(C=O)c(OC(=O)OC(C)(C)C)c1]

To a flame dried flask cooled under argon equipped with a stir bar was added the 2-hydroxy-4-methoxy-benzaldehyde (1.0 grams, 6.57 mmol, purchased from Fisher Scientific) and di-tertbutyldicarbonate (1.58 grams, 7.27 mmol, purchased from Aldrich). This was taken up in 13.0 mL of dry THF (sure seal, purchased from Aldrich). While stirring at room temperature DMAP (0.04 grams, 0.033 mmol, purchased from Fisher Scientific) was added followed by N-ethyl-NN-diisopropylamine (55.0 µL, purchased from Fisher Scientific). When the reaction was complete, the solvent was removed using a Buchi rotoevaportor, and the residue was purified using a Teledyne ISCO on a silica gel support with hexanes/ethyl acetate gradient. 85% yield. 1H-NMR δ 10.0 (s, 1H), 7.82 (d, 1H), 6.89 (dd, 1H), 6.76 (d, 1H), 3.89 (s, 3H), 1.59 (s, 9H).

tert-butyl (2-(hydroxymethyl)-5-methoxyphenyl) carbonate

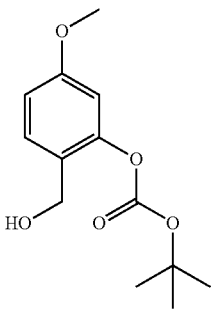 [SMILES: COc1ccc(CO)c(OC(=O)OC(C)(C)C)c1]

To a clean dry flask equipped with a stir bar was added the tert-butyl (2-formyl-5-methoxyphenyl) carbonate (1.5 grams, 5.95 mmol) and 15 mL of anhydrous THF (sure seal, Aldrich). While stirring at 0° C. a solution of sodium borohydride (0.338 grams, 8.93 mmol, purchased from Fisher Scientific) in 5 mL of water was added all at once. After approximately one minute, the reaction was quenched with 0.1M HCl (aqueous), and diluted with ethyl acetate. The organic layer was removed. The aqueous layer was washed with ethyl acetate. The aqueous layer was then salted out using sodium chloride and washed with ethyl acetate twice more. The combined organic material was dried with sodium sulfate, filtered and concentrated. Purification was done on a silica support using hexanes/ethyl acetate (75/25). Yield 33%. 1H-NMR δ 7.37 (d, 1H), 6.82 (dd, 1H), 6.70 (d, 1H), 4.55 (s, 2H), 3.81 (s, 3H), 2.01 (bs, OH), 1.57 (s, 9H).

tert-butyl (2-formyl-4-methoxyphenyl) carbonate

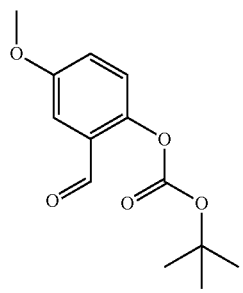 [SMILES: COc1ccc(OC(=O)OC(C)(C)C)c(C=O)c1]

Was prepared in a similar manner to tert-butyl (2-formyl-5-methoxyphenyl) carbonate from commercially available 2-hydroxy-5-methoxy-benzaldehyde and di-tert-butyl-dicarbonate (purchased from Fisher Scientific). 1H-NMR δ 10.2 (s, 1H), 7.37 (d, 1H), 7.21 (d, 1H), 7.19 (dd, 1H), 3.88 (s, 3H), 1.60 (s, 9H).

tert-butyl (2-(hydroxymethyl)-4-methoxyphenyl) carbonate

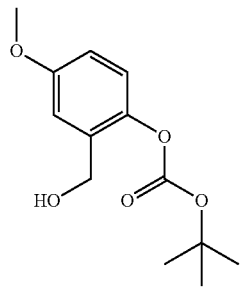 [SMILES: COc1ccc(OC(=O)OC(C)(C)C)c(CO)c1]

This compound was prepared in a similar manner to tert-butyl (2-(hydroxymethyl)-5-methoxyphenyl) carbonate from tert-butyl (2-formyl-4-methoxyphenyl) carbonate. 1H-NMR δ 7.05 (d, 1H), 7.02 (d, 1H), 6.84 (dd, 1H), 4.60 (d, 2H), 3.82 (s, 3H), 2.03 (bs, 1OH), 1.56 (s, 9H).

tert-butyl (2-formyl-6-methoxyphenyl) carbonate

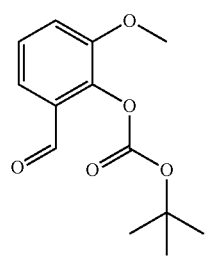 [SMILES: COc1cccc(C=O)c1OC(=O)OC(C)(C)C]

Was prepared in a similar manner to tert-butyl (2-formyl-5-methoxyphenyl) carbonate from commercially available 2-hydroxy-3-methoxy-benzaldehyde and di-tert-butyl-dicarbonate (purchased from Fisher Scientific). 1H-NMR δ 10.3 (s, 1H), 7.49 (dd, 1H), 7.33 (dd, 1H), 7.24 (dd, 1H), 3.92 (s, 3H), 1.59 (s, 9H).

tert-butyl (2-(hydroxymethyl)-6-methoxyphenyl) carbonate

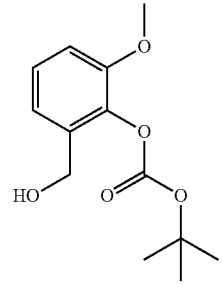 [SMILES: COc1cccc(CO)c1OC(=O)OC(C)(C)C]

This compound was prepared in a similar manner to tert-butyl (2-(hydroxymethyl)-5-methoxyphenyl) carbonate from tert-butyl (2-formyl-6-methoxyphenyl) carbonate. 1H-NMR δ 7.23 (dd, 1H), 7.04 (d, 1H), 6.93 (dt, 1H), 4.65 (s, 2H), 3.86 (s, 3H), 1.72 (bs, OH), 1.40 (s, 9H).

5-chloro-1-isopentylindoline-2,3-dione

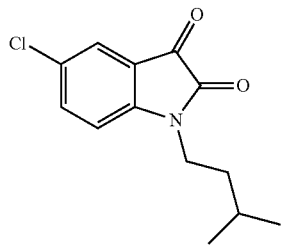 [SMILES: CC(C)CCN1C(=O)C(=O)c2cc(Cl)ccc21]

This compound was prepared in a similar method as 1-propylindoline-2,3-dione by reacting commercially available 5-chloro isatin (purchase from Fisher Scientific) with commercially available 1-bromo-3-methylbutane (purchase from Fisher Scientific). 1H NMR δ 7.57 (m, 2H), 6.85 (d, 1H), 3.73 (t, 2H), 1.57 (m, 3H), 1.00 (d, 6H).

5-chloro-1-isopentyl-2-oxoindolin-3-yl benzoate

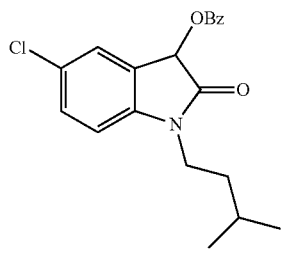

This compound was prepared in a similar way to 2-oxo-1-propylindolin-3-yl benzoate starting from 5-chloro-1-isopentylindoline-2,3-dione. 1H-NMR δ 8.11 (dd, 2H), 7.60

(dt, 1H), 7.47 (m, 2H) 7.45 (m, 3H), 7.33 (dd, 1H), 6.80 (d, 1H), 6.10 (d, 1H), 3.76 (m, 2H), 1.72 (m, 1H), 1.01 (dd, 6H).

4-(3-bromopropyl)morpholine

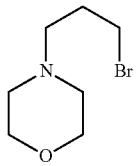

This compound was prepared following the procedure in PCT/US09/02871.

5-chloro-1-(3-morpholinopropyl)indoline-2,3-dione

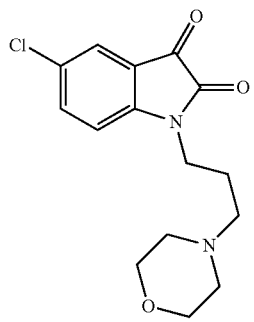 [SMILES: O=C1C(=O)N(CCCN2CCOCC2)c2ccc(Cl)cc21]

This compound was prepared in a similar method as 1-propylindoline-2,3-dione by reacting commercially available 5-chloro isatin (purchase from Fisher Scientific) with the 4-(3-bromopropyl)morpholine. 1H NMR δ 7.57 (m, 2H), 6.98 (d, 1H), 3.82 (t, 2H), 3.64 (m, 4H), 2.41 (m, 6H), 1.87 (m, 2H).

5-chloro-1-(3-morpholinopropyl)-2-oxoindolin-3-yl benzoate

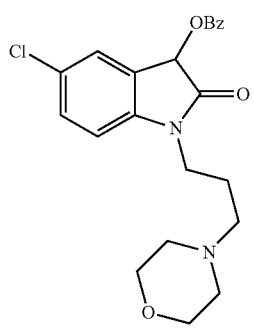

This compound was prepared in a similar way to 2-oxo-1-propylindolin-3-yl benzoate from 5-chloro-1-(3-morpholinopropyl)indoline-2,3-dione. 1H-NMR δ 8.07 (dd, 2H), 7.63 (dd, 1H), 7.53 (dd, 2H), 7.42 (s, 1H), 7.33 (dd, 1H), 7.6.92 (d, 1H), 6.09 (s, 1H), 3.84 (m, 2H), 3.76 (m, 4H), 2.50 (m, 6H), 1.97 (m, 2H).

(1-benzoyl-1H-indol-3-yl)methyl benzoate

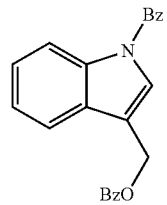

To an oven dried flask that cooled under argon was added the (1H-indol-3-yl)methanol (1.0 grams, 6.8 mmol, 0.1M in dry dichloromethane, purchased from Fisher Scientific, stored over 4 angstrom molecular sieves) and DMAP (0.083 grams, 0.68 mmol). While stirring at 0° C., triethyl amine (2.0 mL, 14.3 mmol, purchased from Fisher Scientific) was added followed by benzoyl chloride (0.96 mL, 8.2 mmol, purchased from Fisher Scientific). Once the reaction was complete it was diluted with water, and the organic layer removed. The aqueous layer was then washed with dichloromethane twice and the organic material combined. The organic material was dried with sodium sulfate, filtered, and concentrated. Purification using a Teledyne ISCO on silica support (hexanes/ethyl acetate gradient) afforded the desired 1-benzoyl-1H-indol-3-yl)methyl benzoate. 42% yield. 1H-NMR δ 8.42 (d, 1H), 8.02 (dd, 2H), 7.76 (m, 3H), 7.62 (dd, 1H), 7.54 (m, 3H), 7.47-7.37 (m, 5H), 5.50 (s, 2H).

5-chloro-2-oxo-1-propylindolin-3-yl benzoate

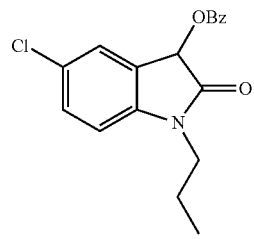

Was prepared in a method analogous to 2-oxo-1-propylindolin-3-yl benzoate using 5-chloro-1-propylindoline-2,3-dione. 1H-NMR δ 8.11 (dd, 2H), 7.60 (dt, 1H), 7.47 (m, 3H), 7.35 (dd, 1H), 6.83 (d, 1H), 6.13 (s, 1H), 3.73 (m, 2H), 1.77 (m, 2H), 1.04 (t, 3H).

1-butyl-2-oxoindolin-3-yl benzoate

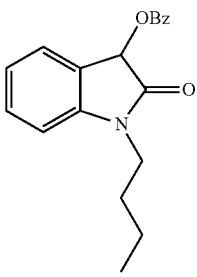

Was prepared in a method analogous to 2-oxo-1-propylindolin-3-yl benzoate using 1-butylindoline-2,3-dione. 1H-NMR δ 8.11 (d, 2H), 7.58 (m, 1H), 7.49-7.34 (m, 4H), 7.05 (dd, 1H), 6.89 (d, 1H), 6.19 (s, 1H), 3.75 (m, 2H), 1.73 (m, 2H), 1.44 (m, 2H), 0.99 (t, 3H).

II. Preparation of Certain Embodiments of the Invention

Example 1

3-((3-bromopyridin-2-yl)methyl)-3-hydroxy-1-isopentyl-5-methylindolin-2-one

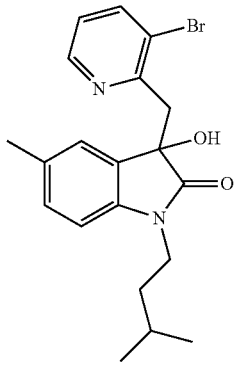 [SMILES: Cc1ccc2c(c1)C(O)(Cc1ncccc1Br)C(=O)N2CCC(C)C]

To a flame dried flask cooled under argon was added freshly prepared LDA (0.82 mL, 0.48 mmol, 0.38M in anhydrous THF). While stirring at −78° C., 3-bromo-2-methyl pyridine (50 μL, 0.48 mmol, purchased from Aldrich) was added. The solution stirred at this temperature for two hours at which point a 1-isopentyl-5-methylindoline-2,3-dione (0.045 grams, 0.19 mmol, 0.4 M in THF) was added. The solution was then warmed to room temperature slowly. Once all of the starting material had been consumed, the reaction was quenched with ammonium chloride (saturated), diluted with ethyl acetate, and the organic layer removed. The aqueous layer was salted out using sodium chloride and washed two more times with ethyl acetate. The combined organic material was dried with sodium sulfate, filtered, and concentrated. Purification was done on preparative thin layer chromatography using hexanes/ethyl acetate (2:1) to afford the desired material. (8% Yield). 1H NMR δ 8.53 (dd, 1H), 7.89 (dd, 1H), 7.17-7.09 (m, 3H), 7.03 (d, 1H), 6.73 (d, 1H), 3.83-57 (m, 2H), 3.52 (d, 1H), 3.34 (d, 1H), 2.30 (s, 3H), 1.65 (m, 1H), 1.54 (m, 2H), 0.96 (dd, 6H). Calculated mass for C20H23BrN2O2 402.09, observed, 425.1 (M+Na).

Example 2

5-chloro-1-ethyl-3-hydroxy-3-((4-hydroxypyridin-2-yl)methyl)indolin-2-one

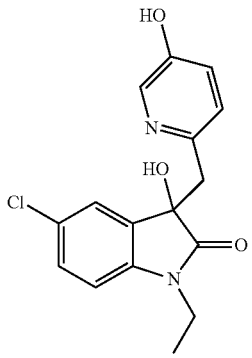 [SMILES: CCN1C(=O)C(O)(Cc2ccc(O)cn2)c2cc(Cl)ccc21]

To a flame dried sealed tube cooled under argon was added the 5-chloro-N-ethyl-isatin (0.02 grams, 0.095 mmol) and 5-hydroxy-2-methyl-pyridine (0.023 grams, 0.21 mmol, purchased from Fisher Scientific) and 0.3 mL of 1,4 dioxane (anhydrous, Sure seal, purchased from Aldrich). After the addition of trifluroacetic acid (1 μL) the vessel was sealed and heated to 110° C. for 5 days. The reaction was then concentrated. Chromatography was performed using a Teledyne ISCO dichloromethane/(dichloromethane with methanol (9:1)) Yield 13%, gradient. 1H-NMR δ 8.12 (s, 1H), 7.26 (m, 1H), 7.11 (d, 1H), 7.09 (s, 1H), 6.93 (d, 1H), 6.79 (d, 1H), 3.73 (q, 2H), 3.18 (d, 1H), 3.09 (d, 1H), 2.51 (s, 1H), 1.25 (m, 4H).

Example 3

5-chloro-3-hydroxy-3-((3-methoxypyridin-2-yl)methyl)-1-phenethylindolin-2-one

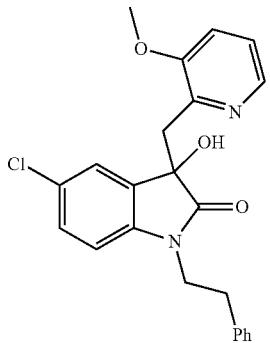 [SMILES: COc1cccnc1CC1(O)C(=O)N(CCc2ccccc2)c2ccc(Cl)cc21]

This compound was prepared in an analogous manner to 3-((3-bromopyridin-2-yl)methyl)-3-hydroxy-1-isopentyl-5-methylindolin-2-one using 5-chloro-1-phenethylindoline-2,3-dione and 3-methoxy-2-methylpyridine. 1H-NMR δ 8.21 (dd, 1H), 7.33-7.17 (m, 8H), 6.95 (d, 1H), 6.62 (d, 1H), 5.5 (bs, OH), 3.98 (m, 1H), 3.86 (m, 1H), 3.78 (s, 3H), 3.37 (d, 1H), 3.09 (d, 1H), 2.96 (t, 2H).

Example 4

5-chloro-3-hydroxy-1-(2-(piperidin-1-yl)ethyl)-3-(pyridin-2-ylmethyl)indolin-2-one

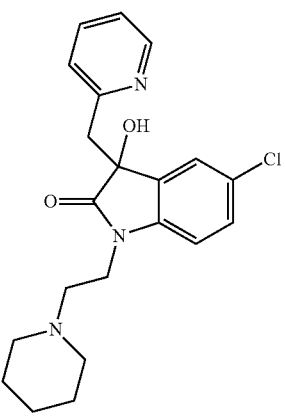 [SMILES: O=C1N(CCN2CCCCC2)c2ccc(Cl)cc2C1(O)Cc1ccccn1]

This compound was prepared in an analogous manner to 3-(3-bromopyridin-2-yl)methyl)-3-hydroxy-1-isopentyl-5-methylindolin-2-one using 5-chloro-1-(2-(piperidin-1-yl)ethyl)indoline-2,3-dione and 2-methyl pyridine (purchased from Fisher Scientific). 1H-NMR δ 8.61 (d, 1H), 7.70 (m, 2H), 7.32 (dd, 1H), 7.24 (dd, 1H), 7.10 (d, 1H), 6.82 (m, 2H), 3.87-3.75 (m, 2H), 3.33 (d, 1H), 3.11 (d, 1H), 2.62-2.47 (m, 6H), 1.57 (m, 4H), 1.45 (m, 2H). Calculated mass for C21H24ClN3O2, 385.16, observed, 386.1 (M+1).

Example 5

5-chloro-3-hydroxy-3-((5-methoxypyridin-2-yl)methyl)-1-propylindolin-2-one

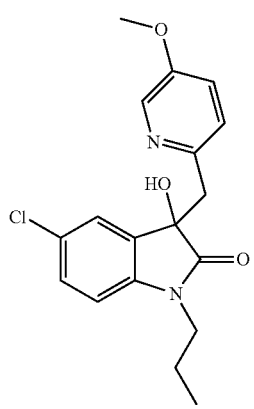 [SMILES: CCCN1C(=O)C(O)(Cc2ccc(OC)cn2)c2cc(Cl)ccc21]

This compound was prepared in an analogous manner to 3-((3-bromopyridin-2-yl)methyl)-3-hydroxy-1-isopentyl-5-methylindolin-2-one using 5-chloro-1-propylindoline-2,3-dione and 5-methoxy-2-methylpyridine. 1H-NMR δ 8.31 (s, 1H), 7.25 (m, 2H), 7.01 (d, 1H), 6.84 (s, 1H), 6.78 (m, 1H), 4.02 (bs, OH), 3.91 (s, 3H), 3.61 (m, 2H), 3.28 (d, 1H), 3.06 (d, 1H), 1.79 (m, 2H), 0.98 (t, 3H). Calculated mass for C18H19ClN2O3, 346.11. Observed, 347.1 (M+1).

Example 6

3-hydroxy-3-((5-methoxypyridin-2-yl)methyl)-5-methyl-1-propylindolin-2-one

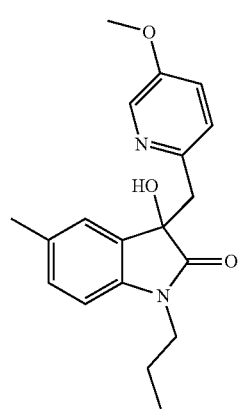 [SMILES: CCCN1C(=O)C(O)(Cc2ccc(OC)cn2)c2cc(C)ccc21]

This compound was prepared in an analogous manner to 3-((3-bromopyridin-2-yl)methyl)-3-hydroxy-1-isopentyl-5-methylindolin-2-one using 5-methyl-1-propylindoline-2,3-dione and 5-methoxy-2-methylpyridine. 1H-NMR δ 8.3 (s, 1H), 7.20 (d, 1H), 7.08 (d, 1H), 6.98 (d, 1H), 6.73 (m, 2H), 4.2 (bs, OH), 3.92 (s, 3H), 3.61 (m, 2H), 3.23 (d, 1H), 3.12 (d, 1H), 2.62 (s, 3H), 1.70 (m, 2H), 0.97 (t, 3H). Calculated mass for C19H22N2O3, 326.16. Observed, 327.1 (M+1).

Example 7

5-chloro-1-ethyl-3-hydroxy-3-((3-methoxypyridin-2-yl)methyl)indolin-2-one

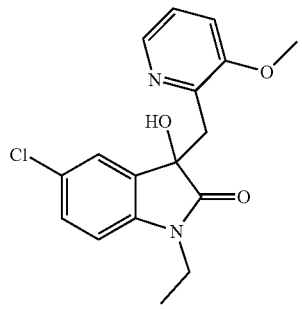 [SMILES: CCN1C(=O)C(O)(Cc2ncccc2OC)c2cc(Cl)ccc21]

This compound was prepared in an analogous manner to 3-(3-bromopyridin-2-yl)methyl)-3-hydroxy-1-isopentyl-5-methylindolin-2-one using 5-chloro-1-ethylindoline-2,3-dione and 3-methoxy-2-methylpyridine. 1H-NMR δ 8.21 (s, 1H), 7.5 (bs, OH), 7.26 (m, 3H), 6.99 (s, 1H), 6.78 (d, 1H), 3.77 (s, 3H), 3.76 (m, 2H), 3.45 (d, 1H), 3.19 (d, 1H), 1.27 (t, 3H). Calculated mass for C17H17ClN2O3, 332.09. Observed, 333.1 (M+1).

Example 8

1-ethyl-3-hydroxy-3-((3-methoxypyridin-2-yl)methyl)-5-methylindolin-2-one

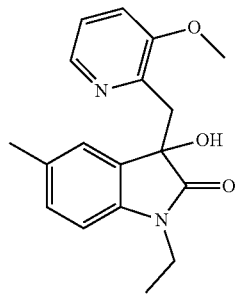 [SMILES: CCN1C(=O)C(O)(Cc2ncccc2OC)c2cc(C)ccc21]

To a flame dried sealed tube cooled under argon was added the 1-ethyl-5-methylindoline-2,3-dione (0.03 grams, 0.15 mmol) and 3-methoxy-2-methyl-pyridine (0.072 grams, 0.59 mmol, purchased from Fisher Scientific) and 0.5 mL of 1,4 dioxane. After the addition of trifluroacetic acid (2 μL) the vessel was sealed and heated to 110° C. for 48 hours. The reaction was then concentrated. 1H-NMR δ 8.21 (s, 1H), 7.35 (bs, OH), 7.26 (m, 1H), 7.20 (d, 1H), 7.09 (d, 1H), 6.90 (s, 1H), 6.75 (d, 1H), 3.78 (s, 3H), 3.77 (m, 2H), 3.34 (d, 1H), 3.18 (d, 1H), 2.27 (s, 3H), 1.28 (t, 3H).

Calculated mass for C18H20N2O3, 312.15. Observed 313.1 (M+1).

Example 9

3-hydroxy-5-methyl-1-phenethyl-3-(pyridin-2-ylmethyl)indolin-2-one

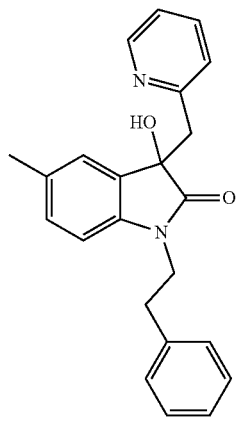 [SMILES: Cc1ccc2c(c1)C(O)(Cc1ccccn1)C(=O)N2CCc1ccccc1]

This compound was prepared in an analogous manner to 3-((3-bromopyridin-2-yl)methyl)-3-hydroxy-1-isopentyl-5-methylindolin-2-one using 5-methyl-1-phenethylindoline-2,3-dione and 2-methylpyridine (purchased from Fisher Scientific). 1H-NMR δ 8.6 (d, 1H), 7.65 (m, 1H), 7.27 (m, 6H), 7.05 (d, 1H), 6.98 (d, 1H), 6.71 (m, 2H), 4.6 (bs, OH), 3.5 (m, 1H), 3.8 (m, 1H), 3.1 (m, 2H), 2.95 (m, 2H), 2.21 (s, 3H). Calculated mass for C23H22N2O2, 358.17. Observed 359.1 (M+1).

Example 10

5-chloro-1-ethyl-3-hydroxy-3-(pyridin-2-ylmethyl)indolin-2-one

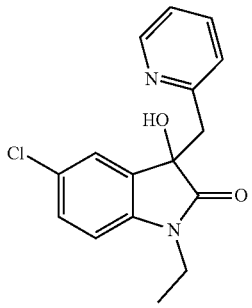 [SMILES: CCN1C(=O)C(O)(Cc2ccccn2)c2cc(Cl)ccc21]

This compound was prepared in an analogous manner to 3-((3-bromopyridin-2-yl)methyl)-3-hydroxy-1-isopentyl-5-methylindolin-2-one using 5-chloro-1-ethylindoline-2,3-dione and 2-methyl pyridine (purchased from Fisher Scientific). 1H-NMR δ 8.60 (d, 1H), 7.65 (dd, 1H), 7.27 (m, 3H), 7.09 (d, 1H), 6.75 (m, 2H), 3.72 (m, 2H), 3.35 (d, 1H), 3.09 (d, 1H), 1.21 (t, 3H). Calculated mass for C16H15ClN2O2, 302.08. Observed 303.1 (M+1).

Example 11

3-hydroxy-3-((5-methoxypyridin-2-yl)methyl)-5-methyl-1-phenethylindolin-2-one

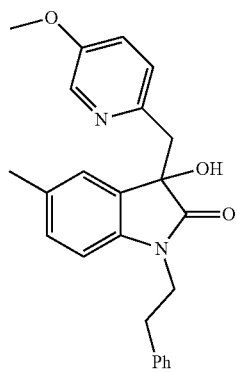 [SMILES: COc1ccc(CC2(O)C(=O)N(CCc3ccccc3)c3ccc(C)cc32)nc1]

This compound was prepared in an analogous manner to 3-((3-bromopyridin-2-yl)methyl)-3-hydroxy-1-isopentyl-5-methylindolin-2-one using 5-methyl-1-phenethylindoline-2,3-dione and 5-methoxy-2-methylpyridine (purchased from Aldrich). 1H-NMR δ 8.29 (d, 1H), 7.34 (m, 2H), 7.25 (m, 3H), 7.18 (dd, 1H), 7.07 (dd, 1H), 6.90 (d, 1H), 6.80 (s, 1H), 6.71 (d, 1H), 5.3 (bs, OH), 3.98 (dt, 1H), 3.91 (s, 3H), 3.81 (dt, 1H), 3.05 (d, 2H), 2.97 (t, 2H), 2.27 (s, 3H). Calculated mass for C24H24N2O3, 388.18. Observed 389.2 (M+1).

Example 12

1-butyl-3-hydroxy-3-(2-oxo-2-(pyridin-2-yl)ethyl)indolin-2-one

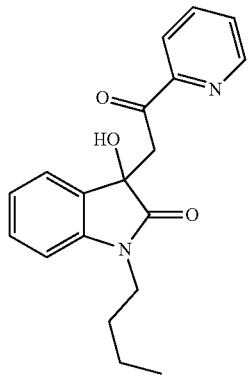 [SMILES: CCCCN1C(=O)C(O)(CC(=O)c2ccccn2)c2ccccc21]

To a clean dry flask equipped with a stir bar was added the N-butyl isatin (0.4 grams, 1.97 mmol, 0.3 M in Methanol). 2-acetyl pyridine (0.44 mL, 3.94 mmol, purchased from Fisher Scientific) was then added to the stirring solution followed by 49 µL of dimethyl amine (40% by weight in water, purchased from Fisher Scientific). The stirring solution was stirred overnight at room temperature. The next day the solution was heated to 60° C. for 5 minutes. The solution was then concentrated and purified on a silica gel column using hexanes/ethyl acetate (2:1) to afford 0.513 grams, 80% yield. 1H-NMR δ 8.69 (d, 1H), 8.14 (d, 1H), 7.92 (t, 1H), 7.56 (m, 1H) 7.30 (m, 2H), 7.06 (t, 1H), 6.87 (d, 2H), 3.81

(d, 1H), 3.69 (m, 2H), 3.52 (d, 1H), 1.71 (m, 2H), 1.43 (m, 2H), 0.97 (t, 3H). Calculated mass for C19H20N2O3, 324.37. Observed 325.0 (M+1), 347.2 (M+Na).

Example 13

3-(2-(1H-indol-3-yl)-2-oxoethyl)-3-hydroxy-5-methyl-1-(pent-4-yn-1-yl)indolin-2-one

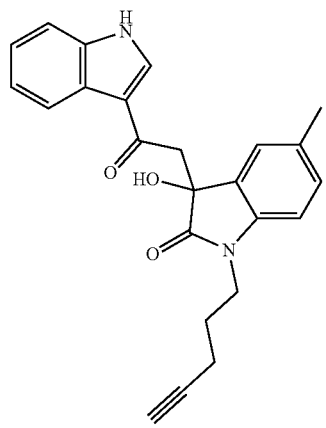 [SMILES: C#CCCCN1C(=O)C(O)(CC(=O)c2c[nH]c3ccccc23)c2cc(C)ccc21]

To a clean dry Biotage microwave vial equipped with a stir bar was added the 5-methyl-1-(pent-4-yn-1-yl)indoline-2,3-dione (0.015 grams, 0.066 mmol), 1-(1H-indol-3-yl)ethanone (0.19 grams, 0.12 mmol, purchased from Fisher scientific) and 0.2 mL of methanol. 9.0 µL of dimethyl amine (40% by weight in water) was then added and the solution was placed in a Biotage initiator and heated at 100° C. for thirty minutes. The solution was then concentrated and purified on a Teledyne ISCO using hexanes and ethyl acetate. Yield, 20%. 1H-NMR δ 9.15 (bs, 1H), 8.33 (m, 1H), 7.69 (s, 1H), 7.39 (m, 1H) 7.38 (m, 1H), 7.27 (m, 2H), 7.10 (d, 1H), 6.84 (d, 1H), 5.58 (bs, OH), 3.81 (p, 2H), 3.49 (d, 1H), 3.24 (d, 1H) 2.28 (m, 5H), 2.01 (t, 1H), 1.92 (m, 2H).

Example 14

5-chloro-3-(2-(6-ethynylpyridin-2-yl)-2-oxoethyl)-3-hydroxy-1-propylindolin-2-one

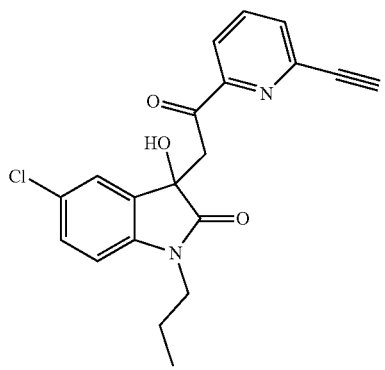 [SMILES: C#Cc1cccc(C(=O)CC2(O)C(=O)N(CCC)c3ccc(Cl)cc32)n1]

To a flame dried flask cooled under argon equipped with a stir bar was added 1-(6-bromopyridin-2-yl)ethanone (0.1 grams, 0.5 mmol, purchased from Fisher Scientific), Copper (I) iodide (0.019 grams, 0.1 mmol) triethyl amine (0.13 mL, 1.0 mmol, purchased from Fisher Scientific), and THF (0.5 mL, anhydrous, purchased from Fisher Scientific). After submitting to an argon sparge for 20 minutes Pd(PPH3)4 (0.058 grams, 0.05 mmol, purchased from Fisher Scientific) was added followed by trimethyl silyl acetylene (0.294 mL, 2.1 mmol, purchased from Fisher Scientific). The vessel was sealed and stirred at room temperature overnight. The next day it was filtered through a 45 micron frit, concentrated, and purified with a Teledyne ISCO on silica support using a hexanes, ethyl acetate gradient. The product was then used for the subsequent reaction. (80% yield). 1H NMR δ 7.97 (d, 1H), 7.78 (t, 1H), 7.61 (d, 1H), 2.74 (s, 3H), 0.38 (s, 9H).

To a clean biotage vial equipped with a stir bar was added 1-(6-((trimethylsilyl)ethynyl)pyridin-2-yl)ethanone (0.0255 grams, 0.12 mmol), 5-chloro-1-propylindoline-2,3-dione, (0.015 grams, 0.067 mmol). This was taken up in 0.2 mL of methanol (purchased from Fisher Scientific). Dimethylamine (2.5 µL 40% in water purchased from Fisher Scientific) was then added and the solution heated in a Biotage initiator microwave for ten minutes at 80° C. Once complete, the reaction was concentrated using a Buchi rotoevaporator and purified using a Teledyne ISCO with silica gel (hexane, ethyl acetate gradient). Yield, 40%. 1H-NMR δ 8.06 (dd, 1H), 7.89 (t, 1H), 7.69 (dd, 1H), 7.35 (d, 1H), 7.29 (dd, 1H), 6.80 (d, 1H), 6.02 (s, 1H), 3.88 (d, 1H), 3.62 (m, 3H), 3.25 (s, 1H), 1.71 (m, 2H), (0.97 (t, 3H). calculated mass for C20H17ClN2O3, 368.09. Observed, 369.0 (M+1).

Example 15

3-(2-(1H-indol-3-yl)-2-oxoethyl)-3-hydroxy-1-isopentyl-5-methylindolin-2-one

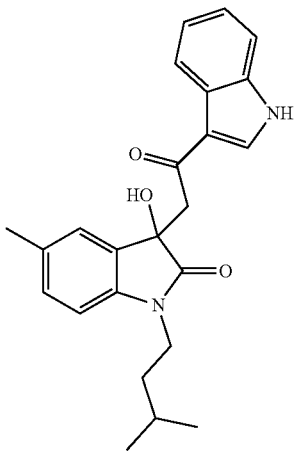 [SMILES: Cc1ccc2c(c1)C(O)(CC(=O)c1c[nH]c3ccccc13)C(=O)N2CCC(C)C]

This compound was made in a similar manner to 1-butyl-3-hydroxy-3-(2-oxo-2-(pyridin-2-yl)ethyl)indolin-2-one using 1-isopentyl-5-methylindoline-2,3-dione and commercially available 1-(1H-indol-3-yl)ethanone (purchased from Fisher Scientific). 1H-NMR δ 9.21 (bs, NH), 8.34 (m, 1H), 7.67 (d, 1H), 7.38 (m, 1H), 7.30-7.23 (m, 3H), 7.08 (d, 1H), 6.73 (d, 1H) 5.74 (bs, 1H), 3.68 (t, 2H), 3.49 (d, 1H), 3.21 (d, 1H), 2.27 (s, 3H), 1.67-1.49 (m, 3H), 0.95 (dd, 6H).

Example 16

3-hydroxy-1-isobutyl-3-(2-oxo-2-(pyridin-2-yl)ethyl)indolin-2-one

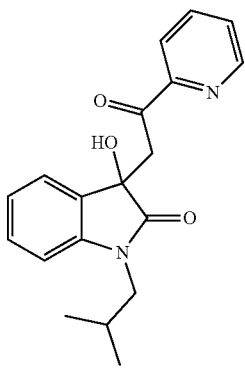 [SMILES: CC(C)CN1C(=O)C(O)(CC(=O)c2ccccn2)c2ccccc21]

This compound was made in a similar manner to 1-butyl-3-hydroxy-3-(2-oxo-2-(pyridin-2-yl)ethyl)indolin-2-one using 1-isobutylindoline-2,3-dione and commercially available 2-acetyl pyridine (Fisher Scientific). 1H-NMR δ 8.70 (ddd, 1H), 8.13 (td, 1H), 7.92 (dd, 1H), 7.56 (ddd, 1H), 7.34-7.28 (m, 2H), 7.07-7.02 (m, 2H), 6.85 (d, 1H), 3.77 (d, 1H), 3.56-3.42 (m, 3H), 2.15 (m, 1H), 0.97 (dd, 6H). calculated mass for C19H20N2O3, 324.15. Observed, 325.1 (M+1).

Example 17

5-chloro-3-hydroxy-1-isobutyl-3-(2-(6-methoxypyridin-2-yl)-2-oxoethyl)indolin-2-one

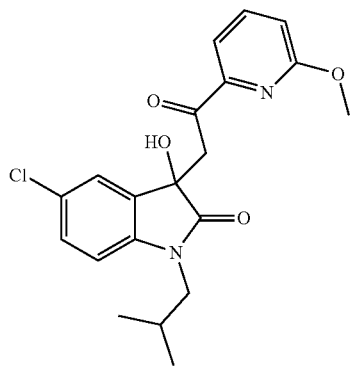 [SMILES: COc1cccc(C(=O)CC2(O)C(=O)N(CC(C)C)c3ccc(Cl)cc32)n1]

This compound was made in a similar manner to 1-butyl-3-hydroxy-3-(2-oxo-2-(pyridin-2-yl)ethyl)indolin-2-one from 5-chloro-1-isobutylindoline-2,3-dione and 1-(6-methoxypyridin-2-yl)ethanone (purchased from Fisher Scientific). 1H-NMR δ 7.75 (m, 1H), 7.67 (d, 1H), 7.35 (d, 1H), 7.29 (d, 1H), 7.00 (dd, 1H), 6.79 (d, 1H) 5.40 (bs, OH), 4.00 (m, 4H), 3.57-3.43 (m, 3H), 2.14 (m, 1H), 0.97 (dd, 6H). calculated mass for C20H21N2O4, 388.12, observed, 389.1 (M+1).

Example 18

5-chloro-3-hydroxy-3-(2-(6-methoxypyridin-2-yl)-2-oxoethyl)-1-(2-(piperidin-1-yl)ethyl)indolin-2-one

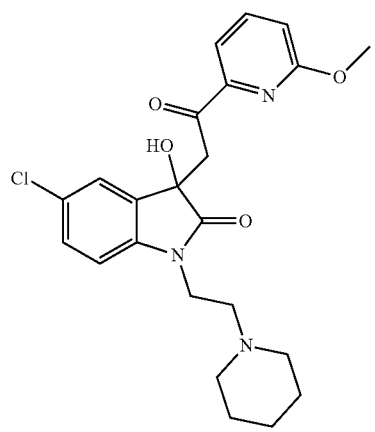 [SMILES: COc1cccc(C(=O)CC2(O)C(=O)N(CCN3CCCCC3)c3ccc(Cl)cc32)n1]

This compound was made in a similar manner to 1-butyl-3-hydroxy-3-(2-oxo-2-(pyridin-2-yl)ethyl)indolin-2-one using 5-chloro-1-(2-(piperidin-1-yl)ethyl)indoline-2,3-dione and 1-(6-methoxypyridin-2-yl)ethanone (commercially available from Fisher Scientific). 1H-NMR δ 7.72 (t, 1H), 7.63 (d, 1H), 7.34 (d, 1H), 7.28 (d, 1H) 6.98 (d, 1H), 6.86 (d, 1H), 5.5 (bs, OH), 4.04 (d, 1H), 4.00 (s, 3H), 3.8 (m, 2H), 3.60 (d, 1H), 2.60 (m, 6H), 1.55 (m, 4H), 1.43 (m, 2H). calculated mass for C23H26ClN3O4, 443.16, observed, 444.1 (M+1).

Example 19

5-chloro-1-ethyl-3-hydroxy-3-(2-oxo-2-(pyridin-2-yl)ethyl)indolin-2-one

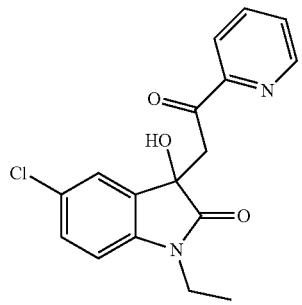 [SMILES: CCN1C(=O)C(O)(CC(=O)c2ccccn2)c2cc(Cl)ccc21]

This compound was made in a similar manner to 1-butyl-3-hydroxy-3-(2-oxo-2-(pyridin-2-yl)ethyl)indolin-2-one using 5-chloro-1-ethylindoline-2,3-dione and 2-acetyl pyridine (purchased from Fisher Scientific). 1H-NMR δ 8.70 (ddd, 1H), 8.11 (dd, 1H), 7.93 (ddd, 1H), 7.57 (ddd, 1H), 7.31-7.27 (m, 2H), 6.79 (d, 1H), 5.5 (bs, OH), 3.77 (d, 1H), 3.74 (m, 2H), 3.53 (d, 1H), 1.27 (t, 3H). calculated mass for C17H15ClN2O3, 330.08, observed, 331.0 (M+1).

Example 20

3-(2-(1H-indol-3-yl)-2-oxoethyl)-3-hydroxy-1-isobutylindolin-2-one

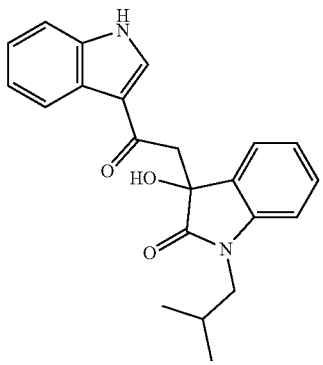 [SMILES: CC(C)CN1C(=O)C(O)(CC(=O)c2c[nH]c3ccccc23)c2ccccc21]

This compound was made in a similar manner to 1-butyl-3-hydroxy-3-(2-oxo-2-(pyridin-2-yl)ethyl)indolin-2-one using 1-isobutylindoline-2,3-dione and commercially available 1-(1H-indol-3-yl)ethanone (purchased from Fisher Scientific). 1H-NMR δ 8.87 (bs, NH), 8.38 (m, 1H), 7.72 (d, 3.1 Hz, 1H), 7.49 (dd, 1H), 7.47 (m, 1H) 7.30 (m, 3H), 7.01 (dd, 1H), 6.86 (d, 7.8, 1H), 3.51 (m, 3H), 3.24 (d, 1H), 2.16 (m, 1H) 0.98 (dd, 6H). Calculated mass for C22H22N2O3, 362.16. Observed 385.3 (M+Na).

Example 21

3-(2-(1H-indol-3-yl)-2-oxoethyl)-3-hydroxy-1-isopentylindolin-2-one

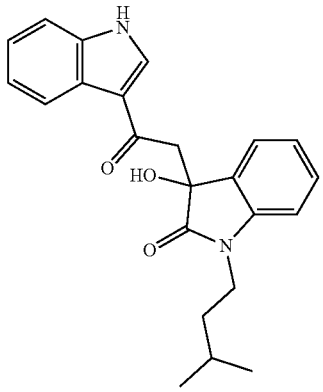 [SMILES: CC(C)CCN1C(=O)C(O)(CC(=O)c2c[nH]c3ccccc23)c2ccccc21]

This compound was made in a similar manner to 1-butyl-3-hydroxy-3-(2-oxo-2-(pyridin-2-yl)ethyl)indolin-2-one using 1-isopentylindoline-2,3-dione and commercially available 1-(1H-indol-3-yl)ethanone (purchased from Fisher Scientific). 1H-NMR δ 9.41 (bs, 1H), 8.33 (s, 1H), 7.82 (m, 1H), 7.66 (d, 1H), 7.47 (d, 1H), 7.25 (m, 3H), 7.00 (t, 1H), 6.84 (d, 1H), 5.89 (bs, 1H), 3.71 (t, 2H), 3.49 (d, 1H), 3.21 (d, 1H), 1.62 (m, 2H), 1.54 (m, 1H), 0.94 (dd, 6H).

Example 22

5-chloro-3-(2-(2,6-dimethoxypyridin-3-yl)-2-oxoethyl)-3-hydroxy-1-propylindolin-2-one

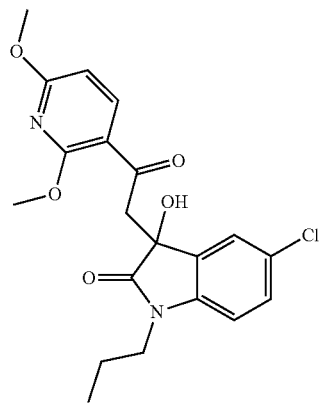 [SMILES: CCCN1C(=O)C(O)(CC(=O)c2ccc(OC)nc2OC)c2cc(Cl)ccc21]

This compound was made in a similar manner to 1-butyl-3-hydroxy-3-(2-oxo-2-(pyridin-2-yl)ethyl)indolin-2-one using 5-chloro-1-propylindoline-2,3-dione and 1-(2,6-dimethoxypyridin-3-yl)ethanone (purchased from Fisher Scientific). 1H-NMR δ 8.12 (d, 1H), 7.39 (s, 1H), 7.27 (d, 1H), 6.80 (d, 1H), 6.35 (d, 1H) 4.63 (bs, OH), 4.00 (s, 3H), 3.83 (s, 3H), 3.71 (d, 1H), 3.68 (m, 2H), 3.47 (d, 1H), 1.73 (m, 2H), 0.99 (t, 3H). Calculated mass for C20H21ClN2O5, 404.11. Observed 427.1 (M+Na)

Example 23

5-chloro-3-hydroxy-3-(2-oxo-2-(pyridin-2-yl)ethyl)-1-propylindolin-2-one

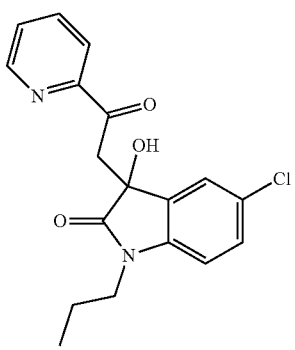 [SMILES: CCCN1C(=O)C(O)(CC(=O)c2ccccn2)c2cc(Cl)ccc21]

This compound was made in a similar manner to 1-butyl-3-hydroxy-3-(2-oxo-2-(pyridin-2-yl)ethyl)indolin-2-one using 5-chloro-1-propylindoline-2,3-dione and 2-acetyl pyridine (purchased from Fisher Scientific). 1H-NMR δ 8.70 (d, 1H), 8.10 (d, 1H), 7.92 (t, 1H), 7.56 (dd, 1H), 7.28 (m, 2H), 6.79 (d, 1H), 3.63 (m, 5H), 1.70 (m, 2H), 0.96 (t, 3H). Calculated mass for C18H17ClN2O3, 344.09. Observed 345.0 (M+1), 367.1 (M+Na).

Example 24

3-(2-(1H-indol-3-yl)-2-oxoethyl)-3-hydroxy-5-methyl-1-propylindolin-2-one

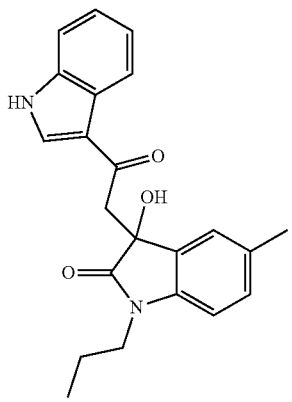 [SMILES: CCCN1C(=O)C(O)(CC(=O)c2c[nH]c3ccccc23)c2cc(C)ccc21]

This compound was made in a similar manner to 1-butyl-3-hydroxy-3-(2-oxo-2-(pyridin-2-yl)ethyl)indolin-2-one using 5-methyl-1-propylindoline-2,3-dione and commercially available 1-(1H-indol-3-yl)ethanone (purchased from Fisher Scientific). 1H-NMR δ 9.02 (bs, 1H), 8.36 (d, 1H), 7.71 (m, 1H), 7.40 (m, 1H), 7.30-7.26 (m, 3H), 7.09 (d, 1H), 6.73 (d, 1H), 5.66 (s, 1H), 3.64 (m, 2H), 3.50 (d, 1H), 3.24 (d, 1H), 2.26 (s, 3H) 1.72 (m, 2H), 0.96 (t, 3H). Calculated mass for $C_{22}H_{22}N_2O_3$, 362.16. Observed 385.1 (M+Na).

Example 25

3-(2-(2,6-dimethoxypyridin-3-yl)-2-oxoethyl)-3-hydroxy-5-methyl-1-propylindolin-2-one

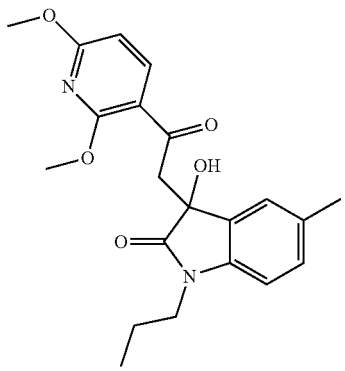

This compound was made in a similar manner to 1-butyl-3-hydroxy-3-(2-oxo-2-(pyridin-2-yl)ethyl)indolin-2-one using 5-methyl-1-propylindoline-2,3-dione and 1-(2,6-dimethoxypyridin-3-yl)ethanone (purchased from Fisher Scientific). 1H-NMR δ 8.14 (d, 1H) 7.23 (s, 1H), 7.08 (d, 1H), 6.76 (d, 1H), 6.36 (d, 1H), 4.67 (s, 1H), 3.99 (d, 6H), 3.69 (d, 1H), 3.66 (m, 2H), 3.47 (d, 1H), 2.29 (s, 3H), 1.75 (m, 2H), 0.98 (t, 3H).

Example 26

3-hydroxy-3-(2-(6-methoxypyridin-2-yl)-2-oxoethyl)-5-methyl-1-propylindolin-2-one

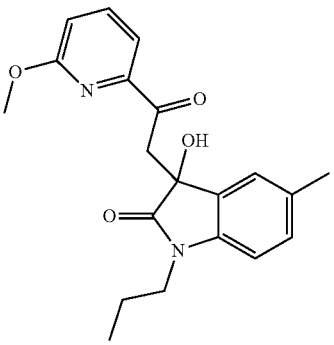

This compound was made in a similar manner to 1-butyl-3-hydroxy-3-(2-oxo-2-(pyridin-2-yl)ethyl)indolin-2-one using 5-methyl-1-propylindoline-2,3-dione and 1-(6-methoxypyridin-2-yl)ethanone (commercially available from Fisher Scientific). 1H-NMR δ 7.74 (m, 2H), 7.19 (s, 1H), 7.11 (d, 1H), 6.98 (d, 1H), 6.77 (d, 1H), 5.27 (bs, 1H), 4.03 (s, 3H), 3.65 (m, 3H), 3.49 (d, 1H), 2.30 (s, 3H), 1.74 (m, 2H), 0.97 (t, 3H).

Example 27

3-(2-(1H-indol-3-yl)-2-oxoethyl)-1-(3-azidopropyl)-3-hydroxy-5-methylindolin-2-one

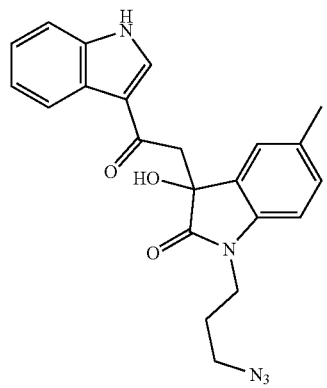 [SMILES: Cc1ccc2c(c1)C(O)(CC(=O)c1c[nH]c3ccccc13)C(=O)N2CCCN=[N+]=[N-]]

To a flame dried flask cooled under argon equipped with a stir bar was added 5-methyl isatin (1.0 grams, 6.2 mmol), potassium carbonate (4.3 grams, 31.0 mmol), sodium iodide (0.93 grams, 6.2 mmol) and 62 mL of DMF (anhydrous, purchased from Fisher Scientific). While stirring at room temperature 1,3 dibromo propane (0.95 mL, 9.3 mmol) was added. Once the reaction had gone to completion, it was filtered then concentrated. It was then taken up in dichloromethane filtered and concentrated. It was then purified using a silica gel support (hexanes/ethyl acetate 8:2) Yield, 14%.

To a flame dried flask cooled under argon equipped with a stir bar was added 1-(3-bromopropyl)-5-methylindoline-2,3-dione (0.244 grams, 0.86 mmol) sodium azide (0.084 grams, 1.29 mmol), and 2.9 mL of DMF (anhydrous, purchased from Fisher Scientific). The stirring solution was then heated to 60° C. and stirred at this temperature in the dark overnight. The next day it was concentrated. It was used the subsequent step without further purification. 1H-NMR δ 7.41 (m, 2H), 6.84 (d, 1H), 3.79 (t, 2H), 3.43 (t, 2H), 2.34 (s, 3H), 1.96 (m, 2H).

To a clean Biotage microwave vial was added 1-(1H-indol-3-yl)ethanone (0.023 grams, 0.143 mmol, purchased from Fisher Scientific), 1-(3-azidopropyl)-5-methylindoline-2,3-dione (0.02 grams, 0.082 mmol) and 0.27 mL of methanol. After the addition of 9.0 μL of dimethyl amine (40% by weight solution in water, purchased from Fisher Scientific), the vial was sealed and heated in a Biotage Initiator for ten minutes at 130° C. It was then concentrated and purified using a Teledyne ISCO hexanes/ethyl acetate gradient on silica gel. A subsequent purification was done using a preparative thin layer chromatography (ethyl acetate, hexanes (2:1)). Yield 14%. 1H-NMR δ 8.87 (bs, 1H), 8.34 (m, 1H), 7.76 (s, 1H), 7.40 (m, 1H), 7.29 (m, 3H), 7.10 (d, 1H), 6.77 (d, 1H), 5.0 (bs, OH), 3.77 (m, 2H), 3.60 (d, 1H), 3.41 (t, 2H), 3.34 (d, 1H), 2.27 (s, 3H), 1.96 (m, 2H).

Example 28

1-(3-azidopropyl)-3-hydroxy-3-(2-(6-methoxypyridin-2-yl)-2-oxoethyl)-5-methylindolin-2-one

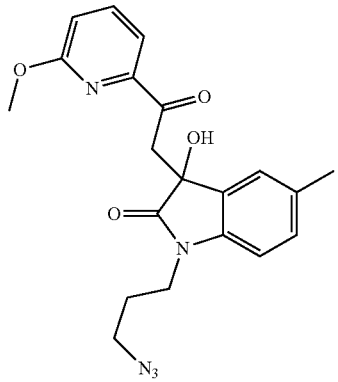

This compound was made in a similar manner to 3-(2-(1H-indol-3-yl)-2-oxoethyl)-1-(3-azidopropyl)-3-hydroxy-5-methylindolin-2-one using 1-(3-azidopropyl)-5-methylindoline-2,3-dione and 1-(6-methoxypyridin-2-yl)ethanone (commercially available from Fisher Scientific). 1H-NMR δ 7.71 (t, 1H), 7.61 (d, 1H), 7.14 (s, 1H), 7.12 (d, 1H), 6.96 (d, 1H), 6.79 (d, 1H), 4.95 (bs, 1H), 4.09 (d, 1H), 3.99 (s, 3H), 3.73 (m, 2H), 3.63 (d, 1H), 3.43 (t, 2H), 2.3 (s, 3H), 1.99 (m, 2H).

Example 29

3-hydroxy-1-isobutyl-3-(2-(6-methoxypyridin-2-yl)-2-oxoethyl)-5-methylindolin-2-one

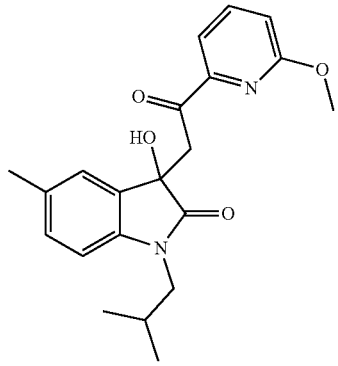

This compound was made in a similar manner to 1-butyl-3-hydroxy-3-(2-oxo-2-(pyridin-2-yl)ethyl)indolin-2-one using 1-isobutyl-5-methylindoline-2,3-dione and commercially available 1-(6-methoxypyridin-2-yl)ethanone (purchased from Fisher Scientific). 1H-NMR δ 7.70 (m, 2H), 7.19 (d, 1H), 7.10 (d, 1H), 6.97 (dd, 1H), 6.75 (d, 1H), 5.39 (s, OH), 4.02-3.98 (m, 4H), 3.56-3.42 (m, 3H), 2.30 (s, 3H), 2.16 (m, 1H), 0.97 (dd, 6H). calculated mass for C21H24N2O4, 368.17, observed, 391.1 (M+Na).

Example 30

5,7-dichloro-3-hydroxy-3-(2-(6-methoxypyridin-2-yl)-2-oxoethyl)-1-propylindolin-2-one

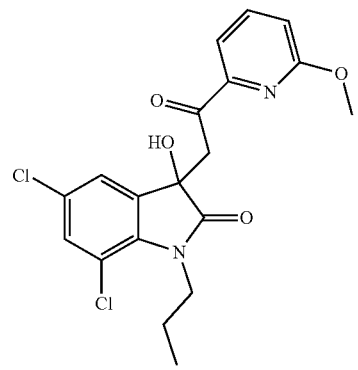 [SMILES: CCCN1C(=O)C(O)(CC(=O)c2cccc(OC)n2)c2cc(Cl)cc(Cl)c21]

This compound was made in a similar manner to 1-butyl-3-hydroxy-3-(2-oxo-2-(pyridin-2-yl)ethyl)indolin-2-one using 5,7-dichloro-1-propylindoline-2,3-dione and 1-isobutyl-5-methylindoline-2,3-dione (purchased from Fisher Scientific). 1H-NMR δ 7.74 (dd, 1H), 7.65 (dd, 1H), 7.37-7.25 (m, 2H), 6.99 (dd, 1H), 5.31 (bs, OH), 4.04-3.96 (m, 6H), 3.53 (dd, 1H), 1.77 (m, 2H), 0.92 (t, 3H).

Example 31

3-(2-(1H-indol-3-yl)-2-oxoethyl)-5-chloro-3-hydroxy-1-propylindolin-2-one

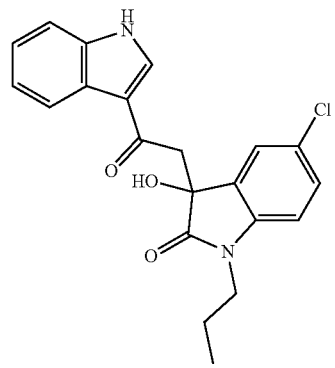 [SMILES: CCCN1C(=O)C(O)(CC(=O)c2c[nH]c3ccccc23)c2cc(Cl)ccc21]

This compound was made in a similar manner to 1-butyl-3-hydroxy-3-(2-oxo-2-(pyridin-2-yl)ethyl)indolin-2-one using 5-chloro-1-propylindoline-2,3-dione and commercially available 1-(1H-indol-3-yl)ethanone (purchased from Fisher Scientific). 1H-NMR δ 8.71 (bs, NH) 8.38 (m, 1H), 7.79 (d, 1H), 7.49 (d, 1H), 7.41 (m, 1H), 7.35-7.31 (m, 2H), 7.26 (m, 1H), 6.78 (d, 1H), 5.00 (bs, OH), 3.65 (m, 2H), 3.50 (d, 1H), 3.25 (d, 1H), 1.69 (m, 2H), 0.96 (t, 3H). calculated mass for C21H19ClN2O3, 382.11, observed, 383.1 (M+1).

Example 32

5-chloro-3-hydroxy-1-isobutyl-3-(2-oxo-2-(pyridin-2-yl)ethyl)indolin-2-one

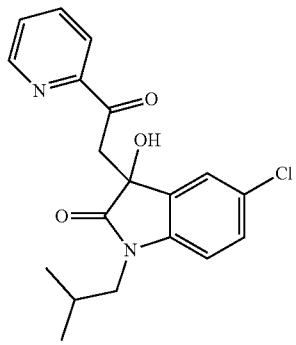 [SMILES: CC(C)CN1C(=O)C(O)(CC(=O)c2ccccn2)c2cc(Cl)ccc21]

This compound was made in a similar manner to 1-butyl-3-hydroxy-3-(2-oxo-2-(pyridin-2-yl)ethyl)indolin-2-one using 5-chloro-1-isobutylindoline-2,3-dione and commercially available 2-acetyl pyridine (purchased from Fisher Scientific). 1H-NMR δ 8.71 (ddd, 1H), 8.13 (dd, 1H), 7.93 (dd, 1H), 7.56 (ddd, 1H), 7.31 (d, 1H), 7.28-7.26 (m, 2H), 6.78 (d, 1H), 3.74 (dd, 1H), 3.56-3.40 (m, 3H), 2.13 (m, 1H), 0.96 (d, 6H). calculated mass for C19H19ClN2O3, 358.11, observed, 359.1 (M+1).

Example 33

1-ethyl-5-methyl-2-oxo-3-(3,4,5-trimethoxybenzyl)indolin-3-yl benzoate

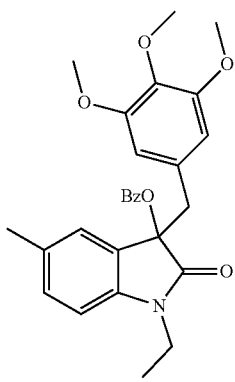 [SMILES: CCN1C(=O)C(O)(Cc2cc(OC)c(OC)c(OC)c2)c2cc(C)ccc21]

To an oven dried flask cooled under argon equipped with a stir bar was added 1-ethyl-5-methyl-2-oxoindolin-3-yl benzoate (0.05 grams, 0.17 mmol, 0.5 M in toluene). While stirring at room temperature LiHMDS (0.3 mL, 0.3 mmol, 1.0 M, purchased from Fisher Scientific) was added. After approximately ten minutes a solution of 3,4,5 trimethoxybenzyl chloride (0.0553 grams, 0.26 mmol, purchased from Aldrich, 0.5 M in anhydrous DMF) was added. The reaction continued to stir overnight. The next day the reaction was acidified with 0.1M HCl, diluted with ethyl acetate and the two layers were separated. The aqueous layer was salted out and washed twice more with ethyl acetate. The combined organic solution was dried with sodium sulfate, filtered and concentrated. Purification was done on a Teledyne ISCO with silica gel using a hexanes/ethyl acetate gradient. This was followed by a subsequent reverse phase purification using Teledyne ISCO with a C18 column and a water with 0.1% formic acid, acetonitrile gradient. Yield (20%) 1H-NMR δ 8.05 (d, 2H), 7.57 (dd, 1H), 7.43 (m, 2H), 7.08 (d, 1H), 6.97 (s, 1H), 6.62 (d, 1H), 6.17 (s, 2H), 3.78 (s, 3H), 3.76 (m, 1H), 3.68 (s, 6H), 3.53 (m, 1H), 3.29 (d, 1H), 3.24 (d, 1H), 2.28 (s, 3H), 1.00 (t, 3H). Calculated mass for C28H29NO6, 475.20. Observed 498.2 (M+Na).

Example 34

1-ethyl-3-hydroxy-5-methyl-3-(3,4,5-trimethoxybenzyl)indolin-2-one

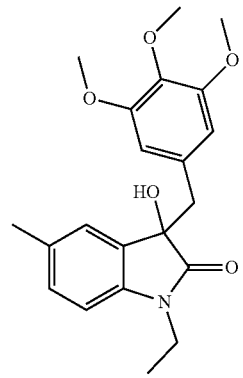

To an oven dried flask cooled under argon equipped with a stir bar was added 1-ethyl-5-methyl-2-oxoindolin-3-yl benzoate (0.05 grams, 0.17 mmol, 0.5 M in toluene). While stirring at room temperature LiHMDS (0.3 mL, 0.3 mmol, 1.0 M, purchased from Fisher Scientific) was added. After approximately ten minutes a solution of 3,4,5 trimethoxybenzyl chloride (0.0553 grams, 0.26 mmol, purchased from Aldrich, 0.5 M in anhydrous DMF) was added. The reaction continued to stir overnight. The next day the reaction was acidified with 0.1 M HCl, diluted with ethyl acetate and the two layers were separated. The aqueous layer was salted out and washed twice more with ethyl acetate. The combined organic solution was dried with sodium sulfate, filtered and concentrated. Purification was done on a Teledyne ISCO with silica gel using a hexanes ethyl acetate gradient. This was followed by a subsequent reverse phase purification using Teledyne ISCO with a C18 column and a water with 0.1% formic acid, acetonitrile gradient. Yield (17%) 1H NMR δ 7.22 (s, 1H), 7.08 (d, 1H), 6.55 (d, 1H), 6.06 (s, 2H), 4.83 (bs, OH), 3.72 (s, 3H), 3.66 (m, 1H), 3.61 (s, 6H), 3.34 (m, 1H), 3.23 (d, 1H), 3.17 (d, 1H), 2.35 (s, 3H), 0.87 (t, 3H). Calculated mass for C21H25NO5, 371.43. Observed 394.1 (M+Na).

Alternative route: To an oven dried Biotage microwave vial cooled under argon was added 1-ethyl-5-methyl-2-oxo-3-(3,4,5-trimethoxybenzyl)indolin-3-yl benzoate (0.053 grams, 0.11 mmol). This was taken up in 0.6 mL of methanol, 0.6 mL of deionized water. A solution of KOH (223 μl, 2.0M in water) was added and the sealed vial was placed in the microwave and heated to 130° C. for 12 minutes, and 18 minutes at 140° C. Upon cooling the solution was neutralized with a stoichiometric amount of glacial acetic acid (Fisher scientific), and concentrated. Purification on a Teledyne ISCO using a C18 reverse phase column (water with 0.1% formic acid/acetonitrile gradient) afforded the desired compound. 85% yield. 1H NMR δ 7.22 (s, 1H), 7.08 (d, 1H), 6.55 (d, 1H), 6.06 (s, 2H), 4.38 (bs, OH), 3.72 (s, 3H), 3.66 (m, 1H), 3.61 (s, 6H), 3.34 (m, 1H), 3.23 (d, 1H), 3.17 (d, 1H), 2.35 (s, 3H), 0.87 (t, 3H). Calculated mass for C21H25NO5, 371.43. Observed 394.1 (M+Na)

Example 35

5-chloro-1-isobutyl-2-oxo-3-(3,4,5-trimethoxybenzyl)indolin-3-yl benzoate

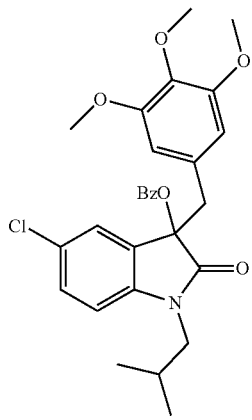

This compound was prepared in an analogous fashion to 1-ethyl-5-methyl-2-oxo-3-(3,4,5-trimethoxybenzyl)indolin-3-yl benzoate using 5-chloro-1-isobutyl-2-oxoindolin-3-yl benzoate. 1H NMR δ 8.05 (d, 2H), 7.59 (t, 1H), 7.44 (t, 2H), 7.25 (m, 1H), 7.1 (s, 1H), 6.68 (d, 1H), 6.21 (s, 2H), 3.79 (s, 3H), 3.71 (S, 6H), 3.48 (m, 2H), 3.27 (m, 2H), 1.98 (m, 1H), 0.82 (dd, 6H). Calculated mass for C29H30ClNO6, 523.18. Observed 566.2 (M+Na).

Example 36

1-isobutyl-5-methyl-2-oxo-3-(3,4,5-trimethoxybenzyl)indolin-3-yl benzoate

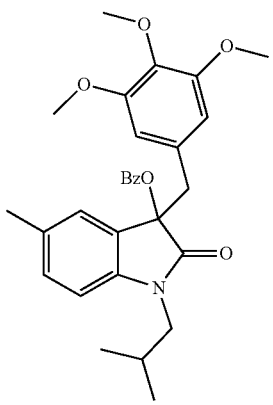

This compound was made in an analogous fashion to 1-ethyl-5-methyl-2-oxo-3-(3,4,5-trimethoxybenzyl)indolin-3-yl benzoate using 1-isobutyl-5-methyl-2-oxoindolin-3-yl benzoate. 1H-NMR δ 8.05 (d, 2H), 7.57 (dd, 1H), 7.43 (m, 2H), 7.07 (d, 1H), 6.96 (s, 1H), 6.63 (d, 1H), 6.19 (s, 2H), 3.79 (s, 3H), 3.68 (s, 6H), 3.49 (m, 2H), 3.25 (m, 2H), 2.28 (s, 3H), 1.97 (m, 1H), 0.82 (dd, 6H). Calculated mass for C30H33NO6, 503.23. Observed 526.3 (M+Na).

Example 37

3-hydroxy-1-isobutyl-5-methyl-3-(3,4,5-trimethoxybenzyl)indolin-2-one

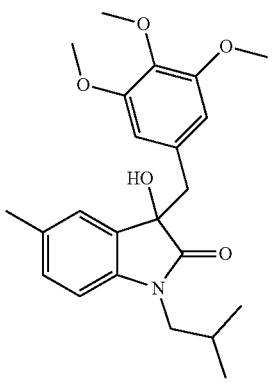

This compound was made in an analogous fashion to 1-ethyl-3-hydroxy-5-methyl-3-(3,4,5-trimethoxybenzyl)indolin-2-one using 5-methyl-1-isobutyl-2-oxoindolin-3-yl benzoate. 1H-NMR δ 7.22 (s, 1H), 7.08 (d, 1H), 6.58 (d, 2H), 6.1 (s, 2H), 3.74 (s, 3H), 3.63 (s, 6H), 3.48 (m, 1H), 3.29 (d, 1H), 3.11 (m, 1H), 3.06 (bs, OH), 2.35 (s, 3H), 1.85 (m, 1H), 0.70 (dd, 6H). Calculated mass for C23H29NO5, 398.49. Observed 422.0 (M+Na).

Example 38

3-(3,5-dimethoxybenzyl)-1-ethyl-5-methyl-2-oxoindolin-3-yl benzoate

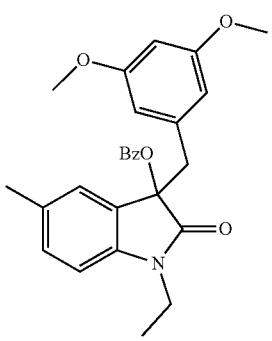

This compound was made in an analogous fashion to 1-ethyl-5-methyl-2-oxo-3-(3,4,5-trimethoxybenzyl)indolin-3-yl benzoate using 1-ethyl-5-methyl-2-oxoindolin-3-yl benzoate and 3,5-dimethoxy benzyl bromide (purchased from Fisher Scientific). 1H NMR δ 8.08 (d, 2H), 7.60 (t, 1H), 7.57 (t, 2H), 7.10 (d, 1H), 6.90 (s, 1H), 6.65 (d, 1H), 6.33 (s, 1H), 6.18 (s, 2H), 3.79 (m, 1H), 3.62 (s, 6H), 3.59 (m, 1H), 3.52 (d, 1H), 3.22 (d, 1H), 2.28 (s, 3H), 1.07 (t, 3H). Calculated mass for C27H27NO5, 445.19. Observed 468.2 (M+Na).

Example 39

3-(3,5-dimethoxybenzyl)-5-methyl-2-oxo-1-phenethylindolin-3-yl benzoate

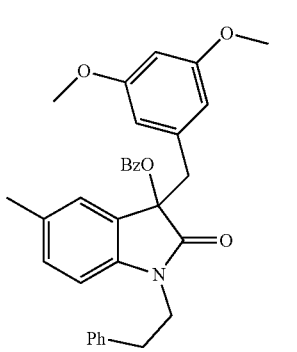

This compound was made in an analogous fashion to 1-ethyl-5-methyl-2-oxo-3-(3,4,5-trimethoxybenzyl)indolin-3-yl benzoate. 1H-NMR δ 8.07 (d, 2H), 7.57 (t, 1H), 7.44 (t, 2H), 7.25 (m, 5H), 7.05 (d, 1H), 6.84 (s, 1H), 6.55 (d, 1H), 6.32 (s, 1H), 6.19 (s, 2H) 3.95 (m, 1H), 3.72 (m, 1H), 3.66 (s, 6H), 3.49 (d, 1H), 3.11 (d, 1H), 2.75 (t, 2H), 2.25 (s, 3H). Calculated mass for C33H31NO5, 521.22. Observed 544.1 (M+Na).

Example 40

5-chloro-1-ethyl-3-(3-methoxybenzyl)-2-oxoindolin-3-yl benzoate

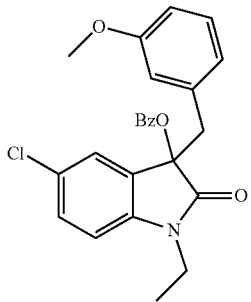

This compound was made in an analogous fashion to 1-ethyl-5-methyl-2-oxo-3-(3,4,5-trimethoxybenzyl)indolin-3-yl benzoate using 5-chloro-1-ethyl-2-oxoindolin-3-yl benzoate and 3-methoxy benzyl chloride (purchased from Fisher Scientific). 1H NMR δ 8.06 (d, 2H), 7.61 (t, 1H), 7.46 (t, 2H), 7.25 (dd, 1H), 7.09 (t, 1H), 7.02 (d, 1H), 6.76 (dd, 1H), 6.64 (m, 2H), 6.52 (s, 1H), 3.72 (m, 4H), 3.57 (m, 2H), 3.27 (d, 1H), 1.04 (t, 3H). Calculated mass for C25H22NClO4, 435.12. Observed 458.1 (M+Na).

Example 41

1-butyl-5-chloro-3-(3,5-dimethoxybenzyl)-3-hydroxyindolin-2-one

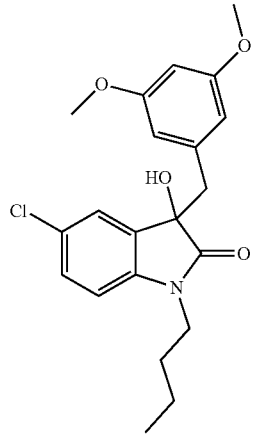 [SMILES: CCCCN1C(=O)C(O)(Cc2cc(OC)cc(OC)c2)c2cc(Cl)ccc21]

This compound was made in an analogous fashion to 1-ethyl-3-hydroxy-5-methyl-3-(3,4,5-trimethoxybenzyl)indolin-2-one using 1-butyl-5-chloro-2-oxoindolin-3-yl benzoate and 3,5-dimethoxy benzyl bromide (purchased from Fisher Scientific). 1H NMR δ 7.25 (m, 2H) 6.61 (d, 1H), 6.24 (s, 1H), 6.06 (s, 2H), 3.66 (m, 7H), 3.23 (m, 2H), 3.16 (d, 1H), 1.63 (bs, OH), 1.35 (m, 2H), 1.17 (m, 2H), 0.96 (t, 3H). Calculated mass for C21H24ClNO4, 389.14. Observed 412.2 (M+Na).

Example 42

1-butyl-5-chloro-3-hydroxy-3-(3-methoxybenzyl)indolin-2-one

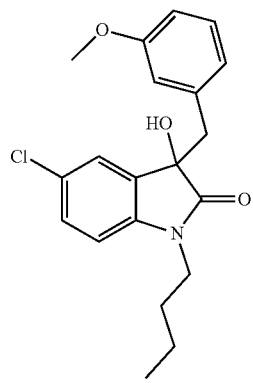 [SMILES: CCCCN1C(=O)C(O)(Cc2cccc(OC)c2)c2cc(Cl)ccc21]

This compound was made in an analogous fashion to 11-ethyl-3-hydroxy-5-methyl-3-(3,4,5-trimethoxybenzyl)indolin-2-one using 1-butyl-5-chloro-3-(3,5-dimethoxybenzyl)-3-hydroxyindolin-2-one and 3-methoxy benzyl chloride (purchased from Fisher Scientific). 1H NMR δ 7.31 (s, 1H), 7.24 (d, 1H), 7.02 (t, 1H), 6.69 (d, 1H), 6.59 (d, 1H), 6.52 (d, 1H), 6.43 (s, 1H), 3.64 (m, 4H), 3.30 (m, 2H), 3.20 (d, 1H), 1.6 (bs, OH), 1.30 (m, 2H), 1.11 (m, 2H), 0.84 (t, 3H). Calculated mass for C20H22ClNO3, 359.13. Observed 382.2 (M+Na).

Example 43

3-hydroxy-3-(3-methoxybenzyl)-5-methyl-1-propylindolin-2-one

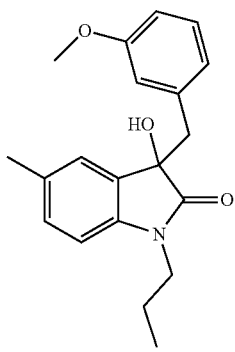 [SMILES: CCCN1C(=O)C(O)(Cc2cccc(OC)c2)c2cc(C)ccc21]

This compound was made in an analogous fashion to 11-ethyl-3-hydroxy-5-methyl-3-(3,4,5-trimethoxybenzyl)indolin-2-one using 5-methyl-2-oxo-1-propylindolin-3-yl benzoate and 3-methoxy benzyl chloride (purchased from Fisher Scientific). 1H NMR δ 7.12 (s, 1H), 7.04 (m, 2H), 6.69 (d, 1H), 6.55 (t, 2H), 6.43 (s, 1H), 3.61 (m, 4H), 3.29 (m, 2H), 3.16 (d, 1H), 2.89 (bs, OH), 2.32 (s, 3H), 1.39 (m, 2H), 0.74 (t, 3H). Calculated mass for C20H23NO3, 325.17. Observed 348.1 (M+Na).

Example 44

3-(3,4-dimethoxybenzyl)-5-methyl-2-oxo-1-phenethylindolin-3-yl benzoate

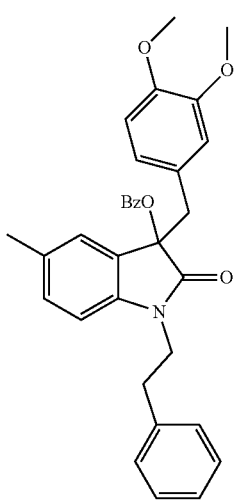

This compound was made in an analogous fashion to 1-ethyl-5-methyl-2-oxo-3-(3,4,5-trimethoxybenzyl)indolin-3-yl benzoate using 5-methyl-2-oxo-1-phenethylindolin-3-yl benzoate and 4-(bromomethyl)-1,2-dimethoxybenzene. 1H-NMR δ 8.07 (d, 2H), 7.58 (t, 1H), 7.46 (t, 2H), 7.27 (m, 4H), 7.04 (d, 1H), 6.88 (s, 1H), 6.67 (dd, 2H), 6.52 (d, 2H), 6.40 (s, 1H), 3.88 (m, 1H), 3.81 (s, 3H), 3.72 (m, 1H), 3.70 (s, 3H), 3.49 (d, 1H), 3.17 (d, 1H), 2.74 (t, 2H), 2.26 (s, 3H). Calculated mass for C33H31NO5, 521.22. Observed 544.2 (M+Na).

Example 45

3-(3,4-dimethoxybenzyl)-1-isopentyl-2-oxoindolin-3-yl benzoate

This compound was made in an analogous fashion to 1-ethyl-5-methyl-2-oxo-3-(3,4,5-trimethoxybenzyl)indolin-3-yl benzoate using 1-isopentyl-2-oxoindolin-3-yl benzoate and 4-(bromomethyl)-1,2-dimethoxybenzene. 1H-NMR δ 8.06 (d, 2H), 7.55 (t, 1H), 7.43 (t, 2H), 7.29 (t, 1H), 7.13 (d, 1H), 7.01 (t, 1H), 6.69 (t, 2H), 6.61 (d, 1H) 6.34 (s, 1H), 3.82 (s, 3H) 3.63 (m, 4H), 3.49 (m, 2H), 3.28 (d, 1H), 1.51 (m, 1H), 1.51 (q, 2H), 0.92 (dd, 6H). Calculated mass for C29H31NO5, 473.22. Observed 496.2 (M+Na).

Example 46

3-(3,4-dimethoxybenzyl)-1-isopentyl-5-methyl-2-oxoindolin-3-yl benzoate

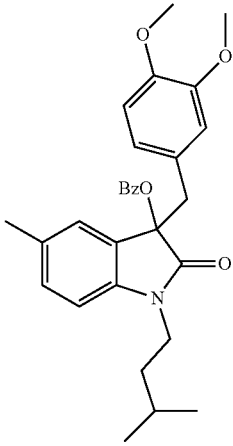

This compound was made in an analogous fashion to 1-ethyl-5-methyl-2-oxo-3-(3,4,5-trimethoxybenzyl)indolin-3-yl benzoate using 1-isopentyl-5-methyl-2-oxoindolin-3-yl benzoate and 4-(bromomethyl)-1,2-dimethoxybenzene. 1H-NMR δ 8.06 (d, 2H), 7.57 (t, 1H), 7.43 (t, 2H), 7.08 (d, 1H), 6.93 (s, 1H), 6.67 (d, 1H), 6.60 (t, 2H), 6.36 (s, 1H), 3.82 (s, 3H), 3.64 (m, 4H), 3.46 (m, 2H), 3.26 (d, 1H), 2.27 (s, 3H), 1.50 (m, 1H), 1.26 (m, 2H) 0.92 (dd, 6H). Calculated mass for C30H33NO5, 487.24. Observed 510.2 (M+Na).

Example 47

3-(3,4-dimethoxybenzyl)-5-methyl-2-oxo-1-propylindolin-3-yl benzoate

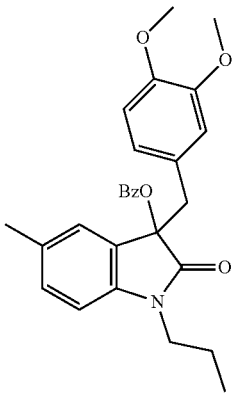

This compound was made in an analogous fashion to 1-ethyl-5-methyl-2-oxo-3-(3,4,5-trimethoxybenzyl)indolin-3-yl benzoate using 5-methyl-2-oxo-1-propylindolin-3-yl benzoate and 4-(bromomethyl)-1,2-dimethoxybenzene. 1H-NMR δ 8.06 (d, 2H), 7.57 (t, 1H), 7.43 (t, 2H), 7.07 (d, 1H), 6.90 (s, 1H), 6.68 (d, 1H) 6.62 (m, 2H), 6.39 (s, 1H), 3.83 (s, 3H), 3.66 (s, 3H), 3.56 (m, 1H) 3.47 (m, 2H), 3.25 (d, 1H), 2.27 (s, 3H), 1.52 (m, 2H), 0.84 (t, 3H). Calculated mass for C28H29NO5, 459.53. Observed 482.2 (M+Na).

Example 48

3-hydroxy-1-isobutyl-3-(3,4,5-trimethoxybenzyl)indolin-2-one

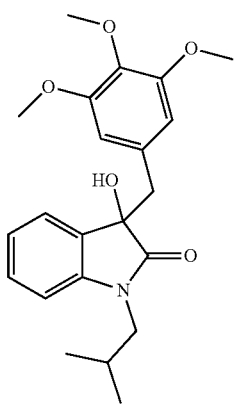 [SMILES: COc1cc(CC2(O)C(=O)N(CC(C)C)c3ccccc32)cc(OC)c1OC]

This compound was made in an analogous fashion to 11-ethyl-3-hydroxy-5-methyl-3-(3,4,5-trimethoxybenzyl)indolin-2-one using 1-isobutyl-2-oxoindolin-3-yl benzoate. 1H-NMR δ 7.41 (d, 1H), 7.30 (m, 1H), 7.11 (dd, 1H), 6.69 (d, 1H), 6.09 (s, 2H), 3.74 (s, 3H), 3.62 (s, 6H), 3.49 (dd, 1H), 3.30 (d, 1H), 3.14 (d, 1H), 3.10 (dd, 1H), 2.88 (bs, OH), 1.85 (m, 1H), 0.71 (dd, 6H). Calculated mass for C22H27NO5, 385.19. Observed 408.2 (M+Na).

Example 49

1-isobutyl-2-oxo-3-(3,4,5-trimethoxybenzyl)indolin-3-yl benzoate

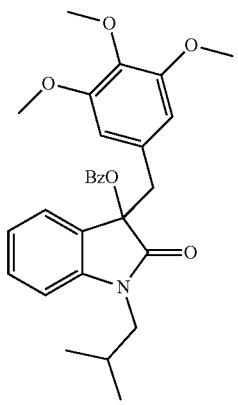

This compound was made in an analogous fashion to 1-ethyl-5-methyl-2-oxo-3-(3,4,5-trimethoxybenzyl)indolin-3-yl benzoate using 1-isobutyl-2-oxoindolin-3-yl benzoate. 1H-NMR δ 8.05 (d, 2H), 7.57 (dd, 1H), 7.43 (dd, 2H), 7.27 (m, 1H), 7.17 (d, 1H), 7.01 (dd, 1H), 6.73 (d, 1H), 6.17 (2H), 3.78 (s, 3H), 3.66 (s, 6H), 3.51 (m, 2H), 3.25 (m, 2H), 1.97 (m, 1H), 0.82 (dd, 6H). Calculated mass for C29H31NO6, 489.22. Observed 512.3 (M+Na).

Example 50

5-chloro-2-oxo-1-phenethyl-3-(3,4,5-trimethoxybenzyl)indolin-3-yl benzoate

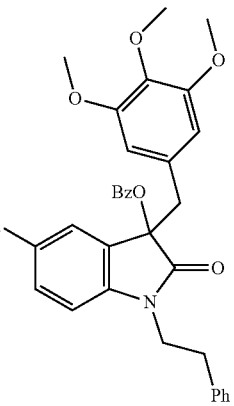

This compound was made in an analogous fashion to 1-ethyl-5-methyl-2-oxo-3-(3,4,5-trimethoxybenzyl)indolin-3-yl benzoate using 5-chloro-2-oxo-1-phenethylindolin-3-yl benzoate. 1H-NMR δ 8.05 (d, 2H), 7.57 (dd, 1H), 7.43 (dd, 2H), 7.29 (m, 1H), 7.24-7.05 (m, 6H), 7.05 (d, 1H), 6.49 (d, 1H), 6.24 (s, 2H), 3.95 (m, 1H), 3.81-3.71 (m, 10H), 3.46 (d, 1H), 3.12 (d, 1H), 2.76 (t, 2H). Calculated mass for C33H30ClNO6, 571.18. Observed 594.3 (M+Na).

Example 51

1-ethyl-3-hydroxy-3-(4-methoxybenzyl)-5-methylindolin-2-one

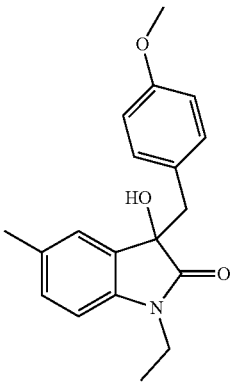 [SMILES: CCN1C(=O)C(O)(Cc2ccc(OC)cc2)c2cc(C)ccc21]

This compound was made in an analogous fashion to 11-ethyl-3-hydroxy-5-methyl-3-(3,4,5-trimethoxybenzyl)indolin-2-one using 1-ethyl-5-methyl-2-oxoindolin-3-yl benzoate: and 4-methoxy benzyl chloride (purchased from Fisher Scientific). 1H-NMR δ 7.11 (s, 1H), 7.05 (dd, 1H), 6.83 (d, 2H), 6.65 (d, 2H), 6.56 (d, 1H), 3.72 (s, 3H), 3.64 (m, 1H), 3.40 (m, 1H), 3.24 (d, 1H), 3.12 (d 1H), 2.34 (s, 3H), 2.0 (bs, OH), 0.94 (t, 3H). Calculated mass for C19H21NO3, 311.15. Observed 334.1 (M+Na).

Example 52

3-(2-hydroxy-4-methoxybenzyl)-2-oxo-1-propylindolin-3-yl benzoate

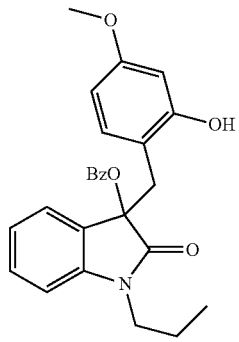

To a flame dried flask cooled under argon was added the 2-oxo-1-propylindolin-3-yl benzoate (0.1 grams, 0.3 mmol, 0.5 M in toluene). While stirring at −78° C. a solution of LiHMDS (0.33 mL, 1.0M) was added. The solution was then warmed to 0° C.

In a separate flame dried flask that had been cooled under argon was added tert-butyl (2-(hydroxymethyl)-4-methoxyphenyl) carbonate (0.02 grams, 0.078 mmol, 0.1M in THF). The stirring solution was cooled to −78° C. While stirring at this temperature MeMgCl (60 µL, 1.4M, purchased from Aldrich) was added.

After fifteen minutes the lithiated 2-oxo-1-propylindolin-3-yl benzoate solution was added to the tert-butyl (2-(hydroxymethyl)-5-methoxyphenyl) carbonate solution at 0° C. The reaction continued to stir warming up to room temperature overnight. The next day the reaction was quenched upon the addition of ammonium chloride (saturated). The two layers were separated. The aqueous layer was washed three times with dichloromethane. The combined organic material was dried with sodium sulfate, filtered and concentrated. Chromatography using a Teledyne ISCO on basic alumina (hexanes/ethyl acetate) afforded the desired compound. Further purification using preparative thin layer chromatography (hexanes/ethyl acetate 2:1) afforded the desired compound. (18% yield). 1H-NMR δ 8.02 (dd, 2H), 7.57 (t, 1H), 7.45 (dd, 2H), 7.30 (dd, 1H), 7.22 (d, 1H), 6.79 (d, 1H), 6.48 (m, 2H), 6.24 (dd, 1H), 6.23 (bs, OH), 3.72 (s, 3H), 3.71 (m, 1H), 3.51 (m, 2H), 3.44 (m, 2H), 1.53 (m, 2H), 0.82 (t, 3H).

Example 53

3-(2-hydroxy-4-methoxybenzyl)-5-methyl-1-(4-methylpentyl)-2-oxoindolin-3-yl benzoate

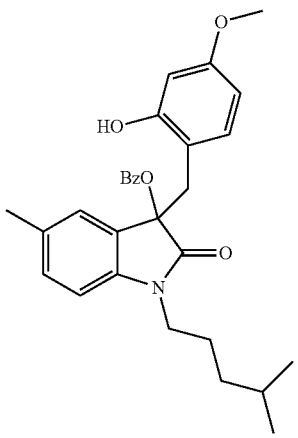

This compound was prepared in a similar manner by reacting 5-methyl-1-(4-methylpentyl)-2-oxoindolin-3-yl benzoate and tert-butyl (2-(hydroxymethyl)-5-methoxyphenyl) carbonate. 1H-NMR δ 8.08 (dd, 2H), 7.57 (dd, 1H), 7.45 (dd, 2H), 7.11 (d, 1H), 7.08 (s, 1H), 6.67 (d, 1H), 6.48 (d, 1H), 6.42 (d, 1H), 6.41 (bs, OH), 6.23 (dd, 1H), 3.75-3.68 (m, 4H), 3.52 (d, 1H), 3.42 (m, 1H), 3.39 (d, 1H), 2.32 (s, 3H), 1.48 (m, 1H), 1.36 (m, 2H), 1.1 (m, 2H), 0.85 (dd, 6H). Calculated mass for C30H33NO5, 487.24. Observed 510.3 (M+Na).

Alternative coupling: To an oven dried flask equipped with a stir bar that was cooled under argon was added 5-methyl-1-(4-methylpentyl)-2-oxoindolin-3-yl benzoate (0.0843 grams, 0.24 mmol, 0.5 M in toluene). While stirring at room temperature a solution of LiHMDS (0.50 mL, 1.0M) was added all at once.

In a separate oven dried flask that cooled under argon was added the tert-butyl (2-(hydroxymethyl)-4-methoxyphenyl) carbonate (0.03 grams, 0.12 mmol, 0.2M in anhydrous THF). After ten minutes of stirring at room temperature the solution of tert-butyl (2-(hydroxymethyl)-4-methoxyphenyl) carbonate was added all at once to the stirring solution of 5-methyl-1-(4-methylpentyl)-2-oxoindolin-3-yl benzoate. The reaction continued to stir at room temperature overnight. The next day, it was quenched with 0.1 M HCl, diluted with ethyl acetate and the organic layer collected and set aside. The aqueous layer was washed another time with ethyl acetate and the organic material combined. The aqueous layer was then salted out using sodium chloride, and washed with ethyl acetate twice more. The combined organic material was dried with sodium sulfate and concentrated. Purification was done on a Teledyne ISCO using hexanes and ethyl acetate on a silica gel support. A reverse phase run was also performed on a Teledyne ISCO using a C18 column using water with 0.1% formic acid and acetonitrile. This affords 0.02 grams of the desired product. Isolated yield, 35%. 1H-NMR δ 8.05 (m, 2H), 7.59 (t, 7.44 Hz, 1H), 7.45 m, 2H), 7.14 (m, 2H), 6.84 (d, 8.76 Hz, 1H), 6.57 (m, 2H), 6.03 (s, 1H), 5.86 (bs, OH), 3.68 (m, 2H), 3.48 (s, 3H), 3.38 (m, 2H), 2.33 (s, 3H), 1.49 (septet, 6.64 Hz, 1H), 1.29 (m, 2H), 1.09 (m, 2H), 0.85 (d, 6.64 Hz, 6H). calculated mass for C30H33NO5, 487.24. Observed, 510.3 (M+Na).

Example 54

3-(2-hydroxy-5-methoxybenzyl)-1-isobutyl-2-oxoindolin-3-yl benzoate

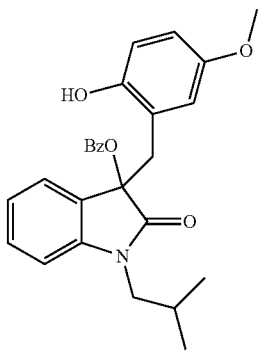

This compound was prepared in a similar manner to 3-(2-hydroxy-4-methoxybenzyl)-5-methyl-1-(4-methylpentyl)-2-oxoindolin-3-yl benzoate using 1-isobutyl-2-oxoindolin-3-yl benzoate reacting with tert-butyl (2-(hydroxymethyl)-4-methoxyphenyl) carbonate. 1H-NMR δ 8.04 (d, 2H), 7.57 (dd, 1H), 7.44 (dd, 2H), 7.34-7.30 (m, 2H), 7.09 (dd, 1H), 6.83 (d, 1H), 6.79 (d, 1H), 6.65 (dd, 1H), 6.06 (d, 1H), 5.81 (s, OH), 3.65 (d, 1H), 3.52 (dd, 1H), 3.44 (s, 3H), 3.42 (d, 1H), 3.27 (dd, 1H), 1.98 (m, 1H), 0.8 (dd, 6H). Calculated mass for C27H27NO5, 445.19. Observed 468.1 (M+Na).

Example 55

5-chloro-3-(2-hydroxy-3-methoxybenzyl)-1-isopentyl-2-oxoindolin-3-yl benzoate

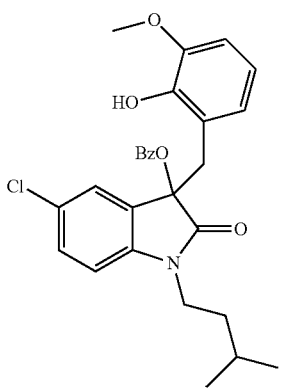

This compound was prepared in a similar manner to 3-(2-hydroxy-4-methoxybenzyl)-5-methyl-1-(4-methylpentyl)-2-oxoindolin-3-yl benzoate by reacting 5-chloro-1-isopentyl-2-oxoindolin-3-yl benzoate with tert-butyl (2-(hydroxymethyl)-6-methoxyphenyl) carbonate. 1H-NMR δ 8.08 (d, 2H), 7.57 (dd, 1H), 7.45 (dd, 2H), 7.20 (dd, 1H), 6.88 (d, 1H), 6.82 (m, 1H), 6.79 (m, 2H), 6.67 (d, 1H), 5.6 (s, OH), 3.84 (s, 3H), 3.79-3.61 (m, 3H), 3.34 (d, 1H), 1.63 (m, 1H), 1.47 (m, 2H), 0.99 (dd, 6H). Calculated mass for C28H28ClNO5, 493.17. Observed 516.2 (M+Na).

Example 56

5-chloro-3-(2-hydroxy-4-methoxybenzyl)-1-(3-morpholinopropyl)-2-oxoindolin-3-yl benzoate

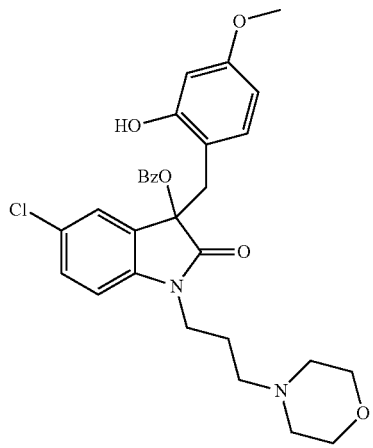

This compound was prepared in a similar manner to 3-(2-hydroxy-4-methoxybenzyl)-5-methyl-1-(4-methylpentyl)-2-oxoindolin-3-yl benzoate by reacting 5-chloro-1-(3-morpholinopropyl)-2-oxoindolin-3-yl benzoate with tert-butyl (2-(hydroxymethyl)-5-methoxyphenyl) carbonate. 1H-NMR δ 8.02 (dd, 2H), 7.58 (dd, 1H), 7.45 (dd, 2H), 7.26 (m, 1H), 7.22 (d, 1H), 6.87 (d, 1H), 6.51 (d, 1H), 6.42 (d, 1H), 6.26 (dd, 1H), 3.73-3.70 (m, 8H), 3.62 (m, 1H), 3.54-3.50 (2H), 3.39 (d, 1H), 2.37-2.15 (m, 6H), 1.78 (m, 2H). Calculated mass for C30H31ClN2O6, 550.19. Observed 551.1 (M+1).

Example 57

1-ethyl-3-(2-hydroxy-4-methoxybenzyl)-2-oxoindolin-3-yl benzoate

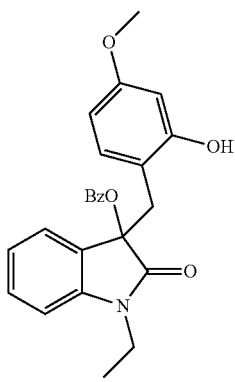

This compound was prepared in a similar manner to 3-(2-hydroxy-4-methoxybenzyl)-5-methyl-1-(4-methylpentyl)-2-oxoindolin-3-yl benzoate by reacting 1-ethyl-2-oxoindolin-3-yl benzoate with tert-butyl (2-(hydroxymethyl)-5-methoxyphenyl) carbonate. 1H-NMR δ 8.04 (d, 2H), 7.6 (t, 1H), 7.43 (t, 2H), 7.30 (t, 1H), 7.25 (d, 1H), 7.08 (t, 1H), 6.78 (d, 1H), 6.47 (m, 2H), 6.24 (dd, 1H), 6.15 (bs, OH), 3.83 (m, 1H), 3.71 (s, 3H), 3.61 (m, 1H), 3.48 (d, 1H), 3.43 (d, 1H), 1.02 (t, 3H). Calculated mass for C25H23NO5, 417.16. Observed 440.0 (M+Na).

Example 58

3-(2-hydroxy-5-methoxybenzyl)-5-methyl-1-(4-methylpentyl)-2-oxoindolin-3-yl benzoate

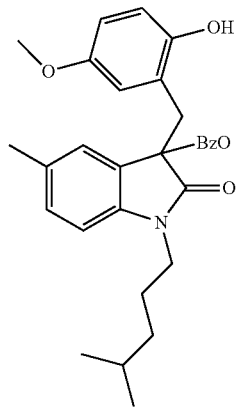

This compound was prepared in a similar manner to 3-(2-hydroxy-4-methoxybenzyl)-5-methyl-1-(4-methylpentyl)-2-oxoindolin-3-yl benzoate by reacting 5-methyl-1-(4-methylpentyl)-2-oxoindolin-3-yl benzoate with tert-butyl (2-(hydroxymethyl)-4-methoxyphenyl) carbonate. 1H-NMR δ 8.06 (d, 2H), 7.58 (t, 1H), 7.45 (t, 2H), 7.13 (d, 2H), 6.85 (d, 1H), 6.65 (m, 2H), 6.02 (bs, H), 5.88 (bs, OH), 3.70 (m, 2H), 3.47 (s, 3H), 3.38 (m, 2H), 2.32 (s, 3H), 1.48 (m, 1H), 1.27 (m, 2H), 1.12 (m, 2H), 0.84 (d, 6H). Calculated mass for C30H33NO5, 487.24, observed, 510.3 (M+Na).

Example 59

5-chloro-1-ethyl-3-(2-hydroxy-3-methoxybenzyl)-2-oxoindolin-3-yl benzoate

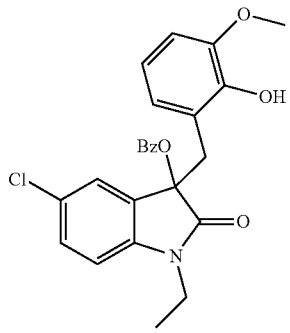

This compound was prepared in a similar manner to 3-(2-hydroxy-4-methoxybenzyl)-5-methyl-1-(4-methylpentyl)-2-oxoindolin-3-yl benzoate by reacting 5-chloro-1-ethyl-2-oxoindolin-3-yl benzoate with tert-butyl (2-(hydroxymethyl)-6-methoxyphenyl) carbonate. 1H-NMR δ 8.07 (d, 2H), 7.59 (t, 1H), 7.44 (t, 2H), 7.21 (d, 1H), 6.9 (s, 1H), 6.79 (m, 1H), 6.69 (d, 2H), 6.52 (d, 1H), 5.57 (bs, OH), 3.84 (s, 3H), 3.74 (m, 2H), 3.63 (d, 1H), 3.34 (d, 1H), 1.19 (t, 3H). Calculated mass for C25H22ClNO5, 451.12, observed, 474.1 (M+Na).

Example 60

1-ethyl-3-(2-hydroxy-5-methoxybenzyl)-5-methyl-2-oxoindolin-3-yl benzoate

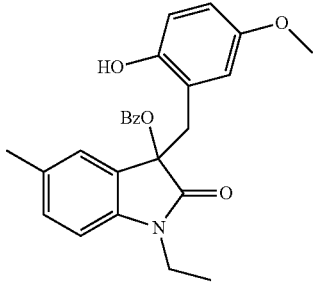

This compound was prepared in a similar manner to 3-(2-hydroxy-4-methoxybenzyl)-5-methyl-1-(4-methylpentyl)-2-oxoindolin-3-yl benzoate by reacting 1-ethyl-5-methyl-2-oxoindolin-3-yl benzoate with tert-butyl (2-(hydroxymethyl)-4-methoxyphenyl) carbonate. 1H-NMR δ 8.05 (d, 2H), 7.58 (t, 1H), 7.45 (t, 2H), 7.13 (m, 2H), 6.8 (d, 1H), 6.65 (m, 2H), 6.03 (d, 1H), 5.87 (bs, OH), 3.78 (m, 1H), 3.67 (d, 1H), 3.52 (m, 1H), 3.39 (s, 3H), 3.29 (d, 1H), 2.32 (s, 3H), 0.92 (t, 3H). Calculated mass for C26H25NO5 431.17. Observed 454.1 (M+Na).

Example 61

5-chloro-3-(2-hydroxy-5-methoxybenzyl)-2-oxo-1-phenethylindolin-3-yl benzoate

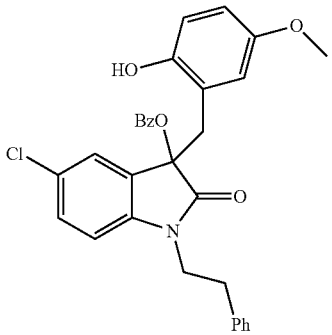

This compound was prepared in a similar manner to 3-((2-hydroxy-4-methoxybenzyl)-5-methyl-1-(4-methylpentyl)-2-oxoindolin-3-yl benzoate by reacting 5-chloro-2-oxo-1-phenethylindolin-3-yl benzoate with tert-butyl (2-(hydroxymethyl)-4-methoxyphenyl) carbonate. 1H-NMR δ 8.06 (d, 2H), 7.60 (t, 1H), 7.48 (t, 2H), 7.25 (m, 5H), 7.09 (d, 2H), 6.82 (d, 1H), 6.70 (dd, 1H), 6.45 (d, 1H), 6.23 (d, 1H), 5.70 (bs, OH), 3.99 (m, 1H), 3.70 (m, 1H), 3.58 (s, 3H), 3.48 (d, 1H), 3.44 (d, 1H) 2.71 (m, 2H). Calculated mass for C31H26ClNO5, 527.15. Observed 550.1 (M+Na).

Example 62

5-chloro-1-ethyl-3-(2-hydroxy-5-methoxybenzyl)-2-oxoindolin-3-yl benzoate

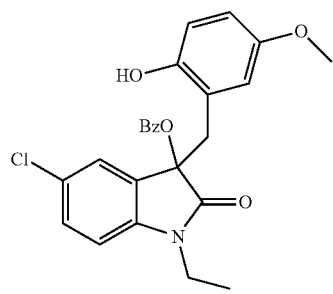

This compound was prepared in a similar manner to 3-(2-hydroxy-4-methoxybenzyl)-5-methyl-1-(4-methylpentyl)-2-oxoindolin-3-yl benzoate by reacting 5-chloro-1-ethyl-2-oxoindolin-3-yl benzoate with tert-butyl (2-(hydroxymethyl)-4-methoxyphenyl) carbonate. 1H-NMR δ 8.05 (d, 2H), 7.60 (t, 1H), 7.46 (t, 2H), 7.30 (d, 1H), 7.24 (s, 1H), 6.79 (d, 1H), 6.67 (d, 2H), 6.65 (dd, 1H), 6.15 (bs, OH), 3.78 (m, 2H), 3.58 (d, 1H), 3.54 (s, 3H), 3.43 (d, 1H), 0.97 (t, 3H). Calculated mass for C25H22ClNO5, 451.12. Observed 474.0 (M+Na).

Example 63

3-((1H-indol-3-yl)methyl)-5-chloro-2-oxo-1-propylindolin-3-yl benzoate

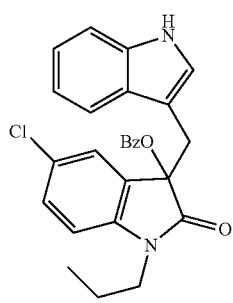

To an oven dried flask cooled under argon equipped with a stir bar was added 5-chloro-2-oxo-1-propylindolin-3-yl benzoate (0.08 grams, 0.24 mmol, 0.2 M in toluene). While stirring at 0° C. KHMDS (0.3 mL, 0.26 mmol, 0.87 M, purchased from Fisher Scientific) was added. After approximately fifteen minutes a solution of (1-benzoyl-1H-indol-3-yl)methyl benzoate (0.02 grams, 0.06 mmol, 0.3 M in anhydrous DMF (purchased from Fisher Scientific)) was added. The reaction continued to stir overnight. The next day the reaction was acidified with 0.1M HCl, diluted with ethyl acetate and the two layers were separated. The aqueous layer was salted out and washed twice more with ethyl acetate. The combined organic solution was dried with sodium sulfate, filtered and concentrated. Purification was done on a Teledyne ISCO with silica gel using a hexanes ethyl acetate gradient. This was followed by a subsequent reverse phase purification using Teledyne ISCO with a C18 column and a water with 0.1% formic acid, acetonitrile gradient. 43% yield. 1H-NMR δ 8.05 (bs, NH), 8.00 (d, 2H), 7.57 (t, 1H), 7.50 (d, 1H), 7.42 (t, 2H), 7.30 (d, 1H), 7.18 (m, 2H), 7.08 (m, 2H), 6.78 (d, 1H), 6.61 (d, 1H), 3.71 (d, 1H), 3.60 (m, 1H), 3.51 (d, 1H), 3.40 (m, 1H), 1.35 (m, 2H), 0.74 (t, 3H). Calculated mass for C27H23ClN2O3, 458.14. Observed 481.1 (M+Na).

Example 64

3-((1-benzoyl-1H-indol-3-yl)methyl)-3-hydroxy-5-methyl-1-propylindolin-2-one

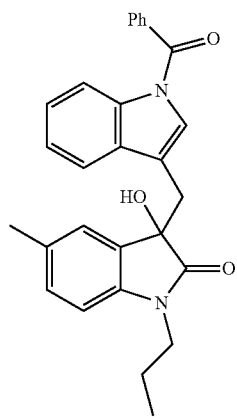 [SMILES: CCCN1C(=O)C(O)(Cc2cn(C(=O)c3ccccc3)c3ccccc23)c2cc(C)ccc21]

This compound was made in a method analogous to 3-((1H-indol-3-yl)methyl)-5-chloro-2-oxo-1-propylindolin-3-yl benzoate using 5-methyl-2-oxo-1-propylindolin-3-yl benzoate and (1-benzoyl-1H-indol-3-yl)methyl benzoate. 1H-NMR δ 8.33 (d, 1H), 7.53 (m, 2H), 7.45-7.39 (m, 4H), 7.31 (dd, 1H), 7.29 (m, 1H), 7.17 (s, 1H), 7.08 (d, 1H), 6.59 (m, 2H), 3.53 (m, 1H), 3.40 (d, 1H), 3.29 (d, 1H), 3.20 (m, 1H), 2.77 (s, OH), 2.30 (s, 3H), 1.15 (m, 2H), 0.56 (t, 3H). Calculated mass for C28H26N2O3, 438.19. Observed 461.2 (M+Na).

Example 65

3-((1H-indol-3-yl)methyl)-1-butyl-2-oxoindolin-3-yl benzoate

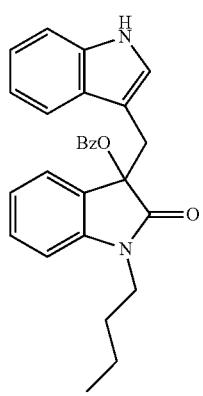

This compound was made in an analogous method as 3-((1H-indol-3-yl)methyl)-5-chloro-2-oxo-1-propylindolin-3-yl benzoate) using 1-butyl-2-oxoindolin-3-yl benzoate and (1-benzoyl-1H-indol-3-yl)methyl benzoate. 1H-NMR δ 8.03 (d, 2H), 7.97 (bs, NH), 7.54 (t, 1H), 7.48 (d, 1H), 7.42 (m, 2H), 7.28 (d, 1H), 7.24 (dd, 1H), 7.15 (m, 2H), 7.05 (dd, 1H), 6.94 (dd, 1H), 6.70 (m, 2H), 3.75 (d, 1H), 3.68 (m, 1H), 3.52 (d, 1H), 3.41 (m, 1H), 1.28-1.09 (m, 4H), 0.81 (t, 3H). Calculated mass for C28H26N2O3, 438.19. Observed 461.2 (M+Na).

Example 66

Biological Assays of Certain Compounds of the Invention

The compounds of the invention were tested in various biological assays. The results of these assays indicated that the compounds of the invention ameliorated dysregulated bioenergetics and are, thus, useful for treatment of degenerative diseases and disorders, such as, for example, retinal damage.

MTT Assay

The compound 3-(4,5-Dimethylthiazol-2-yl)-2,5-diphenyltetrazolium bromide (MTT) is a tetrazolium ion that is reduced to a blue formazan dye via several families of NAD(P)H-dependent oxidoreductases. Formation of the formazan dye from MTT or other related tetrazolium dyes are commonly used as a viability assay even though, in fact, the assay is a metabolic capacity assay. While it is true that dead cells cannot produce NAD(P)H, very sick cells in the throes of death can exhibit extremely high levels of metabolic capacity as they attempt to overcome stress and it is well known that the MTT and related assays report on the ability of cells to produce reducing equivalents, and not live-dead ratios (Sumantran 2011). As shown below, it was found that the MTT assay was a useful metabolic assay when linked to more specific bioenergetic assays.

In this assay, 661W or C6 cells were maintained in DMEM supplemented with 10% FBS. 100 μL of 70,000 cells/mL cells were seeded into each well of 96 well plates using DMEM supplemented with 5% FBS. Cells were then allowed to grow to confluency for 48 hours. The compounds of the invention were added in 2 μL media and calcium-ionophore A23187 was then added in 1 μL for a final concentration of 1 μM and after 24 h, 20 uL of 2 μg/mL MTT were added to each well and the cells were incubated for another 4 h after which 100 μL of 1% SDS in 0.01 M aqueous HCl were added to each well and the plates were incubated overnight. Absorbance was measured at 640 and 570 nM (background correction). The 1 μM ionophore A23187 caused about 50% loss in MTT signal at 24 h. Protection was calculated as the increase in absorbance of treatment groups normalized to the vehicle control. As shown in Table 1, the compounds of the invention gave significant protection at low concentrations:

TABLE 1

| Example No. | MTT, % protection, concentration |
| --- | --- |
| 1 | 12%, 1 μM |
| 2 | 83.2%, 1 nM |
| 3 | 74.5%, 1 nM |
| 4 | 61.5%, 800 pM |
| 5 | 39.2%, 1 nM |
| 6 | 68.8%, 500 pM |
| 7 | 43.8%, 1 μM |
| 8 | 65.9%, 1 nM |
| 9 | 62.5%, 800 pM |
| 10 | 52.7%, 1 nM |
| 11 | 35.7%, 1 μM |
| 12 | 67%, 10 μM |
| 13 | 79.4%, 100 nM |
| 14 | 69.6%, 100 nM |
| 15 | 108.5%, 100 nM |
| 16 | 78.7%, 100 nM |
| 17 | 111%, 100 nM |
| 18 | 68.8%, 100 nM |
| 19 | 81.8%, 100 nM |
| 20 | 59.5%, 100 nM |
| 21 | 82.9%, 100 nM |
| 22 | 71.8%, 10 nM |
| 23 | 73%, 10 nM |
| 24 | 69%, 1 nM |
| 25 | 73.8%, 1 nM |
| 26 | 83.8%, 10 nM |
| 27 | 66%, 1 μM |
| 28 | 65.9%, 1 μM |
| 29 | 98.9%, 100 nM |
| 30 | 69%, 1 nM |
| 31 | 64.2%, 1 nM |
| 32 | 102%, 100 nM |
| 33 | 50%, 100 nM |
| 34 | 82.4%, 1 nM |
| 35 | 113.5%, 800 pM |
| 36 | 86.8%, 100 nM |
| 37 | 68.4%, 800 pM |
| 38 | 84.1%, 1 nM |
| 39 | 83.2%, 1 nM |
| 40 | 81.1%, 1 nM |
| 41 | 66.8%, 1 μM |
| 42 | 69.8%, 1 nM |
| 43 | 64.8%, 1 nM |
| 44 | 72%, 1 nM |
| 45 | 63%, 1 nM |
| 46 | 82%, 1 μM |
| 47 | 21.8%, 1 nM |
| 48 | 91%, 1 nM |
| 49 | 78.3%, 800 pM |
| 50 | 79.2%, 1 nM |
| 51 | 62.2%, 1 nM |
| 52 | 24%, 100 nM |
| 53 | 100%, 1 nM |
| 54 | 85.8%, 800 pM |
| 55 | 67.4%, 1 nM |
| 56 | 85.3%, 1 nM |
| 57 | 71%, 800 pM |
| 58 | 100%, 100 nM |
| 59 | 117.4%, 1 μM |
| 60 | 68.7%, 1 nM |
| 61 | 87.1%, 1 nM |
| 62 | 86.4%, 800 pM |
| 63 | 120%, 1 nM |
| 64 | 51.5%, 100 nM |
| 65 | 135%, 500 pM |

XF FCCP-Uncoupled Oxygen Consumption Rate Assay

The XF FCCP-uncoupled oxygen consumption rate assay assesses mitochondrial capacity by measuring cellular respiration. It was shown that the maximum FCCP-uncoupled oxygen consumption rate (OCR) was a good estimate of maximal mitochondrial capacity (Beeson 2010) and that IBMX treatment of 661W or C6 cells for 24 h caused a loss in maximal uncoupled OCR (Perron 2013). Thus, cells were pretreated with the exemplified compounds for 1 h, added 600 μM IBMX and then measured the uncoupled rate after 24 h. In brief, the OCR measurements were performed using a Seahorse Bioscience XF instrument (Seahorse Bioscience, Billerica, Md.), as previously published (Perron 2013). $O_2$ leakage through the plastic sides and bottom of the plate was accounted for using the AKOS algorithm in the XF software package. Cells were plated on 96- or 24-well custom plates designed for use in the XF and grown to confluency in DMEM+5 FBS (48 h). The medium was then replaced with DMEM+1% FBS for 24 h, along with any treatments. The IBMX treatment alone typically caused about a 50% decrease in the uncoupled rate and protection was calculated as the increase in absorbance of treatment groups normalized to the vehicle control. As shown in Table 2, representative compounds of the invention gave significant protection in this assay:

TABLE 2

| Example | XF FCCP OCR (% Ctrl, Concentration) |
| --- | --- |
| 2 | 79%, 1 nM |
| 3 | 74.5%, 1 nM |
| 4 | 69%, 1 nM |
| 6 | 67%, 800 pM |
| 12 | 73%, 10 uM |
| 22 | 76%, 10 nM |
| 23 | 73%, 10 nM |
| 24 | 59%, 10 nM |
| 25 | 57%, 1 nM |
| 26 | 62%, 1 nM |
| 30 | 59%, 1 nM |
| 31 | 74%, 1 nM |
| 34 | 94%, 1 nM |
| 35 | 55%, 800 pM |
| 37 | 65%, 1 nM |
| 38 | 78%, 1 nM |
| 39 | 66%, 1 nM |
| 40 | 66%, 1 nM |
| 41 | 79%, 1 nM |
| 42 | 71%, 1 nM |
| 43 | 69%, 1 nM |
| 48 | 85%, 1 nM |
| 50 | 65%, 1 nM |
| 51 | 65% 1 nM |
| 53 | 91% 1 nM |
| 56 | 68% 1 nM |
| 58 | 97%, 1 nM |
| 59 | 92%, 1 nM |
| 61 | 67%, 1 nM |
| 62 | 70%, 800 pM |
| 63 | 78%, 1 nM |
| 65 | 61%, 500 pM |

Retinal Degeneration Assay

The in vitro data demonstrated that the compounds of the invention mitigated oxidative- and calcium-induced loss of mitochondrial metabolic capacity. It was reasoned that the compounds' activities would enable them to protect against loss of photoreceptors in retinal degenerative animal models. As a translational bridge between the cell line-based assays and in vivo animal studies, mouse retina organ cultures were utilized. These retinal explants were a powerful ex vivo screening tool, which allowed the testing of photoreceptor cell survival within the retinal network, and the effects of a specific compound were tested like in an in vitro system, without systemic interference. In this assay, the rd1 mouse was utilized. The genotype of the rd1 mouse has a mutation in the β-subunit of the phosphodiesterase gene. This mutation resulted in high levels of cGMP, leaving an increased number of the cGMP-gated channels in the open state, allowing intracellular calcium to rise to toxic levels and rapid rod degeneration. The genetic deficit and the retinal pathology were very similar to that observed in the patients with βPDE-dependent RP. In these mice, rod photoreceptor degeneration started after postnatal day 10 (P10), progressing rapidly, such that at P21, only 1-2 rows of photoreceptor remained, mainly representing cones. Finally, the rd1 mouse retina was amenable to culturing, replicating both retinal development and degeneration, following the same time course as in vivo. The retinal explants were cultured for 11 days ex vivo. Explants were treated with compounds of the invention. Additives were replaced with fresh medium in every alternate day. At the end of the experiments, tissues were fixed, sectioned and stained with 0.1% toluidine and the numbers of rows of photoreceptors remaining in the outer nuclear layer (ONL) were counted. Rd1 explants treated with vehicle only were found to contain 1.2±0.19 cells in the ONL. This was in contrast to cultures treated with representative compounds of the invention that showed significant protection (Table 3 below):

TABLE 3

| Example No. | Rd1 vehicle (# of rows) | rd1 protection (concentration, # of rows) |
| --- | --- | --- |
| 12 | 1.27 | 5 µM, 3.19 |
| 31 | 1.4 | 10 nM, 2.53 |

Light Model Assay

The light model assay is generally accepted as a model of age related macular degeneration (AMD). Light as an environmental factor has been shown to be toxic to rod photoreceptors if the retina was exposed to high light levels over a long period of time; and oxidative stress has been implicated as the main trigger for cell death. In particular, oxidative damage has been detected by immunohistochemistry, detecting the presence of oxidized and tyrosine-phosphorylated proteins as well as the upregulation of endogenous antioxidants such as thioredoxin and glutathione peroxidase. Likewise, exogenous antioxidants have been found to protect the rodent retina from light damage. Additional indirect evidence for the involvement of oxidative stress in photoreceptor degeneration has been provided by treatment of photodamaged retinas with antioxidants such as dimethylthiourea, or the treatment of N-methyl-N-nitrosourea (MNU)-challenged rats with the antioxidant DHA.

The light model assay was used to further test the therapeutic potential of the compounds of the invention. Photoreceptors from albino animals are very sensitive to constant light, lacking the RPE pigment to protect them. Thus, Balb/c mice were exposed to continuous light for 7 days, which caused loss of about 50% of the photoreceptor cells as measured via histology. To test the potential therapeutic efficacy, eyedrops were formulated in 0.1% Bij 35 in 9% saline, applied once or twice daily throughout the period of light exposure, and their effect assessed on the light-induced degeneration of photoreceptor cells morphologically and electrophysiologically, 10 days after the onset of the CL exposure. In control BALB/c mice, constant light resulted in the elimination of ~50% of the photoreceptors (average retina score: 4.3±0.25 rows of photoreceptors), whereas the mice treated with representative compounds of the invention (eyedrops once per day) retained significantly more photoreceptors cells (Table 4).

TABLE 4

| Example No. | LD Vehicle (# of rows) | LD Protection (concentration, # of rows) |
| --- | --- | --- |
| 12 | 4.25 | 1 mM, 5.33 |
| 31 | 5.1 | 1 mM, 5.94 |
| 13 | 4.92 | 1 mM, 5.44 |

TABLE 4-continued

| Example No. | LD Vehicle (# of rows) | LD Protection (concentration, # of rows) |
| --- | --- | --- |
| 28 | 4.35 | 1 mM, 5.55 |
| 59 | 5.15 | 100 µM, 5.98 |
| 58 | 4.97 | 100 µM, 6.06 |
| 34 | 5.0 | 10 µM, 5.47 |

S334ter Assay

To further evaluate neuroprotection, certain compounds of the invention were evaluated with the Ser344ter-3 rats in which a truncation in the rhodopsin N-terminus eliminated a phosphorylation site. It has been shown that the Ser344ter-3 rhodopsin was extensively misfolded causing induction of ER stress genes BiP and CHOP (Kroeger 2012). P12-P17 retinal explants from Ser344ter-3 rats were treated with 5 µM of certain compounds of the invention. Statistically significant protection against loss of photoreceptor cell nuclei was observed (Table 5 below). These results demonstrated that metabolic load from various stressors was a general underlying mechanism for damage in retinal degenerative pathologies.

TABLE 5

| Example No. | S334ter vehicle (# of rows) | s334ter protection (concentration, # of rows) |
| --- | --- | --- |
| 12 | 2.46 | 1 µM 3.86 |
| 58 | 1.36 | 50 nM, 2.73 |

As seen above, the compounds of the invention mitigate oxidative- and calcium-mediated loss of mitochondrial capacity in cell lines and protect photoreceptors from cell death in several models of retinal degeneration.

REFERENCES

Acosta M L, Fletcher E L, Azizoglu S, Foster L E, Farber D B, Kalloniatis M: Early markers of retinal degeneration in rd/rd mice. Mol Vis 2005, 11:717-728.

Acosta M L, Shin Y S, Ready S, Fletcher E L, Christie D L, Kalloniatis M. Retinal metabolic state of the proline-23-histidine rat model of retinitis pigmentosa. Am J Physiol Cell Physiol. 2010 March; 298(3):C764-74. doi: 10.1152/ajpcell.00253.2009. Epub 2009 Dec. 23. PubMed PMID: 20032515.

Bandyopadhyay M, Rohrer B. Photoreceptor structure and function is maintained in organotypic cultures of mouse retinas. Mol Vis. 2010 Jun. 26; 16:1178-85. PubMed PMID: 20664685; PubMed Central PMCID: PMC2901185.

Barot M, Gokulgandhi M R, Mitra A K. Mitochondrial dysfunction in retinal diseases. Curr Eye Res. 2011 December; 36(12):1069-77. doi: 10.3109/02713683.2011.607536. Epub 2011 Oct. 6. Review. PubMed PMID: 21978133.

Beal D M, Jones L H. Molecular scaffolds using multiple orthogonal conjugations: applications in chemical biology and drug discovery. Angew Chem Int Ed Engl. 2012 Jun. 25; 51(26):6320-6. doi: 10.1002/anie.201200002. Epub 2012 Apr. 19. Review. PubMed PMID: 22517597.

Beeson C C, Beeson G C, Schnellmann R G. A high-throughput respirometric assay for mitochondrial biogenesis and toxicity. Anal Biochem. 2010 Sep. 1; 404(1):75-81. doi: 10.1016/j.ab.2010.04.040. Epub 2010 May 11. PubMed PMID: 20465991; PubMed Central PMCID: PMC2900494.

Booij J C, van Soest S, Swagemakers S M, Essing A H, Verkerk A J, van der Spek P J, Gorgels T G, Bergen A A. Functional annotation of the human retinal pigment epithelium transcriptome. BMC Genomics. 2009 Apr. 20; 10:164. doi: 10.1186/1471-2164-10-164. PubMed PMID: 19379482; PubMed Central PMCID: PMC2679759.

Bruce J E. In vivo protein complex topologies: sights through a cross-linking lens. Proteomics. 2012 May; 12(10):1565-75. doi: 10.1002/pmic.201100516. Review. PubMed PMID: 22610688.

Catoire M, Mensink M, Boekschoten M V, Hangelbroek R, Müller M, Schrauwen P, Kersten S. Pronounced effects of acute endurance exercise on gene expression in resting and exercising human skeletal muscle. PLoS One. 2012; 7(11):e51066. doi: 10.1371/journal.pone.0051066. Epub 2012 Nov. 30. PubMed PMID: 23226462; PubMed Central PMCID: PMC3511348.

Cavalier-Smith T, Chao E E. Phylogeny of choanozoa, apusozoa, and other protozoa and early eukaryote megaevolution. J Mol Evol. 2003 May; 56(5):540-63. PubMed PMID: 12698292.

Cazares L H, Troyer D A, Wang B, Drake R R, Semmes O J. MALDI tissue imaging: from biomarker discovery to clinical applications. Anal Bioanal Chem. 2011 July; 401(1):17-27. doi: 10.1007/s00216-011-5003-6. Epub 2011 May 4. Review. PubMed PMID: 21541816.

Chaurand P, Cornett D S, Caprioli R M. Molecular imaging of thin mammalian tissue sections by mass spectrometry. Curr Opin Biotechnol. 2006 August; 17(4):431-6. Epub 2006 Jun. 16. Review. PubMed PMID: 16781865.

Chen Y A, Almeida J S, Richards A J, Müller P, Carroll R J, Rohrer B. A nonparametric approach to detect nonlinear correlation in gene expression. J Comput Graph Stat. 2010 Sep. 1; 19(3):552-568. PubMed PMID: 20877445; PubMed Central PMCID: PMC2945392.

Copple I M. The Keap1-Nrf2 cell defense pathway—a promising therapeutic target Adv Pharmacol. 2012; 63:43-79. doi: 10.1016/B978-0-12-398339-8.00002-1. Review. PubMed PMID: 22776639.

Court F A, Coleman M P. Mitochondria as a central sensor for axonal degenerative stimuli. Trends Neurosci. 2012 June; 35(6):364-72. doi: 10.1016/j.tins.2012.04.001. Epub 2012 May 11. Review. PubMed PMID: 22578891.

Dai C, Cazares L H, Wang L, Chu Y, Wang S L, Troyer D A, Semmes O J, Drake R R, Wang B. Using boronolectin in MALDI-M S imaging for the histological analysis of cancer tissue expressing the sialyl Lewis X antigen. Chem Commun (Camb). 2011 Oct. 7; 47(37):10338-40. doi: 10.1039/c1cc11814e. Epub 2011 Aug. 19. PubMed PMID: 21853197.

Daiger S P, Sullivan L S, Bowne S J, Birch D G, Heckenlively J R, Pierce E A, Weinstock G M. Targeted high-throughput DNA sequencing for gene discovery in retinitis pigmentosa. Adv Exp Med Biol. 2010; 664:325-31. doi: 10.1007/978-1-4419-1399-9_37. PubMed PMID: 20238032; PubMed Central PMCID: PMC2909649.

De Jesús-Cortés H, Xu P, Drawbridge J, Estill S J, Huntington P, Tran S, Britt J, Tesla R, Morlock L, Naidoo J, Melito L M, Wang G, Williams N S, Ready J M, McKnight S L, Pieper A A. Neuroprotective efficacy of aminopropyl carbazoles in a mouse model of Parkinson disease.

Proc Natl Acad Sci USA. 2012 Oct. 16; 109(42):17010-5. doi: 10.1073/pnas.1213956109. Epub 2012 Oct. 1. PubMed PMID: 23027934; PubMed Central PMCID: PMC3479520.

Demos C, Bandyopadhyay M, Rohrer B. Identification of candidate genes for human retinal degeneration loci using differentially expressed genes from mouse photoreceptor dystrophy models. Mol Vis. 2008 Sep. 5; 14:1639-49. PubMed PMID: 18776951; PubMed Central PMCID: PMC2529471.

Dong S Q, Xu H Z, Xia X B, Wang S, Zhang L X, Liu S Z. Activation of the ERK 1/2 and STAT3 signaling pathways is required for 661W cell survival following oxidant injury. Int J Ophthalmol. 2012; 5(2):138-42. doi: 10.3980/j.issn.2222-3959.2012.02.04. Epub 2012 Apr. 18. PubMed PMID: 22762037; PubMed Central PMCID: PMC3359025.

Egger A, Samardzija M, Sothilingam V, Tanimoto N, Lange C, Salatino S, Fang L, Garcia-Garrido M, Beck S, Okoniewski M J, Neutzner A, Seeliger M W, Grimm C, Handschin C. PGC-1α determines light damage susceptibility of the murine retina. PLoS One. 2012; 7(2): e31272. doi: 10.1371/journal.pone.0031272. Epub 2012 February 13. PubMed PMID: 22348062; PubMed Central PMCID: PMC3278422.

Estrada-Cuzcano A, Roepman R, Cremers F P, den Hollander A I, Mans D A. Non-syndromic retinal ciliopathies: translating gene discovery into therapy. Hum Mol Genet. 2012 Oct. 15; 21(R1):R111-24. Epub 2012 Jul. 26. PubMed PMID: 22843501.

Falk M J, Zhang Q, Nakamaru-Ogiso E, Kannabiran C, Fonseca-Kelly Z, Chakarova C, Audo I, Mackay D S, Zeitz C, Borman A D, Staniszewska M, Shukla R, Palavalli L, Mohand-Said S, Waseem N H, Jalali S, Perin J C, Place E, Ostrovsky J, Xiao R, Bhattacharya S S, Consugar M, Webster A R, Sahel J A, Moore A T, Berson E L, Liu Q, Gai X, Pierce E A. NMNAT1 mutations cause Leber congenital amaurosis. Nat Genet. 2012 September; 44(9): 1040-5. doi: 10.1038/ng.2361. Epub 2012 Jul. 29. PubMed PMID: 22842227; PubMed Central PMCID: PMC3454532.

Farber D B, Lolley R N: Cyclic guanosine monophosphate: elevation in degenerating photoreceptor cells of the C3H mouse retina. Science 1974, 186:449-451.

Farber D B: From mice to men: the cyclic GMP phosphodiesterase gene in vision and disease. The Proctor Lecture. Invest Ophthalmol Vis Sci 1995, 36(2):263-275.

Ferrick D A, Neilson A, Beeson C. Advances in measuring cellular bioenergetics using extracellular flux. Drug Discov Today. 2008 March; 13(5-6):268-74. doi: 10.1016/j.drudis.2007.12.008. Epub 2008 February 13. Review. PubMed PMID: 18342804.

Fox D A, Poblenz A T, He L: Calcium overload triggers rod photoreceptor apoptotic cell death in chemical-induced and inherited retinal degenerations. Ann NY Acad Sci 1999, 893:282-285.

Gilliam J C, Chang J T, Sandoval I M, Zhang Y, Li T, Pittler S J, Chiu W, Wensel T G. Three-dimensional architecture of the rod sensory cilium and its disruption in retinal neurodegeneration. Cell. 2012 Nov. 21; 151(5):1029-41. doi: 10.1016/j.cell.2012.10.038. PubMed PMID: 23178122.

Graymore C: Metabolism of the Developing Retina. 7. Lactic Dehydrogenase Isoenzyme in the Normal and Degenerating Retina. a Preliminary Communication. Exp Eye Res 1964, 89:5-8.

Hartong D T, Dange M, McGee T L, Berson E L, Dryja T P, Colman R F. Insights from retinitis pigmentosa into the roles of isocitrate dehydrogenases in the Krebs cycle. Nat Genet. 2008 October; 40(10):1230-4. doi: 10.1038/ng.223. Epub 2008 Sep. 21. PubMed PMID: 18806796; PubMed Central PMCID: PMC2596605.

Ho C H, Piotrowski J, Dixon S J, Baryshnikova A, Costanzo M, Boone C. Combining functional genomics and chemical biology to identify targets of bioactive compounds. Curr Opin Chem Biol. 2011 February; 15(1):66-78. doi: 10.1016/j.cbpa.2010.10.023. Epub 2010 Nov. 17. Review. PubMed PMID: 21093351.

Ibebunjo C, Chick J M, Kendall T, Eash J K, Li C, Zhang Y, Vickers C, Wu Z, Clarke B A, Shi J, Cruz J, Fournier B, Brachat S, Gutzwiller S, Ma Q, Markovits J, Broome M, Steinkrauss M, Skuba E, Galarneau J R, Gygi S P, Glass D J. Genomic and proteomic profiling reveals reduced mitochondrial function and disruption of the neuromuscular junction driving rat sarcopenia. Mol Cell Biol. 2013 January; 33(2):194-212. doi: 10.1128/MCB.01036-12. Epub 2012 Oct. 29. PubMed PMID: 23109432.

Jaliffa C, Ameqrane I, Dansault A, Leemput J, Vieira V, Lacassagne E, Provost A, Bigot K, Masson C, Menasche M, Abitbol M. Sirt1 involvement in rd10 mouse retinal degeneration. Invest Ophthalmol Vis Sci. 2009 August; 50(8):3562-72. doi: 10.1167/iovs.08-2817. Epub 2009 Apr. 30. PubMed PMID: 19407027.

Jarrett S G, Rohrer B, Perron N R, Beeson C, Boulton M E. Assessment of mitochondrial damage in retinal cells and tissues using quantitative polymerase chain reaction for mitochondrial DNA damage and extracellular flux assay for mitochondrial respiration activity. Methods Mol Biol. 2013; 935:227-43. doi: 10.1007/978-1-62703-080-9_16. PubMed PMID: 23150372.

Jewett J C, Bertozzi C R. Cu-free click cycloaddition reactions in chemical biology. Chem Soc Rev. 2010 April; 39(4):1272-9. Review. PubMed PMID: 20349533; PubMed Central PMCID: PMC2865253.

Kanan Y, Moiseyev G, Agarwal N, Ma J X, Al-Ubaidi M R. Light induces programmed cell death by activating multiple independent proteases in a cone photoreceptor cell line. Invest Ophthalmol Vis Sci. 2007 January; 48(1):40-51. PubMed PMID: 17197514.

Kandpal R P, Rajasimha H K, Brooks M J, Nellissery J, Wan J, Qian J, Kern T S, Swaroop A. Transcriptome analysis using next generation sequencing reveals molecular signatures of diabetic retinopathy and efficacy of candidate drugs. Mol Vis. 2012; 18:1123-46. Epub 2012 May 2. PubMed PMID: 22605924; PubMed Central PMCID: PMC3351417.

Karbowski M, Neutzner A. Neurodegeneration as a consequence of failed mitochondrial maintenance. Acta Neuropathol. 2012 Feb.; 123(2): 157-71. doi: 10.1007/s00401-011-0921-0. Epub 2011 Dec. 7. Review. PubMed PMID: 22143516.

Kroeger H, Messah C, Ahern K, Gee J, Joseph V, Matthes M T, Yasumura D, Gorbatyuk M S, Chiang W C, Lavail M M, Lin J H. Induction of Endoplasmic Reticulum Stress Genes, BiP and Chop, in Genetic and Environmental Models of Retinal Degeneration. Invest Ophthalmol Vis Sci. 2012 Nov. 9; 53(12):7590-9. doi: 10.1167/iovs.12-10221. PubMed PMID: 23074209; PubMed Central PMCID: PMC3495601.

Krysko D V, Agostinis P, Krysko O, Garg A D, Bachert C, Lambrecht B N, Vandenabeele P. Emerging role of damage-associated molecular patterns derived from mitochondria in inflammation. Trends Immunol. 2011 April;

32(4):157-64. doi: 10.1016/j.it.2011.01.005. Epub 2011 February 19. Review. PubMed PMID: 21334975.

Kunchithapautham K, Rohrer B: Apoptosis and Autophagy in Photoreceptors Exposed to Oxidative Stress. Autophagy 2007, 3(5).

Lenz E M, Wilson I D: Analytical strategies in metabonomics. *J Proteome Res* 2007, 6(2):443-458.

Lin J H, Lavail M M. Misfolded proteins and retinal dystrophies. Adv Exp Med Biol. 2010; 664:115-21. doi: 10.1007/978-1-4419-1399-9_14. Review. PubMed PMID: 20238009; PubMed Central PMCID: PMC2955894.

Liu Q, Tan G, Levenkova N, Li T, Pugh E N Jr, Rux J J, Speicher D W, Pierce E A. The proteome of the mouse photoreceptor sensory cilium complex. Mol Cell Proteomics. 2007 August; 6(8):1299-317. Epub 2007 May 9. PubMed PMID: 17494944; PubMed Central PMCID: PMC2128741.

Liu Q, Zhang Q, Pierce E A. Photoreceptor sensory cilia and inherited retinal degeneration. Adv Exp Med Biol. 2010; 664:223-32. doi: 10.1007/978-1-4419-1399-9_26. Review. PubMed PMID: 20238021; PubMed Central PMCID: PMC2888132.

Lohr H R, Kuntchithapautham K, Sharma A K, Rohrer B: Multiple, parallel cellular suicide mechanisms participate in photoreceptor cell death. Exp Eye Res 2006, 83(2): 380-389.

Lohr H R, Kuntchithapautham K, Sharma A K, Rohrer B. Multiple, parallel cellular suicide mechanisms participate in photoreceptor cell death. Exp Eye Res. 2006 August; 83(2):380-9. Epub 2006 Apr. 19. Erratum in: Exp Eye Res. 2006 December; 83(6):1522. PubMed PMID: 16626700.

MacMillan K S, Naidoo J, Liang J, Melito L, Williams N S, Morlock L, Huntington P J, Estill S J, Longgood J, Becker G L, McKnight S L, Pieper A A, De Brabander J K, Ready J M. Development of proneurogenic, neuroprotective small molecules. J Am Chem Soc. 2011 February 9; 133(5):1428-37. doi: 10.1021/ja108211m. Epub 2011 January 6. PubMed PMID: 21210688; PubMed Central PMCID: PMC3033481.

Mamidyala S K, Finn M G. In situ click chemistry: probing the binding landscapes of biological molecules. Chem Soc Rev. 2010 April; 39(4):1252-61. doi: 10.1039/b901969n. Epub 2010 Mar. 1. Review. PubMed PMID: 20309485.

Mandal M N, Patlolla J M, Zheng L, Agbaga M P, Tran J T, Wicker L, Kasus-Jacobi A, Elliott M H, Rao C V, Anderson R E. Curcumin protects retinal cells from light- and oxidant stress-induced cell death. Free Radic Biol Med. 2009 Mar. 1; 46(5):672-9. doi: 10.1016/j.freeradbiomed.2008.12.006. Epub 2008 Dec. 24. PubMed PMID: 19121385; PubMed Central PMCID: PMC2810836.

Marina N, Sajic M, Bull N D, Hyatt A J, Berry D, Smith K J, Martin K R. Lamotrigine monotherapy does not provide protection against the loss of optic nerve axons in a rat model of ocular hypertension. Exp Eye Res. 2012 November; 104:1-6. doi: 10.1016/j.exer.2012.09.002. Epub 2012 Sep. 13. PubMed PMID: 22982756.

Mattson M P, Kroemer G: Mitochondria in cell death: novel targets for neuroprotection and cardioprotection. Trends Mol Med 2003, 9(5):196-205.

McKnight S L. Back to the future: molecular biology meets metabolism. Cold Spring Harb Symp Quant Biol. 2011; 76:403-11. doi: 10.1101/sqb.2012.76.013722. Epub 2012 Apr. 17. Review. PubMed PMID: 22510749.

Mueller E E, Schaier E, Brunner S M, Eder W, Mayr J A, Egger S F, Nischler C, Oberkofler H, Reitsamer H A, Patsch W, Sperl W, Kofler B. Mitochondrial haplogroups and control region polymorphisms in age-related macular degeneration: a case-control study. PLoS One. 2012; 7(2):e30874. doi: 10.1371/journal.pone.0030874. Epub 2012 February 13. PubMed PMID: 22348027; PubMed Central PMCID: PMC3278404.

Mulkidjanian A Y, Galperin M Y, Makarova K S, Wolf Y I, Koonin E V. Evolutionary primacy of sodium bioenergetics. Biol Direct. 2008 Apr. 1; 3:13. doi: 10.1186/1745-6150-3-13. PubMed PMID: 18380897; PubMed Central PMCID: PMC2359735.

Nicholas P C, Kim D, Crews F T, Macdonald J M: (1)H NMR-Based Metabolomic Analysis of Liver, Serum, and Brain Following Ethanol Administration in Rats. *Chem Res Toxicol* 2007.

Nixon E, Simpkins J W. Neuroprotective effects of nonfeminizing estrogens in retinal photoreceptor neurons. Invest Ophthalmol Vis Sci. 2012 Jul. 12; 53(8):4739-47. doi: 10.1167/iovs.12-9517. Print 2012 July PubMed PMID: 22700711.

O'Toole J F, Liu Y, Davis E E, Westlake C J, Attanasio M, Otto E A, Seelow D, Nurnberg G, Becker C, Nuutinen M, Kärppä M, Ignatius J, Uusimaa J, Pakanen S, Jaakkola E, van den Heuvel L P, Fehrenbach H, Wiggins R, Goyal M, Zhou W, Wolf M T, Wise E, Helou J, Allen S J, Murga-Zamalloa C A, Ashraf S, Chaki M, Heeringa S, Chernin G, Hoskins B E, Chaib H, Gleeson J, Kusakabe T, Suzuki T, Isaac R E, Quarmby L M, Tennant B, Fujioka H, Tuominen H, Hassinen I, Lohi H, van Houten J L, Rotig A, Sayer J A, Rolinski B, Freisinger P, Madhavan S M, Herzer M, Madignier F, Prokisch H, Nurnberg P, Jackson P K, Khanna H, Katsanis N, Hildebrandt F. Individuals with mutations in XPNPEP3, which encodes a mitochondrial protein, develop a nephronophthisis-like nephropathy. J Clin Invest. 2010 March; 120(3):791-802. doi: 10.1172/JCI40076. Epub 2010 February 22. Erratum in: J Clin Invest. 2010 April; 120(4):1362. Jackson, Peter [corrected to Jackson, Peter K]. PubMed PMID: 20179356; PubMed Central PMCID: PMC2827951.

Osborne N N, Del Olmo-Aguado S. Maintenance of retinal ganglion cell mitochondrial functions as a neuroprotective strategy in glaucoma. Curr Opin Pharmacol. 2012 Sep. 19. doi:pii: 51471-4892(12)00159-2. 10.1016/j.coph.2012.09.002. [Epub ahead of print] PubMed PMID: 22999653.

Pappas D J, Gabatto P A, Oksenberg D, Khankhanian P, Baranzini S E, Gan L, Oksenberg J R. Transcriptional expression patterns triggered by chemically distinct neuroprotective molecules. Neuroscience. 2012 Dec. 13; 226: 10-20. doi: 10.1016/j.neuroscience.2012.09.007. Epub 2012 Sep. 15. PubMed PMID: 22986168; PubMed Central PMCID: PMC3489981.

Pereira D A, Williams J A. Origin and evolution of high throughput screening. Br J Pharmacol. 2007 September; 152(1):53-61. Epub 2007 Jul. 2. Review. PubMed PMID: 17603542; PubMed Central PMCID: PMC1978279.

Perron N R, Beeson C, Rohrer B. Early alterations in mitochondrial reserve capacity; a means to predict subsequent photoreceptor cell death. J Bioenerg Biomembr. 2012 Oct. 23. [Epub ahead of print] PubMed PMID: 23090843.

Pieper A A, Xie S, Capota E, Estill S J, Zhong J, Long J M, Becker G L, Huntington P, Goldman S E, Shen C H, Capota M, Britt J K, Kotti T, Ure K, Brat D J, Williams N S, MacMillan K S, Naidoo J, Melito L, Hsieh J, De Brabander J, Ready J M, McKnight S L. Discovery of a proneurogenic, neuroprotective chemical. Cell. 2010 Jul. 9; 142(1):39-51. doi: 10.1016/j.cell.2010.06.018. PubMed PMID: 20603013; PubMed Central PMCID: PMC2930815.

Pierce E A, Quinn T, Meehan T, McGee T L, Berson E L, Dryja T P: Mutations in a gene encoding a new oxygen-regulated photoreceptor protein cause dominant retinitis pigmentosa. Nat Genet 1999, 22(3):248-254.

Pierce E A: Pathways to photoreceptor cell death in inherited retinal degenerations. Bioessays 2001, 23(7):605-618.

Qin L X, Beyer R P, Hudson F N, Linford N J, Morris D E, Kerr K F. Evaluation of methods for oligonucleotide array data via quantitative real-time PCR. BMC Bioinformatics. 2006 January 17; 7:23. PubMed PMID: 16417622; PubMed Central PMCID: PMC1360686.

Rezaie T, McKercher S R, Kosaka K, Seki M, Wheeler L, Viswanath V, Chun T, Joshi R, Valencia M, Sasaki S, Tozawa T, Satoh T, Lipton S A. Protective effect of carnosic Acid, a pro-electrophilic compound, in models of oxidative stress and light-induced retinal degeneration. Invest Ophthalmol Vis Sci. 2012 Nov. 27; 53(12):7847-54. doi: 10.1167/iovs.12-10793. PubMed PMID: 23081978; PubMed Central PMCID: PMC3508754.

Richards A J, Muller B, Shotwell M, Cowart L A, Rohrer B, Lu X. Assessing the functional coherence of gene sets with metrics based on the Gene Ontology graph. Bioinformatics. 2010 Jun. 15; 26(12):i79-87. doi: 10.1093/bioinformatics/btq203. PubMed PMID: 20529941; PubMed Central PMCID: PMC2881388.

Richards T A, Cavalier-Smith T. Myosin domain evolution and the primary divergence of eukaryotes. Nature. 2005 Aug. 25; 436(7054):1113-8. PubMed PMID: 16121172.

Rohrer B, Matthes M T, LaVail M M, Reichardt L F: Lack of p75 receptor does not protect photoreceptors from light-induced cell death. *Exp Eye Res* 2003, 76(1):125-129

Rohrer B, Pinto F R, Hulse K E, Lohr H R, Zhang L, Almeida J S. Multidestructive pathways triggered in photoreceptor cell death of the rd mouse as determined through gene expression profiling. J Biol Chem. 2004 Oct. 1; 279(40):41903-10. Epub 2004 Jun. 24. PubMed PMID: 15218024.

Ronquillo C C, Bernstein P S, Baehr W. Senior-Løken syndrome: A syndromic form of retinal dystrophy associated with nephronophthisis. Vision Res. 2012 Dec. 15; 75:88-97. doi: 10.1016/j.visres.2012.07.003. Epub 2012 Jul. 20. PubMed PMID: 22819833; PubMed Central PMCID: PMC3504181.

Sancho-Pelluz J, Alavi M V, Sahaboglu A, Kustermann S, Farinelli P, Azadi S, van Veen T, Romero F J, Paquet-Durand F, Ekstrom P. Excessive HDAC activation is critical for neurodegeneration in the rd1 mouse. Cell Death Dis. 2010; 1:e24. doi: 10.1038/cddis.2010.4. PubMed PMID: 21364632; PubMed Central PMCID: PMC3032332.

Sancho-Pelluz J, Arango-Gonzalez B, Kustermann S, Romero F J, van Veen T, Zrenner E, Ekstrom P, Paquet-Durand F. Photoreceptor cell death mechanisms in inherited retinal degeneration. Mol Neurobiol. 2008 December; 38(3):253-69. doi: 10.1007/s12035-008-8045-9. Epub 2008 Nov. 4. Review. PubMed PMID: 18982459.

SanGiovanni J P, Arking D E, Iyengar S K, Elashoff M, Clemons T E, Reed G F, Henning A K, Sivakumaran T A, Xu X, DeWan A, Agrón E, Rochtchina E, Sue C M, Wang J J, Mitchell P, Hoh J, Francis P J, Klein M L, Chew E Y, Chakravarti A. Mitochondrial DNA variants of respiratory complex I that uniquely characterize haplogroup T2 are associated with increased risk of age-related macular degeneration. PLoS One. 2009; 4(5):e5508. doi: 10.1371/journal.pone.0005508. Epub 2009 May 12. PubMed PMID: 19434233; PubMed Central PMCID: PMC2677106.

Schrier S A, Falk M J. Mitochondrial disorders and the eye. Curr Opin Ophthalmol. 2011 September; 22(5):325-31. doi: 10.1097/ICU.0b013e328349419d. Review. PubMed PMID: 21730846.

Sharma A K, Rohrer B: Calcium-induced calpain mediates apoptosis via caspase-3 in a mouse photoreceptor cell line. J Biol Chem 2004, 279(34):35564-35572.

Sharma A K, Rohrer B. Calcium-induced calpain mediates apoptosis via caspase-3 in a mouse photoreceptor cell line. J Biol Chem. 2004 Aug. 20; 279(34):35564-72. Epub 2004 Jun. 18. PubMed PMID: 15208318.

Sharma A K, Rohrer B. Sustained elevation of intracellular cGMP causes oxidative stress triggering calpain-mediated apoptosis in photoreceptor degeneration. Curr Eye Res. 2007 March; 32(3):259-69. PubMed PMID: 17453946.

Shimazaki H, Hironaka K, Fujisawa T, Tsuruma K, Tozuka Y, Shimazawa M, Takeuchi H, Hara H. Edaravone-loaded liposome eyedrops protect against light-induced retinal damage in mice. Invest Ophthalmol Vis Sci. 2011 Sep. 21; 52(10):7289-97. doi: 10.1167/iovs.11-7983. Print 2011 September PubMed PMID: 21849425.

Smith J J, Kenney R D, Gagne D J, Frushour B P, Ladd W, Galonek H L, Israelian K, Song J, Razvadauskaite G, Lynch A V, Carney D P, Johnson R J, Lavu S, Iffland A, Elliott P J, Lambert P D, Elliston K O, Jirousek M R, Milne J C, Boss O. Small molecule activators of SIRT1 replicate signaling pathways triggered by calorie restriction in vivo. BMC Syst Biol. 2009 Mar. 10; 3:31. doi: 10.1186/1752-0509-3-31. PubMed PMID: 19284563; PubMed Central PMCID: PMC2660283.

Spinazzi M, Cazzola S, Bortolozzi M, Baracca A, Loro E, Casarin A, Solaini G, Sgarbi G, Casalena G, Cenacchi G, Malena A, Frezza C, Carrara F, Angelini C, Scorrano L, Salviati L, Vergani L. A novel deletion in the GTPase domain of OPA1 causes defects in mitochondrial morphology and distribution, but not in function. Hum Mol Genet. 2008 Nov. 1; 17(21):3291-302. doi: 10.1093/hmg/ddn225. Epub 2008 Aug. 4. PubMed PMID: 18678599.

Stone J, Maslim J, Valter-Kocsi K, Mervin K, Bowers F, Chu Y, Barnett N, Provis J, Lewis G, Fisher S K et al: Mechanisms of photoreceptor death and survival in mammalian retina. *Prog Retin Eye Res* 1999, 18(6):689-735.

Sumantran V N. Cellular chemosensitivity assays: an overview. Methods Mol Biol. 2011; 731:219-36. doi: 10.1007/978-1-61779-080-5_19. Review. PubMed PMID: 21516411.

Tan E, Ding XQ, Saadi A, Agarwal N, Naash M I, Al-Ubaidi M R: Expression of cone-photoreceptor-specific antigens in a cell line derived from retinal tumors in transgenic mice. Invest Ophthalmol Vis Sci 2004, 45(3):764-768.

Tan E, Ding XQ, Saadi A, Agarwal N, Naash M I, Al-Ubaidi M R. Expression of cone-photoreceptor-specific antigens in a cell line derived from retinal tumors in transgenic mice. Invest Ophthalmol Vis Sci. 2004 March; 45(3):764-8. PubMed PMID: 14985288; PubMed Central PMCID: PMC2937568.

Tesla R, Wolf H P, Xu P, Drawbridge J, Estill S J, Huntington P, McDaniel L, Knobbe W, Burket A, Tran S, Starwalt R, Morlock L, Naidoo J, Williams N S, Ready J M, McKnight S L, Pieper A A. Neuroprotective efficacy of aminopropyl carbazoles in a mouse model of amyotrophic lateral sclerosis. Proc Natl Acad Sci USA. 2012 Oct. 16; 109(42):17016-21. doi: 10.1073/pnas.1213960109. Epub 2012 Oct. 1. PubMed PMID: 23027932; PubMed Central PMCID: PMC3479516.

Travis G H: Mechanisms of cell death in the inherited retinal degenerations. Am J Hum Genet 1998, 62(3):503-508.

Trifunović D, Sahaboglu A, Kaur J, Mend S, Zrenner E, Ueffing M, Arango-Gonzalez B, Paquet-Durand F. Neuroprotective strategies for the treatment of inherited photoreceptor degeneration. Curr Mol Med. 2012 June; 12(5): 598-612. Review. PubMed PMID: 22515977.

Tu B P, Mohler R E, Liu J C, Dombek K M, Young E T, Synovec R E, McKnight S L. Cyclic changes in metabolic state during the life of a yeast cell. Proc Natl Acad Sci USA. 2007 Oct. 23; 104(43):16886-91. Epub 2007 Oct. 16. PubMed PMID: 17940006; PubMed Central PMCID: PMC2040445.

Van Bergen N J, Crowston J G, Kearns L S, Staffieri S E, Hewitt A W, Cohn A C, Mackey D A, Trounce I A. Mitochondrial oxidative phosphorylation compensation may preserve vision in patients with OPA1-linked autosomal dominant optic atrophy. PLoS One. 2011; 6(6): e21347. doi: 10.1371/journal.pone.0021347. Epub 2011 Jun. 22. PubMed PMID: 21731710; PubMed Central PMCID: PMC3120866.

Vingolo E M, De Mattia G, Giusti C, Forte R, Laurenti O, Pannarale M R: Treatment of nonproliferative diabetic retinopathy with Defibrotide in noninsulin-dependent diabetes mellitus: a pilot study. Acta Ophthalmol Scand 1999, 77(3):315-320.

Wenzel A, Grimm C, Samardzija M, Reme C E: Molecular mechanisms of light-induced photoreceptor apoptosis and neuroprotection for retinal degeneration. Prog Retin Eye Res 2005, 24(2):275-306.

Whitfield J F, Chakravarthy B R. The neuronal primary cilium: driver of neurogenesis and memory formation in the hippocampal dentate gyrus Cell Signal. 2009 September; 21(9):1351-5. doi: 10.1016/j.cellsig.2009.02.013. Epub 2009 February 26. Review. PubMed PMID: 19249355.

Winkler B S, Pourcho R G, Starnes C, Slocum J, Slocum N. Metabolic mapping in mammalian retina: a biochemical and 3H-2-deoxyglucose autoradiographic study. Exp Eye Res. 2003 September; 77(3):327-37. PubMed PMID: 12907165.

Winkler B S. Letter to the editor: Comments on retinal metabolic state in P23H and normal retinas. Am J Physiol Cell Physiol. 2010 July; 299(1):C185; author reply C186-7. doi: 10.1152/ajpcell.00109.2010. PubMed PMID: 20554913.

Yamada Y, Hidefumi K, Shion H, Oshikata M, Haramaki Y. Distribution of chloroquine in ocular tissue of pigmented rat using matrix-assisted laser desorption/ionization imaging quadrupole time-of-flight tandem mass spectrometry. Rapid Commun Mass Spectrom. 2011 Jun. 15; 25(11): 1600-8. doi: 10.1002/rcm.5021. PubMed PMID: 21594935.

Yang L, Nyalwidhe J O, Guo S, Drake R R, Semmes O J. Targeted identification of metastasis-associated cell-surface sialoglycoproteins in prostate cancer. Mol Cell Proteomics. 2011 June; 10(6):M110.007294. doi: 10.1074/mcp.M110.007294. Epub 2011 Mar. 29. PubMed PMID: 21447706; PubMed Central PMCID: PMC3108840.

Ying W. NAD+ and NADH in cellular functions and cell death. Front Biosci. 2006 Sep. 1; 11:3129-48. Review. PubMed PMID: 16720381.

Farber, D. B., *From mice to men: the cyclic GMP phosphodiesterase gene in vision and disease. The Proctor Lecture.* Invest. Ophthalmol. Vis. Sci., 1995. 36(2): p. 263-275.

Farber, D. B. and R. N. Lolley, *Cyclic guanosine monophosphate: elevation in degenerating photoreceptor cells of the C3H mouse retina.* Science, 1974. 186: p. 449-451.

Fox, D. A., A. T. Poblenz, and L. He, *Calcium overload triggers rod photoreceptor apoptotic cell death in chemical-induced and inherited retinal degenerations.* Ann. N.Y. Acad. Sci., 1999. 893: p. 282-285.

Ogilvie, J. M., et al., *A reliable method for organ culture of neonatal mouse retina with long-term survival.* J. Neurosci. Methods, 1999. 87(1): p. 57-65.

It is to be understood that the invention is not limited to the particular embodiments of the invention described above, as variations of the particular embodiments may be made and still fall within the scope of the appended claims.

What is claimed is:

1. A compound of formula (I):

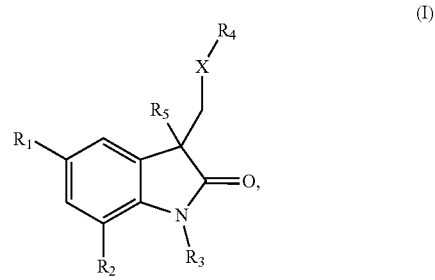

wherein:

X is —C(O)— or a single bond;

$R_1$ is lower alkyl or halogen;

$R_2$ is hydrogen, lower alkyl or halogen;

$R_3$ is unsubstituted lower alkyl or lower alkyl monosubstituted with —C≡CH, piperidinyl, —$N_3$, morpholinyl or phenyl, wherein $R_3$ is not methyl when X is —C(O)—;

$R_4$ is (i) pyridinyl, mono- or bi-substituted independently with halogen, hydroxyl, alkoxy or —C≡CH,
(ii) phenyl, unsubstituted or mono-, bi- or tri-substituted independently with alkoxy or hydroxy,
(iii) 1H-indo-3-yl, or
(iv) 1-benzoyl-1H-indol-3-yl; and $R_5$ is hydroxyl or —OBz, or a pharmaceutically acceptable salt thereof.

2. The compound according to claim 1, wherein X is —C(O)—.

3. The compound according to claim 1, wherein X is a single bond.

4. The compound according to claim 1, wherein $R_1$ is lower alkyl or halogen.

5. The compound according to claim 1, wherein $R_2$ is hydrogen.

6. The compound according to claim 1, wherein one $R_1$ is methyl and $R_2$ is hydrogen.

7. The compound according to claim 1, wherein $R_1$ is chlorine and $R_2$ is hydrogen.

8. The compound according to claim 1, wherein both $R_1$ and $R_2$ are chlorine.

9. The compound according to claim 1, wherein $R_3$ is an unbranched, unsubstituted lower alkyl.

10. The compound according to claim 1, wherein $R_3$ is a branched, unsubstituted lower alkyl.

11. The compound according to claim 1, wherein $R_3$ is lower alkyl mono-substituted with —C≡CH, piperidinyl, —$N_3$, morpholinyl or phenyl.

12. The compound according to claim 1, wherein $R_4$ is pyridinyl mono- or bi-substituted independently with halogen, hydroxyl, alkoxy or —C≡CH.

13. The compound according to claim 1, wherein $R_4$ is unsubstituted phenyl.

14. The compound according to claim 1, wherein $R_4$ is phenyl monosubstituted with alkoxy or hydroxyl.

15. The compound according to claim 1, wherein $R_4$ phenyl bi-substituted independently with alkoxy or hydroxyl.

16. The compound according to claim 1, wherein $R_4$ is phenyl tri-substituted independently with alkoxy or halogen.

17. The compound according to claim 1, wherein $R_4$ is phenyl monosubstituted with methoxy.

18. The compound according to claim 1, Wherein $R_4$ is phenyl bi-substituted with methoxy.

19. The compound according to claim 1, wherein $R_4$ is phenyl tri-substituted with methoxy.

20. The compound according to claim 1, wherein $R_4$ is 1H-indo-3-yl, or 1-benzoyl-1H-indol-3-yl.

21. The compound according to claim 1, wherein $R_5$ is hydroxyl.

22. The compound according to claim 1, wherein $R_5$ is —OBz.

23. The compound according to claim 1, wherein X is a single bond and R4 is phenyl, unsubstituted or mono-, bi- or tri-substituted independently with alkoxy or hydroxyl.

24. A compound, wherein said compound is:
3((3-bromopyridin-2-yl)methyl)-3-hydroxy-1-isopentyl-5-methylindolin-2-one;
5-chloro-1-ethyl-3-hydroxy-3-((4-hydroxypyridin-2-yl) methyl) indolin-2-one;
5-chloro-3-hydroxy-3((3-methoxypyridin-2-yl)methyl)-1-phenethylindoin-2-one;
5-chloro-3-hydroxy-1-(2-(piperidin-1-yl)ethyl)-3-(pyridin-2-ylmethyl)indolin-2-one;
5-chloro-3-hydroxy-3-((5-methoxypyridin-2-yl)methyl)-1-propylindolin-2-one;
3-hydroxy-3-((5-methoxypyridin-2-yl)methyl)-5-methyl-1-propylindolin-2-one;
5-chloro-1-ethyl-3-hydroxy-3-((3-methoxypyridin-2-yl) methyl)indolin-2-one;
1-ethyl-3-hydroxy-3-((3-methoxypyridin-2-yl)methyl)-5-methylindolin-2-one;
3-hydroxy-5-methyl-1-phenethyl-3-(pyridin-2-ylmethyl) indolin-2-one;
5-chloro-1-ethyl-3-hydroxy-3-(pyridin-2-ylmethyl)indolin-2-one;
3-hydroxy-3-((5-methoxypyridin-2-yl)methyl)-5-methyl-1-phenethylindolin-2-one;
1-butyl -3-hydroxy-3-(2-oxo-2-(pyridin-2-yl)ethyl)indolin-2-one;
3-(2-(1H-indol-3-yl)-2-oxoethyl)-3-hydroxy-5-methyl-1-(pent-4-yn-1-yl)indolin-2-one;
5-chloro-3-(2-(6-ethynylpyridin-2-yl)-2-oxoethyl)-3-hydroxy-1-propylindolin-2-one;
3-(2-(1H-indol-3-yl)-2-oxoethyl)-3-hydroxy-1-isopentyl-5-methylindolin-2-one;
3-hydroxy-1-isobutyl-3-(2-oxo-2-(pyridin-2-yl)ethyl)indolin-2-one;
5-chloro-3-hydroxy-1-isobutyl-3-(2-(6-methoxypyridin-2-yl)-2-oxoethyl)indolin-2-one;
5-chloro-3-hydroxy-3-(2-(6-methoxypyridin-2-yl)-2-oxoethyl)-1-(2-(piperidin-1-yl)ethyl)indolin-2-one;
5-chloro-1-ethyl-3-hydroxy-3-(2-oxo-2-(pyridin-2-yl) ethyl)indolin-2-one;
3-(2-(1H-indol -3-yl)-2-oxoethyl)-3-hydroxy-1-isobutyl-indolin-2-one;
3-(2-(1H-indol-3-yl)-2-oxoethyl)-3-hydroxy-1-isopentyl-indolin-2-one;
5-chloro-3-(2-(2,6-dimethoxypyridin-3-yl)-2-oxoethyl)-3-hydroxy-1-propylindolin-2-one;
5-chloro-3-hydroxy-3-(2-oxo -2-(pyridin-2-yl)ethyl)-1-propylindol in-2-one;
3-(2-(1H-indol-3-yl)-2-oxoethyl)-3-hydroxy-5-methyl-1-propylindolin-2-one;
3-(2-(2,6-dimethoxypyridin-3-yl)-2-oxoethyl)-3-hydroxy-5-methyl-1-propylindolin-2-one;
3-hydroxy-3-(2-(6-methoxypyridin-2-yl)-2-oxoethyl)-5-methyl-1-propylindolin-2-one;
3-(2-(1H-indol-3-yl)-2-oxoethyl)-1-(3-azidopropyl)-3-hydroxy-5-methylindolin-2-one;
1-(3-azidopropyl)-3-hydroxy-3-(2-(6-methoxypyridin-2-yl)-2-oxoethyl)-5-methylindolin-2-one;
3-hydroxy-1-isobutyl-3-(2-(6-methoxypyridin-2-yl)-2-oxoethyl)-5-methylindolin-2-one;
5,7-dichloro-3-hydroxy-3-(2-(6-methoxypyridin-2-yl)-2-oxoethyl)-1-propylindolin-2-one;
3-(2-(1H-indol-3-yl)-2-oxoethyl)-5-chloro-3-hydroxy-1-propylindolin-2-one;
5-chloro-3-hydroxy-1-isobutyl-3-(2-oxo-2-(pyridin-2-yl) ethyl)indolin-2-one; 1-ethyl-5-methyl-2-oxo-3-(3,4,5-trimethoxybenzyl)indolin-3-yl benzoate;
1-ethyl-3-hydroxy-5-methyl-3-(3,4,5-trimethoxybenzyl) indolin-2-one;
5-chloro-1-isobutyl-2-oxo-3-(3,4,5-trimetboxybenzyl)indolin-3-yl benzoate;
1-isobutyl-5-methyl-2-oxo-3-(3,4,5-trimethoxybenzyl)indolin-3-yl benzoate;
3-hydroxy-1-isobutyl-5-methyl-3-(3,4,5-trimethoxybenzyl)indolin-2-one;
3-(3,5-dirnetboxybenzyl)-1-ethyl-5-methyl-2-oxoindolin-3-yl benzoate;
3-3,5-dimethoxybenzyl)-5-methyl-2-oxo-1-phenethylindolin-3-yl benzoate;
5-chloro-1-ethyl-3-(3-metboxybenzyl)-2-oxoindolin-3-yl benzoate;
1-butyl-5-chloro-3-(3,5-dimethoxybenzyl)-3-hydroxyindolin-2-one;
1-butyl-5-chloro-3-hydroxy-3-(3-methoxybenzyl)indolin-2-one;
3-hydroxy-3-(3-methoxybenzyl)-5-methyl-1-propylindolin-2-one;
3-(3,4-dimethoxybenzyl)-5-methyl-2-oxo-1-phenethylindolin-3-yl benzoate;
3-(3,4-dimethoxybenzyl-1-isopentyl-2-oxoindolin-3-yl benzoate;
3-(3,4-dimethoxybenzyl)-1-isopentyl -5-methyl-2-oxoindolin-3-yl benzoate;
3-(3,4-dimethoxybenzyl)-5-methyl-2-oxo-1-propylindolin-3-yl benzoate;
3-hydroxy-1-isobutyl-3-(3,4,5-trimethoxybenzyl)indolin-2-one;
1-isobutyl-2-oxo-3-(3,4,5-trimethoxybenzyl)indolin-3-yl benzoate;
5-chloro-2-oxo-1-phenethyl-3-(3,4,5-trimethoxybenzyl) indolin-3-yl benzoate;
1-ethyl-3-hydroxy-3-(4-methoxybenzyl)-5-methylindolin-2-one;

3(2-hydroxy-4-methoxybenzyl)-2-oxo-1-propylindolin-3-yl benzoate;
3-(2-hydroxy-4-methoxybenzyl)-5-methyl-1-(4-methylpentyl)-2-oxoindolin-3-yl benzoate;
3-(2-hydroxy-5-methoxybenzyl)-1-isobutyl-2-oxoindolin-3-yl benzoate;
5-chloro-3-(2-hydroxy-3-methoxybenzyl)-1-isopentyl-2-oxoindolin-3-yl benzoate;
5-chloro-3-(2-hydroxy-4-methoxybenzyl-1-(3-morpholinopropyl)-2-oxoindolin-3-yl benzoate;
1-ethyl-3-(2-hydroxy-4-methoxybenzyl)-2-oxoindolin-3-yl benzoate;
3-(2-hydroxy-5-methoxybenzyl)-5-methyl-1-(4-methylpentyl)-2-oxoindolin-3-yl benzoate;
5-chloro-1-ethyl-3-(2-hydroxy-3-methoxybenzyl)-2-oxoindolin-3-yl benzoate;
1-ethyl-3-)2-hydroxy-5-methoxybenzyl)-5-methyl-2-oxoindolin-3-yl benzoate;
5-chloro-3-(2-hydroxy-5-methoxybenzyl)-2-oxo-1-phenethylindolin-3-yl benzoate;
5-chloro-1-ethyl-3-(2-hydroxy-5-methoxybenzyl)-2-oxoindolin-3-yl benzoate;
3((1H-indol-3-yl)methyl)-5-chloro-2-oxo-1-propylindolin-3-yl benzoate;
3-((1-benzoyl-1H-indol-3-yl)methyl)-3-hydroxy-5-methyl-1-propylindolin-2-one; or
3-((1H-indol-3-yl)methyl)-1-butyl-2-oxoindolin-3-yl benzoate,
or a pharmaceutically acceptable salt thereof.

25. A pharmaceutical composition, comprising a therapeutically effective amount of a compound according to claim 1 or a pharmaceutically acceptable salt thereof and a pharmaceutically acceptable carrier.

26. A pharmaceutical composition, comprising a therapeutically effective amount of a compound according to claim 24, or a pharmaceutically acceptable salt thereof, and a pharmaceutically acceptable carrier.

* * * * *